(12) United States Patent
Low et al.

(10) Patent No.: US 10,080,805 B2
(45) Date of Patent: Sep. 25, 2018

(54) CHOLECYSTOKININ B RECEPTOR TARGETING FOR IMAGING AND THERAPY

(71) Applicant: Purdue Research Foundation, West Lafayette, IN (US)

(72) Inventors: Philip S. Low, West Lafayette, IN (US); Charity Wayua, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 250 days.

(21) Appl. No.: 14/380,273

(22) PCT Filed: Feb. 22, 2013

(86) PCT No.: PCT/US2013/027463
§ 371 (c)(1),
(2) Date: Aug. 21, 2014

(87) PCT Pub. No.: WO2013/126797
PCT Pub. Date: Aug. 29, 2013

(65) Prior Publication Data
US 2015/0050212 A1    Feb. 19, 2015

Related U.S. Application Data

(60) Provisional application No. 61/602,831, filed on Feb. 24, 2012.

(51) Int. Cl.
| | | |
|---|---|---|
| *A61K 51/00* | (2006.01) | |
| *A61M 36/14* | (2006.01) | |
| *A61K 47/48* | (2006.01) | |
| *C07D 405/12* | (2006.01) | |
| *C07D 243/12* | (2006.01) | |
| *A61K 51/04* | (2006.01) | |
| *A61K 31/4409* | (2006.01) | |
| *A61K 31/475* | (2006.01) | |
| *A61K 38/06* | (2006.01) | |
| *A61K 38/07* | (2006.01) | |
| *A61K 38/08* | (2006.01) | |
| *A61K 49/00* | (2006.01) | |
| *A61K 51/02* | (2006.01) | |

(52) U.S. Cl.
CPC .... *A61K 47/48061* (2013.01); *A61K 31/4409* (2013.01); *A61K 31/475* (2013.01); *A61K 38/06* (2013.01); *A61K 38/07* (2013.01); *A61K 38/08* (2013.01); *A61K 49/0052* (2013.01); *A61K 51/02* (2013.01); *A61K 51/047* (2013.01); *A61K 51/0468* (2013.01); *C07D 243/12* (2013.01); *C07D 405/12* (2013.01)

(58) Field of Classification Search
CPC .. A61K 47/00; A61K 47/48061; A61K 49/00; A61K 49/005; A61K 51/00; A61K 51/0468; A61K 31/00; A61K 31/4409; A61K 31/475; A61K 38/00; A61K 38/06; A61K 38/07; A61K 38/08; C07D 405/12; C07D 243/12
USPC .......... 424/1.11, 1.65, 1.69, 1.81, 1.85, 1.89, 424/9.1, 9.2, 9.3, 9.4, 9.5, 9.6; 534/7, 534/10–16; 514/1, 1.1, 19.2, 19.3, 19.4, 514/19.5, 19.6; 530/300
See application file for complete search history.

(56) References Cited

U.S. PATENT DOCUMENTS

| | | |
|---|---|---|
| 2,515,483 A | 7/1950 | Wolf et al. |
| 2,816,110 A | 12/1957 | Sletzinger et al. |
| 3,387,001 A | 6/1968 | Hargrove et al. |
| 3,392,173 A | 7/1968 | Hargrove et al. |
| 3,632,622 A | 1/1972 | Moore et al. |
| 3,641,109 A | 2/1972 | Emerson et al. |
| 4,166,810 A | 9/1979 | Cullinan et al. |
| 4,203,898 A | 5/1980 | Cullinan et al. |
| 4,316,885 A | 2/1982 | Rakhit |
| 4,337,339 A | 6/1982 | Farina et al. |
| 4,639,456 A | 1/1987 | Trouet et al. |
| 4,650,803 A | 3/1987 | Stella et al. |
| 4,691,024 A | 9/1987 | Shirahata |
| 4,713,249 A | 12/1987 | Schroder |
| 4,801,688 A | 1/1989 | Laguzza et al. |
| 4,866,180 A | 9/1989 | Vyas et al. |
| 4,870,162 A | 9/1989 | Trouet et al. |
| 5,006,652 A | 4/1991 | Cullinan et al. |
| 5,094,849 A | 3/1992 | Cullinan et al. |
| 5,100,883 A | 3/1992 | Schiehser |
| 5,108,921 A | 4/1992 | Low et al. |
| 5,118,677 A | 6/1992 | Caufield |
| 5,118,678 A | 6/1992 | Kao et al. |

(Continued)

FOREIGN PATENT DOCUMENTS

| | | |
|---|---|---|
| CA | 2372841 | 11/2000 |
| CA | 2376175 | 12/2000 |

(Continued)

OTHER PUBLICATIONS

Harikumar et al, J. Med. Chem., vol. 53, No. 7, pp. 2836-2842. (Year: 2010).*
Kawasaki, D. et al., Effect of Z-360, a novel orally active CCK-2/gastrin receptor antagonist on tumor growth in human pancreatic adenocarcinoma cell lines in vivo and mode of action determinations in vitro, Cancer Chemotherapy and Pharmacology, 2008, vol. 61, No. 5, pp. 883-892.
International Search Report for PCT/US2013/027463, dated Jun. 27, 2013.
Achilefu et al. "A New Method for the Synthesis of Tri-tert-butyl Diethylenetriaminepentaacetic Acid Its Derivatives" *J. Org. Chem.* 2000; 65:1562-1565.

(Continued)

*Primary Examiner* — D. L. Jones
(74) *Attorney, Agent, or Firm* — Barnes & Thornburg LLP

(57) ABSTRACT

Conjugates are described herein where CCK2R targeting ligands are attached to an active moiety, such as therapeutic agent or an imaging agent, through a linker. The conjugates can be used in the detection, diagnosis, imaging and treatment of cancer.

1 Claim, 21 Drawing Sheets

(56) References Cited

U.S. PATENT DOCUMENTS

| | | |
|---|---|---|
| 5,120,842 A | 6/1992 | Failli et al. |
| 5,130,307 A | 7/1992 | Failli et al. |
| 5,138,051 A | 8/1992 | Hughes et al. |
| 5,140,104 A | 8/1992 | Coughlin et al. |
| 5,151,413 A | 9/1992 | Caufield et al. |
| 5,169,851 A | 12/1992 | Hughes et al. |
| 5,194,447 A | 3/1993 | Kao |
| 5,221,670 A | 6/1993 | Caufield |
| 5,233,036 A | 8/1993 | Hughes |
| 5,258,389 A | 11/1993 | Goulet et al. |
| 5,260,300 A | 11/1993 | Hu |
| 5,266,333 A | 11/1993 | Cady |
| 5,302,584 A | 4/1994 | Kao et al. |
| 5,362,718 A | 11/1994 | Skotnicki et al. |
| 5,378,696 A | 1/1995 | Caufield |
| 5,385,908 A | 1/1995 | Nelson et al. |
| 5,385,909 A | 1/1995 | Nelson et al. |
| 5,385,910 A | 1/1995 | Ocain et al. |
| 5,389,639 A | 2/1995 | Failli et al. |
| 5,391,730 A | 2/1995 | Skotnicki et al. |
| 5,416,016 A | 5/1995 | Low et al. |
| 5,417,982 A | 5/1995 | Modi |
| 5,463,048 A | 10/1995 | Skotnicki et al. |
| 5,491,231 A | 2/1996 | Nelson et al. |
| 5,547,668 A | 8/1996 | Kranz et al. |
| 5,552,545 A | 9/1996 | Pearce et al. |
| 5,562,907 A | 10/1996 | Arnon |
| 5,583,020 A | 12/1996 | Sullivan |
| 5,627,165 A | 5/1997 | Glazier |
| 5,635,382 A | 6/1997 | Low et al. |
| 5,672,486 A | 9/1997 | Soulillou |
| 5,688,488 A | 11/1997 | Low et al. |
| 5,998,603 A | 12/1999 | Cook |
| 6,004,555 A | 12/1999 | Thorpe et al. |
| 6,030,941 A | 2/2000 | Summerton et al. |
| 6,056,973 A | 5/2000 | Allen |
| 6,077,499 A | 6/2000 | Griffiths |
| 6,093,382 A | 7/2000 | Wedeking et al. |
| 6,171,614 B1 | 1/2001 | Chaikof et al. |
| 6,171,859 B1 | 1/2001 | Herrnstadt et al. |
| 6,177,404 B1 | 1/2001 | DeFeo-Jones et al. |
| 6,184,042 B1 | 2/2001 | Neumann et al. |
| 6,207,157 B1 | 3/2001 | Gu et al. |
| 6,290,929 B1 | 9/2001 | Camden |
| 6,291,673 B1 | 9/2001 | Fuchs et al. |
| 6,291,684 B1 | 9/2001 | Borzilleri et al. |
| 6,315,978 B1 | 11/2001 | Grissom et al. |
| 6,335,434 B1 | 1/2002 | Guzaev et al. |
| 6,340,701 B1 | 1/2002 | Chari et al. |
| 6,342,244 B1 | 1/2002 | Zalipsky et al. |
| 6,344,452 B1 | 2/2002 | Shinozaki et al. |
| 6,365,179 B1 | 4/2002 | Zalipsky et al. |
| 6,399,625 B1 | 6/2002 | Zhu |
| 6,399,626 B1 | 6/2002 | Zhu et al. |
| 6,399,638 B1 | 6/2002 | Vite et al. |
| 6,432,973 B1 | 8/2002 | Zhu et al. |
| 6,440,991 B1 | 8/2002 | Zhu et al. |
| 6,511,986 B2 | 1/2003 | Zhang et al. |
| 6,541,612 B2 | 4/2003 | Molnar-Kimber et al. |
| 6,548,505 B1 | 4/2003 | Martin et al. |
| 6,596,757 B1 | 7/2003 | Chari et al. |
| 6,617,333 B2 | 9/2003 | Raibindran et al. |
| 6,670,355 B2 | 12/2003 | Azrulan et al. |
| 6,677,357 B2 | 1/2004 | Zhu et al. |
| 6,680,330 B2 | 1/2004 | Zhu et al. |
| 6,713,607 B2 | 3/2004 | Caggiano et al. |
| 6,747,022 B2 | 6/2004 | Shinozaki et al. |
| 6,800,653 B2 | 10/2004 | Regueiro-Ren et al. |
| 6,821,731 B2 | 11/2004 | Gillis et al. |
| 6,915,855 B2 | 7/2005 | Steele et al. |
| 6,958,153 B1 | 10/2005 | Ormerod et al. |
| 7,019,014 B2 | 3/2006 | Bernan et al. |
| 7,029,674 B2 | 4/2006 | Carreno et al. |
| 7,033,594 B2 | 4/2006 | Low et al. |
| 7,060,709 B2 | 6/2006 | Cooperstone et al. |
| 7,060,797 B2 | 6/2006 | O'Toole et al. |
| 7,067,111 B1 | 6/2006 | Yang et al. |
| 7,074,804 B2 | 7/2006 | Zhu et al. |
| 7,105,328 B2 | 9/2006 | Wood et al. |
| 7,122,361 B2 | 10/2006 | Liu et al. |
| 7,128,893 B2 | 10/2006 | Leamon et al. |
| 7,153,957 B2 | 12/2006 | Chew et al. |
| 7,238,368 B2 | 7/2007 | Zalipsky et al. |
| 7,279,562 B2 | 10/2007 | Molnar-Kimber et al. |
| 7,582,744 B2 | 9/2009 | Manoharan et al. |
| 7,601,332 B2 | 10/2009 | Vlahov et al. |
| 7,754,885 B2 | 7/2010 | Hoefle et al. |
| 7,776,814 B2 | 8/2010 | Dömling et al. |
| 7,816,377 B2 | 10/2010 | Dömling et al. |
| 7,875,612 B2 | 1/2011 | Green et al. |
| 7,910,594 B2 | 3/2011 | Vlahov et al. |
| 8,044,200 B2 | 10/2011 | Xu et al. |
| 8,105,568 B2 | 1/2012 | Vlahov et al. |
| 8,288,557 B2 | 10/2012 | Vlahov et al. |
| 8,349,901 B2 | 1/2013 | Satyam |
| 8,383,122 B2 | 2/2013 | Dai et al. |
| 8,394,922 B2 | 3/2013 | Cheng et al. |
| 8,465,724 B2 | 6/2013 | Vlahov et al. |
| 8,470,822 B2 | 6/2013 | Green et al. |
| 8,476,451 B2 | 7/2013 | Ellman et al. |
| 8,497,365 B2 | 7/2013 | Davis et al. |
| 8,546,425 B2 | 10/2013 | Leamon et al. |
| 8,580,820 B2 | 11/2013 | Zanda et al. |
| 8,765,096 B2 | 7/2014 | Leamon et al. |
| 8,802,632 B2 | 8/2014 | Cheng et al. |
| 8,889,880 B2 | 11/2014 | Vlahov et al. |
| 9,061,995 B2 | 6/2015 | Chari et al. |
| 9,090,563 B2 | 7/2015 | Vlahov et al. |
| 9,138,484 B2 | 9/2015 | Leamon et al. |
| 9,192,682 B2 | 11/2015 | Leamon et al. |
| 9,295,731 B2 | 3/2016 | Nguyen |
| 9,550,734 B2 | 1/2017 | Vlahov et al. |
| 9,662,402 B2 | 5/2017 | Vlahov et al. |
| 2001/0031252 A1 | 10/2001 | Low et al. |
| 2002/0151088 A1 | 10/2002 | Molnar-Kimber et al. |
| 2003/0022831 A1 | 1/2003 | Rothbard et al. |
| 2003/0086900 A1 | 5/2003 | Low et al. |
| 2003/0162234 A1 | 8/2003 | Jallad |
| 2003/0194409 A1 | 10/2003 | Rothman et al. |
| 2004/0018203 A1 | 1/2004 | Pastan et al. |
| 2004/0033195 A1 | 2/2004 | Leamon et al. |
| 2004/0047917 A1 | 3/2004 | Wilson et al. |
| 2004/0242582 A1 | 12/2004 | Green et al. |
| 2005/0002942 A1 | 1/2005 | Vlahov et al. |
| 2005/0004010 A1 | 1/2005 | Collins et al. |
| 2005/0026068 A1 | 2/2005 | Gogolides et al. |
| 2005/0107325 A1 | 5/2005 | Manoharan et al. |
| 2005/0165227 A1 | 7/2005 | Vlahov et al. |
| 2005/0227985 A9 | 10/2005 | Green et al. |
| 2005/0239713 A1 | 10/2005 | Domling et al. |
| 2005/0239739 A1 | 10/2005 | Matulic-Adamic et al. |
| 2005/0249740 A1 | 11/2005 | Doemling |
| 2006/0019911 A1 | 1/2006 | Papisov |
| 2006/0058266 A1 | 3/2006 | Manoharan et al. |
| 2006/0105975 A1 | 5/2006 | Pendergrast et al. |
| 2006/0128754 A1 | 6/2006 | Hoefle et al. |
| 2006/0217360 A1 | 9/2006 | Hoefle et al. |
| 2006/0222653 A1 | 10/2006 | Abel et al. |
| 2007/0009434 A1 | 1/2007 | Low et al. |
| 2007/0134332 A1 | 6/2007 | Turnell et al. |
| 2007/0275904 A1 | 11/2007 | Vite et al. |
| 2008/0096893 A1 | 4/2008 | Zebala |
| 2008/0207625 A1 | 8/2008 | Xu et al. |
| 2008/0248052 A1 | 10/2008 | Vlahov et al. |
| 2008/0280937 A1 | 11/2008 | Leamon et al. |
| 2009/0203889 A1 | 8/2009 | Vlahov et al. |
| 2009/0247614 A1 | 10/2009 | Manoharan et al. |
| 2010/0004276 A1 | 1/2010 | Vlahov et al. |
| 2010/0040669 A1 | 2/2010 | Higuchi |
| 2010/0048490 A1 | 2/2010 | Vlahov et al. |
| 2010/0074863 A1 | 3/2010 | Or et al. |
| 2010/0104626 A1 | 4/2010 | Leamon et al. |
| 2010/0129314 A1 | 5/2010 | Singh et al. |
| 2010/0144647 A1 | 6/2010 | Kratz et al. |

(56) References Cited

U.S. PATENT DOCUMENTS

| | | |
|---|---|---|
| 2010/0240701 A1 | 9/2010 | Vlahov et al. |
| 2010/0323973 A1 | 12/2010 | Leamon et al. |
| 2011/0027274 A1 | 2/2011 | Cheng et al. |
| 2011/0166319 A1 | 7/2011 | Dai et al. |
| 2011/0172254 A1 | 7/2011 | Leamon et al. |
| 2011/0245295 A1 | 10/2011 | Chai et al. |
| 2012/0022245 A1 | 1/2012 | Low et al. |
| 2012/0065149 A1 | 3/2012 | Vlahov et al. |
| 2012/0129779 A1 | 5/2012 | Richter |
| 2012/0252738 A1 | 10/2012 | Richter |
| 2012/0252739 A1 | 10/2012 | Richter |
| 2012/0258905 A1 | 10/2012 | Leamon et al. |
| 2012/0259100 A1 | 10/2012 | Jin |
| 2012/0322741 A1 | 12/2012 | Low et al. |
| 2013/0029900 A1 | 1/2013 | Widdison |
| 2013/0116195 A1 | 5/2013 | Leamon et al. |
| 2013/0137139 A1 | 5/2013 | Vlahov et al. |
| 2013/0184435 A1 | 7/2013 | Vlahov et al. |
| 2013/0203680 A1 | 8/2013 | Leamon et al. |
| 2013/0217638 A1 | 8/2013 | Wessjohann et al. |
| 2013/0224228 A1 | 8/2013 | Jackson et al. |
| 2013/0252904 A1 | 9/2013 | Leamon et al. |
| 2013/0281678 A1 | 10/2013 | Dai et al. |
| 2014/0058063 A1 | 2/2014 | Vlahov et al. |
| 2014/0058064 A1 | 2/2014 | Vlahov et al. |
| 2014/0066594 A1 | 3/2014 | Vlahov et al. |
| 2014/0073761 A1 | 3/2014 | Leamon et al. |
| 2014/0073763 A1 | 3/2014 | Low et al. |
| 2014/0080175 A1 | 3/2014 | Vlahov et al. |
| 2014/0107316 A1 | 4/2014 | Vlahov et al. |
| 2014/0154702 A1 | 6/2014 | Parker et al. |
| 2014/0193437 A1 | 7/2014 | Lin et al. |
| 2014/0213760 A1 | 7/2014 | Keanib et al. |
| 2014/0227295 A1 | 8/2014 | Cong et al. |
| 2014/0227298 A1 | 8/2014 | Cong et al. |
| 2014/0249315 A1 | 9/2014 | Vlahov et al. |
| 2014/0309406 A1 | 10/2014 | Li et al. |
| 2014/0323690 A1 | 10/2014 | Cheng et al. |
| 2015/0250896 A1 | 9/2015 | Zhao |
| 2015/0258203 A1 | 9/2015 | Vlahov et al. |
| 2015/0284416 A1 | 10/2015 | Zhao |
| 2015/0314015 A1 | 11/2015 | Leamon et al. |
| 2016/0002167 A1 | 1/2016 | Vlahov et al. |
| 2016/0108085 A1 | 4/2016 | Vlahov et al. |
| 2016/0129027 A1 | 5/2016 | Nguyen |
| 2016/0144050 A1 | 5/2016 | Kim et al. |
| 2016/0168183 A1 | 6/2016 | Leamon et al. |
| 2016/0220694 A1 | 8/2016 | Vlahov et al. |
| 2017/0151340 A1 | 6/2017 | Leamon et al. |
| 2017/0290878 A1 | 10/2017 | Leamon et al. |

FOREIGN PATENT DOCUMENTS

| | | |
|---|---|---|
| CN | 101784565 A | 7/2010 |
| EP | 0116208 A1 | 8/1984 |
| EP | 0163550 A2 | 12/1985 |
| EP | 0280741 A1 | 12/1987 |
| EP | 0354728 | 9/1988 |
| EP | 0247792 | 11/1990 |
| IL | 93983 | 2/1990 |
| JP | 59-175493 | 5/1983 |
| JP | 60-255789 | 12/1985 |
| WO | WO 1985/005554 | 12/1985 |
| WO | WO 1988/001622 | 3/1988 |
| WO | WO 1990/012096 | 10/1990 |
| WO | WO 1991/007418 | 5/1991 |
| WO | WO 1995/015335 | 6/1995 |
| WO | WO 1996/036367 | 11/1996 |
| WO | WO 1998/008382 | 3/1998 |
| WO | WO 1998/008859 | 3/1998 |
| WO | WO 1998/010651 | 3/1998 |
| WO | WO 1999/020626 | 4/1999 |
| WO | WO 1999/061055 | 12/1999 |
| WO | WO 2000/035422 | 6/2000 |
| WO | WO 2000/066091 | 11/2000 |
| WO | WO 2000/074721 | 12/2000 |
| WO | WO 2001/013957 | 3/2001 |
| WO | WO 2001/028592 | 4/2001 |
| WO | WO 2001/074382 | 10/2001 |
| WO | WO 2002/059272 | 8/2002 |
| WO | WO 2002/085908 | 10/2002 |
| WO | WO 2002/087424 | 11/2002 |
| WO | WO 2002/098868 | 12/2002 |
| WO | WO 2003/050295 | 6/2003 |
| WO | WO 2003/092742 | 11/2003 |
| WO | WO 2003/097647 | 11/2003 |
| WO | WO 2004/005326 | 1/2004 |
| WO | WO 2004/005327 | 1/2004 |
| WO | WO 2004/012735 | 2/2004 |
| WO | WO 2004/022099 | 3/2004 |
| WO | WO 2004/037210 | 5/2004 |
| WO | WO 2004/046170 | 6/2004 |
| WO | WO 2004/054622 | 7/2004 |
| WO | WO 2004/069159 | 8/2004 |
| WO | WO 2004/100983 | 11/2004 |
| WO | WO 2005/074901 | 8/2005 |
| WO | WO 2005/112919 | 12/2005 |
| WO | WO 2005/115912 | 12/2005 |
| WO | WO 2006/012527 | 2/2006 |
| WO | WO 2006/042146 | 4/2006 |
| WO | WO 2006/089007 | 8/2006 |
| WO | WO 2006/101845 | 9/2006 |
| WO | WO 2006/105141 | 10/2006 |
| WO | WO 2007/002222 | 1/2007 |
| WO | 2007/022493 | 2/2007 |
| WO | WO 2007/022493 | 2/2007 |
| WO | WO 2007/022494 | 2/2007 |
| WO | WO 2007/022512 | 2/2007 |
| WO | WO 2007/140298 | 12/2007 |
| WO | WO 2008/057437 | 5/2008 |
| WO | WO 2008/101231 | 8/2008 |
| WO | 2008/112873 | 9/2008 |
| WO | WO 2008/112873 | 10/2008 |
| WO | WO 2009/002993 | 12/2008 |
| WO | 2009/026177 | 2/2009 |
| WO | WO 2009/055562 | 4/2009 |
| WO | WO 2010/033733 | 3/2010 |
| WO | WO 2010/045598 | 4/2010 |
| WO | WO 2011/069116 | 6/2011 |
| WO | WO 2011/106639 | 9/2011 |
| WO | WO 2011/130598 | 10/2011 |
| WO | WO 2012/019123 | 2/2012 |
| WO | WO 2012/047525 | 4/2012 |
| WO | WO 2012/090104 | 7/2012 |
| WO | WO 2012/122893 | 9/2012 |
| WO | WO 2013/126797 | 8/2013 |
| WO | WO 2013/130776 | 9/2013 |
| WO | WO 2013/149185 | 10/2013 |
| WO | WO 2013/170272 | 11/2013 |
| WO | WO 2013/173392 | 11/2013 |
| WO | WO 2013/173393 | 11/2013 |
| WO | WO 2014/009774 | 1/2014 |
| WO | WO 2014/040752 | 3/2014 |
| WO | WO 2014/062697 | 4/2014 |
| WO | WO 2014/078484 | 5/2014 |
| WO | WO 2014/080251 | 5/2014 |
| WO | WO 2015/106599 | 7/2015 |
| WO | WO 2016/147031 | 9/2016 |

OTHER PUBLICATIONS

Adessi, C. et al., "Converting a Peptide into a Drug: Strategies to Improve Stability and Bioavailability," *Current Medicinal Chemistry*, 2002, 9, 963-978.

Agoston E.S. et al., "Vitamin D Analogs as Anti-Carcinogenic Agents," *Anti-Cancer Agents in Medicinal Chemistry*, 2006; 6(1): 53-71.

Anderson et al., "Potocytosis: Sequestration and transport of small molecules by caveolae," *Science*, 1992; 255: 410-411.

Angier et al., Science, 1946, 103: 667-669.

Angier, R. B., et al., "Pteroic Acid Analogs Containing Arsenic," J. American Chem. Soc., vol. 76, 1954, pp. 902-904.

(56) References Cited

OTHER PUBLICATIONS

Antony A.C. et al., "Studies of the Role of a Particulate Folate-binding Protein in the Uptake of 5-Methyltetrahydrofolate by Cultured Human KB Cells," *J. Biological Chem.*, 1985; 260(28):14911-7.
Antony A.C., "Folate receptors," *Annu Rev Nutr*, 1996; 16: 501-21.
Antony A.C., "The biological chemistry of folate receptors," *Blood*, 1992; 79(11):2807-2820.
Antony, "Folate receptors: reflections on a personal odysssey and a perspective on unfolding truth," Advanced Drug Delivery Reviews, 2004; vol. 56: 1059-66.
Archer M.C. et al., "Separation of Folic Acid Derivatives and Pterins by High-Performance Liquid Chromatography," *Methods in Enzymology*, 1980; 66: pp. 452-459.
Arya et al., "Design and Synthesis of Analogs of Vitamin E: Antiproliferative Activity Against Human Breast Adenocarcinoma Cells," *Bioorganic & Medicinal Chemistry Letters*, 1998; vol. 8, pp. 2433-2438.
Atkinson SF et al., "Conjugation of folate via gelonin carbohydrate residues retains ribosomal-inactivating properties of the toxin and permits targeting to folate receptor positive cells," Journal of Biological Chemistry, 2001; 276(30):27930-27935.
Attur, M. et al., "Differential anti-inflammatory effects of immunosuppressive drugs: Cyclosporin, rapamycin and FK-506 on inducible nitric oxide synthase, nitric oxide, cyclooxygenase-2 and $PGE_2$ production," Inflamm. res. 2000, 49, 020-026.
Ayers W.A., "Effect of Vitamin B12 and Analogs on the Respiration of a Marine Bacterium," *Archives of Biochemistry and Biophysics*, 1962, vol. 96, pp. 210-215.
Barnett C.J. et al., "Structure-Activity Relationships of Dimeric Catharanthus Alkaloids. 1. Deacetylvinblastine Amide (Vindesine) Sulfate," *J. Med. Chem.* 21: 88-96 (1978).
Bartels R. et al., "Determination of pteroic acid by high-performance thin-layer chromatography: Contribution to the investigation of 7,8-dihydropteroate synthase," *Journal of Chromatography A*, 1994; vol. 659(1): 185-189.
Bavetsias, V. et al., "Design and synthesis of Cyclopenta[g]quinazoline-based antifolates as inhibitors of thymidylate synthase and potential antitumor agents," J Med Chem, 2000; 43(10): 1910-1926.
Bavetsias, V., et al., "The design and synthesis of water-soluble analogues of CB30865, a quinazolin-4-one-based antitumor agent," J Med Chem, 2002; 45(17): 3692-3702.
Beaumont et al, Design of ester prodrugs to enhance oral absorption of poorly permeable compounds: Challenges to the Discovery Scientist, Current Drug Metbolism, 2003, 4, 461-485.
Beevers, Christopher S., et al., "Curcumin Inhibits the Mammalian Target of Rapamycin-Mediated Signaling Pathways in Cancer Cells", 2006; *Int. Journal Cancer*; Vo. 119; pp. 757-764.
Beil,L. "Is your breakfast giving you cancer," Prevention, updated Mar. 29, 2010, available via internet at http://www.nbcnews.com/id/35874922/ns/health-diet_and_nutrition/t/your-breakfast-giving-you-cancer/#.V40lrflVj2l.
Berendsen, A Glimpse of the Holy Grail?, Science, 1998, 282, pp. 642-643.
Berna M.J, Jensen R.T. Role of CCK/gastrin receptors in gastrointestinal/metabolic diseases and results of human studies using gastrin/CCK receptor agonists/antagonists in these diseases. Curf. Top Med Chem. 7:1211-1231, 2007.
Birinberg E. M. et al., "Synthesis and antimetabolic activity of pyrimidine analogs of folic and pteroic acids," *Pharmaceutical Chemistry Journal*, 1969; 3(6): pp. 331-333.
Bock et al., "Sulfonamide structure-activity relationships in a cell-free system. 2. Proof for the formation of a sulfonamide-containing folate analog," *Journal of Medical Chemistry*, 17: 23-28 (1974).
Boger, D.L. et al., "An improved synthesis of 1,2,9,9a-tetrahydrocyclopropa[c]benz[e]indol-4-one (CBI): a simplified analog of the CC-1065 alkylation subunit," *J. Org. Chem.*, 1992; 57: 2873-2876.

Boothe, J. H., et al., "Pteroic Acid Derivatives. II. Pteroyl-γ-glutamylglutamic Acid and Pteroyl-γ-glutamyl-γ-glutamylglutamic Acid," J. American Chem. Soc., vol. 70, 1948, pp. 1099-1102.
Bradley et al, Limits of Cooperativity in a Structurally Modular Protein: Response of the Notch Ankyrin Domain to Analogous Alanine Substitutions in Each Repeat, J. Mol. Biol, 2002, 324, pp. 373-386.
Brand SJ, Fuller PJ. Journal Biol. Chem. 263 5341-5347 1988.
Brown, Nicole E., et al., "Delayed Cystogenesis and Increased Ciliogenesis Associated with th Re-Expression of Polaris in Tg737 Mutant Mice", 2003, *Kidney International*, vol. 63, pp. 1220-1229.
Bukanov Nikolay, O. et al., "Long-Lasting Arrest of Murine Polycystic Kidney Disease With CDK Inhibitor Roscovitine", Dec. 14, 2006; *Nature*; vol. 444; pp. 949-952.
Campbell et al., "Folate-binding protein is a marker for ovarian cancer," *Cancer Res.*, 1991; 51: 5329-5338.
Caplin M, Savage K, Khan K, Brett B, Rode J, Varro A, and Dhillon A. Expression and processing of gastrin in pancreatic adenocarcinoma. Br J Surg. 87: 1035-1040,2000.
Carl et al. "A novel connector linkage applicable in prodrug design" J. Med. Chem. 1981;24(5):479-480.
Cerner Multum, Inc., Drugs.com, Folic Acid, http://www.drugs.com/folic_acid.html?printable=1, 1996-2014, Version: 5.01, Revision Date Oct. 15, 2009, pp. 104.
Chae et al, Recombinant Expression, Isotope labeling and purification of the Vitamin D Receptor Binding Peptide, Bull. Korean Chem Soc. 2011, 32, pp. 4337-4340.
Chao C, E. Goluszko, Y-T Lee, AA Kolokoltsov, RA Davey, T Uchida, CM Townsend Jr and MR Hellmich. Constitutively active CCK2 Receptor splice variant increases srcdependent HIF-1alpha expression and tumor growth. Oncogene 26, 1013-1019,2007.
Chao C, Kirk L. Ives, Elizabeth Goluszko, Andrey A Kolokoltsov, Robert A. Davey, Courtney M. Townsend Jr and Mark R. Hellmich. Src Regulates constitutive internalization and rapid resensitization of a Cholecystokinin 2 receptor splice variant. Journal of Biological Chemistry 280 (39)33368-33373, 2005.
Cho et al., "Single-chain Fv/folate conjugates mediate efficient lysis of folate-receptor-positive tumor cells," *Bioconjug. Chem.* 8(3): 338-346 (1997).
Christensen et al., "Membrane receptors for endocytosis in the renal proximal tubule," *Int. Rev. Cytol.*, 1998; 180: 237-284.
Churlaud C. et al., "Novel 4-(Trimethylsilyl)aminoalkanes and 4-(Trimethylsilyl)aminoalk-2-enes, via a 1,5-Hydride Shift, in the Reaction of α-Unsaturated Silanes with Aminomethylbenzotriazoles," *Organomettalics*, 1999; 18(21): 4270-4274.
Citro G. et al., "Inhibition of leukemia cell proliferation by folic acid-polylysine-mediated introduction of c-myb antisense oligodeoxynucelotides into HL-60 cells," *Br. J. Cancer*, 1994; 69: 463-467.
Coney et al. "Cloning of a tumor-associated antigent: MOv18 and MOv19 antibodies recognize a folate-binding protein" Cancer Res. 1991;51(22):6125-32.
Conrad et al, Journal of Medicinal Chemistry, 1979, 22(4): 391-400.
Cope A.C. et al., "Thermal Rearrangement of Allyl-type Sulfoxides, Sulfones and Sulfinates," *J. Am. Chem. Soc.*, 1950; 72; 59-67.
Cosulich D.B. et al., "Analogs of Pteroylglutamic Acid. I. N10-Alkylpteroic Acid and Derivatives," *JACS*, 1948, 70 (5), pp. 1922-1926.
Crapatureanu et al. "Molecular necklaces. Cross-linking hemoglobin with reagents containing covalently attached ligands" Bioconjugate Chemistry, 1999;10(6):1058-67. Abstract Only.
Currutto G. A chemical method for the preparation of novel 1,5 benzodiazepines acting as CCK-B Antagonists in high enantiomeric purity. Tetrahedron 53 (21) 7347-7364 1997.
Darnell, Ed. Molecular Cell Biology W. H. Freeman, San Francisco 1990;326-333.
Definition of derivative and analog, from http://cancerweb.ncl.ac.uk/cgi-omd?query=derivative and http://cancerweb.ncl.ac.uk/cgi-bin/omd?query=analog, pp. 1-5, accessed Jul. 7, 2005.
Definition of moiety, from http://dictionary.reference.com/browse/moiety, pp. 1-3, accessed Aug. 26, 2010.

(56) References Cited

OTHER PUBLICATIONS

DeNardo, Gerald. "When is Too Much Too Much and Yet Not Enough? Alas, a Plethora of Opportunities but Where's the Beef?" J. of Nuclear Medicine 2000; 41(3):470-3.

Domling A. et al., "Myxobacterial Epothilones and Tubulysins as Promising Anticancer Agents," *Molecular Diversity*, 2005; 9: 141-147.

Dong, H. et al., "Self-assembled, redox-sensitive, H-shaped pegylated methotrexate conjugates with high drug-carrying capability for intracellular drug delivery," Med. CHem. Commun., 2013, 5, 147-152.

Dorwald, F. Z., "Side Reactions in Organic Synthesis: A Guide to Successful Synthesis Design," Wiley-VCH, Weinheim, 2005, p. ix of preface.

Douglas J.T. et al., "Targeted Gene Delivery by Tropism-Modified Adenoviral Vectors," *Nat. Biotechnol.*, 1996, vol. 14, pp. 1574-1578.

Dube D et al., "Preparation and Tumor Cell Uptake of Poly(N-isopropylacrylamide) Folate Conjugates"; *Bioconjugate Chem*, 2002; 13: 685-692.

Dufresne et al., Cholecystokinin and gastrin receptors. Physiol Rev. 86:805-847,2006.

Dyson G., May P. "The Chemistry of Synthetic Pharmaceutical Substances", translation from English M.:—"The World", 1964, pp. 12-19.

Eichman, J.D. et al., "The Use of PAMAM Dendrimers in the Efficient Transfer of Genetic Material Into Cells", Jul. 2000, *PSTT*, vol. 3, No. 7, pp. 232-245.

Elnakat et al., "Distribution, functionality and gene regulation of folate receptor isoforms: implications in targeted therapy," Advanced Drug Delivery Reviews, 2004; vol. 56:1067-84.

Endocyte: Endocyte Enrolls First Patient in Phase 1 Study for the Small Molecule Drug Conjugate EC1456, a Folate-Targeted Tubulysin Conjugate in Advanced Solid Tumors. Dec. 2013. [Retrieved on May 6, 2015).

Ettmayer et al, Lessons learned from marketed and investigational prodrugs, J. Med Chem, 2004, 47(10), pp. 2393-2404.

European Search Report prepared for corresponding European Application Serial No. 08841521.1, dated Jul. 18, 2011.

Evans et al., "Synthessis of biotin conjugates of the antifungal compound cymoxanil," *Pest Manag Sci*, 2002; 58: 392-396.

Ferrand A., Timothy C. Wang. Gastrin and Cancer. Cancer Letters 238(1): 15-29,2006.

Foong, L.Y. et al., "Development of a Novel Thiol Reagent for Probing Ion Channel Structure: Studies in a Model System," *Biochemistry*, 1997, vol. 36, pp. 1343-1348.

Forgac. "Structure and function of vacuolar class of ATP-driven pumps" Physiological Rev. 1989; 69(3) :765-795.

Frankel AE., "Immunotoxin therapy of cancer," *Oncology*, 1993; 7(5): 69-78.

Gabizon et al., "Tumor cell targeting of liposome-entrapped drugs with phospholipid-anchored folic acid-PEG Conjugates," Advanced Drug Delivery Reviews, 2004; vol. 56: 1177-92.

Gabizon et al., Clin Cancer Res 9:6551-59 (2003).

Gangjee et al., "The effect of 5-alkyl modification on the biological activity of pyrrolo[2,3-d]pyrimidine containing classical and non-classical antifolates as inhibitors of dihydrofolate reductase and as antitumor and/or antiopportunistic infection agents," *J Med Chem.*, 2008; 51(15):4589-4600.

Garin-Chesa et al., "Trophoblast and ovarian cancer antigen LK26. Sensitivity and specificity in immunopathology and molecular identification as a folate-binding protein," *Am. J. Pathol.* 142(2): 557-562 (1993).

Garrett et al. "Synthesis and characterisation of polyamine-poly(ethylene glycol) constructs for DNA binding and gene delivery" Bioorganic & Medicinal Chemistry, 2000; 8(7):1779-1797. Abstract Only.

GE Healthcare, Instructions 71-7104-00 AD (1993).

Gibbs, DD et al., "BGC 945, a novel tumor-selective thymidylate synthase inhibitor targeted to alpha-folate receptor-overexpressing tumors," Cancer Res, 2005; 65(24): 11721-11728.

Golub, T.R., et al., "Molecular Classification of Cancer: Class Discovery and Class Prediction by Gene Expression Monitoring," Science, 1999, vol. 286, 531-537 (Oct. 15, 1999).

Gottschalk S. et al., "Folate receptor mediated DNA delivery into tumor cells: potosomal disruption results in enhanced gene expression," *Gene Therapy*, 1994; 1(3): 185-191.

Grabowska et al., "Pre-clinical evaluation of a new orally-active CCK-2R antagonist, Z-360, in gastrointestinal cancer models," Regulatory Peptides, 14646-57 (2008).

Griesser UJ, "The Importance of Solvates," in Polymorphism in the Pharmaceutical Industry, Hilfiker ed., 2006; p. 211-230.

Han, Hyo-Kyung, "Targeted prodrug design to optimize drug delivery," AAPS Pharmsci 2000, 2(10), article 6, p. 1-11.

Hanck A.B. et al., "Dexpanthenol (Ro 01-4709) in the treatment of constipation," *Acta Vitaminol Enzymol*, 1982; vol. 4 (1-2), pp. 87-97 (abstract only).

Harrison JG et al., A convenient synthetic route to oligonucleotide conjugates,: Bioorganic & Medicinal Chemistry Letters, 1997; 7(8): 1041-1046.

Harvison, P.J. et al., "Synthesis and Biological Activity of Novel Folic Acid Analogues: Pteroyl-S-alkylhomocysteine Sulfoximines," *Journal of Medicinal Chemistry*, 1992, vol. 35, pp. 1227-1233.

Hay, Nissim, et al., "Upstream and Downstream of mTOR", 2004, *Genes & Development*, vol. 18, No. 16, pp. 1926-1945.

Hellmich MR, Rui XL, Fleming RY, Evers BM, Townsend Jr CM Human colorectal cancers express a constitutively active Cholecystokinin-BI gastrin receptor that stimulates cell growth. J. Biol. Chern 275,32122-32128,2000.

Henderson et al. "Mediated uptake of folate by a high-affinity binding protein in sublines of L1210 cells adapted to nanomolar concentrations of folate" J. Membrane Biol., 1988;101:247-258.

Henderson, E.A. et al., Targeting the alpha-folate receptor with cyclopenta[g]quinazoline-based inhibitors of thymidylate synthase, Bioorg Med Chem, 2006; 14(14): 5020-5042.

Henne, et al., "Synthesis and activity of a folate peptide camptothecin prodrug," ScienceDirect, Bioorganic & Medical Chemistry Letters 16 (2006) 5350-5355.

Ho R. I. et al., "A simple radioassay for dihydrofolate synthetase activity in *Escherichia coli* and its application to an inhibition study of new pteroate analogs," *Anal. Biochem.*, 1976, 73(2), pp. 493-500.

Hofland et al., "Folate-targeted gene transfer in vivo," *Mol Ther* 5(6): 739-744 (2002).

Hofle, G. et al., "Semisynthesis and Degradation of the Tubulin Inhibitors Epothilone and Tubulysin", 2003, *Pure Appl. Chem.*, vol. 75, Nos. 2-3, pp. 167-178.

Holladay et al., "Riboflavin-mediated delivery of a macromolecule into cultured human cells," *Biochim Biophys Acta*, 1426(1): 195-204 (1999).

Holm, J. et al., "Folate receptors in malignant and benign tissues of human female genital tract," *BioSci. Rep.*, 17(4): 415-427 (1997).

Holm, J. et al., "High-affinity folate binding in human choroid plexus. Characterization of radioligand binding, immunoreactivity, molecular heterogeneity and hydrophobic domain of the binding protein," *Biochem J.*, 280(1): 267-271 (1991).

Hosomi A. et al., "Affinity for a-tocopherol transfer protein as a determinant of the biological activities of vitamin E analogs," *Federation of European Biochemical Societies Letters*, 1997, vol. 409, pp. 105-108.

Houlihan, C. M. et al., "Preparation and Purification of Pteroic Acid from Folic Acid," *Analytical Biochemistry*, 1972, vol. 46, pp. 1-6.

Huang et al. "Design, syntheses and sequence selective DNA cleavage of functional models of bleomycin-II. 1,2-trans-di substituted cyclopropane units as novel linkers" Bioorganic & Medicinal Chemistry, 1995;3(6):647-57. Abstract Only.

Hur K, Kwak MK, Lee HJ, Park DJ, Lee HK, Lee HS, Kim WH, Michaeli D, Yang HK. Expression of gastrin and its receptor in human gastric cancer tissues. 2, Feb. J Cancer Res Clin Oncol., vol. 132, pp. 85-91, 2006.

(56) References Cited

OTHER PUBLICATIONS

Hynes et al., "Quinazolines as inhibitors of dihydrofolate reductase. 4. Classical analogues of folic and isofolic acids", *Journal of Medical Chemistry*, 1977; 20: 588-591.
Jackman, A. L. et al., "Antifolates targeted specifically to the folate receptor," Adv Drug Deliv Rev, 2004; 56(8): 1111-1125.
Jansen et al. "The Reduced Folate/Methotrexate Carrier and a Membrane-Associated Folate Binding Protein as Transport Routes for Novel Antifolates: Structure-Activity Relationship" Chemistry and Biology of Pteridines and Folates New York, 1992;767-770.
Jansen et al., "Identification of a Membrane-Associated Folate-Binding Protein in Human Leukemic CCRF-CEM Cells with Transport-Related Methotrexate Resistance"0 in Cancer Res., 1989, 49, 2455-2459.
Jansen, "Receptor- and Carrier-Mediated Transport Systems for Folates and Antifolates," Antifolate Drugs in Cancer Therapy, Jackman, Ed., Humana Press Inc, Totowa NJ (1999): 293-321.
Jones T.R. et al., "A potent antitumour quinazoline inhibitor of thymidylate synthetase: synthesis, biological properties and therapeutic results in mice," *Eur J Cancer*, 1981; 17(1):11-9.
Jones T.R. et al., "Quinazoline antifolates inhibiting thymidylate synthase: variation of the amino acid," *J Med Chem*, 1986; 29(6):1114-8.
Jung K.H. et al., "Intramolecular o-glycoside bond formation," *Chem. Rev.*, 2000, 100, 4423-42.
Kagechika H et al., "Synthetic Retinoids: Recent Developments Concerning Structure and Clinical Utility," *Journal of Medicinal Chemistry*, 2005; vol. 48, No. 19, pp. 5875-5883.
Kamao M. et al., "Determination of Plasma Vitamin K by High Performance Liquid Chromatography with Fluorescence Detection Using Vitamin K Analogs as Internal Standards," *Journal of Chromatography B*, 2005; vol. 816, pp. 41-48.
Kamen et al., "A review of folate receptor alpha cycling and 5-methyltetrahydrofolate accumulation with an emphasis on cell models in vitro," Advanced Drug Delivery Reviews, 2004; vol. 56:1085-97.
Kamen et al., "Delivery of folates to the cytoplasm fo MA104 cells is mediated by a surface receptor that recycles," *J. Biol. Chem.*, 263: 13602-13609 (1988).
Kamen et al., "The folate receptor works in tandem with a probenecid-sensitive carrier in MA104 cells in vitro," *J. Clin. Invest.*, 87(4): 1442-1449 (1991).
Kamen, B. A. et al., "Receptor-mediated folate accumulation is regulated by the cellular folate content," *Proc. Natl. Acad. Sci. USA*, 83: 5983-5987 (1986).
Kandiko C.T. et al., "Inhibition of Rat Brain Pyruvate Dehydrogenase by Thiamine Analogs," *Biochemical Pharmacology*, 1988; vol. 37, No. 22, pp. 4375-4380.
Kane et al., "The influence of extracellular folate concentration on methotrexate uptake by human KB cells. Partial characterization of a membrane-associated methotrexate binding protein," *J. Biol. Chem.*, 261: 44-49 (1986).
Kaneko, Takushi, "New Hydrazone Derivatives of Adiramycin and their Immunoconjugates—A Correlation between Acid Stability and Cytotoxicity", *Bioconj. Chem.*, vol. 2, No. 3, pp. 131-141 (May 1, 1991).
Kawasaki D., Emori Y., Eta R., Iino Y., Hamano H., Yoshinaga K., Tanaka T., Takei M., and Watson S.A. Effect of Z-360, a novel orally active CCK-2/gastrin receptor antagonist on tumor growth in human pancreatic adenocarcinoma cell lines in vivo and mode of action determinations in vitro. Cancer Chemother. Pharmacol. 61(5): Apr. 2008.
Ke CY et al., "Folate-Receptor-Targeting of In-111 Using Pteroic Acid Conjugates of Benzyl-DTPA and Benzyl-DOTA," J. Nucl. Med., 2004; 45(5):457P.
Ke et al. "Targeting the Tumor-Associated Folate Receptor with a I IN-DTPA Conjugate of Pteroic Acid" Abstract No. 427. 48'h Annual Meeting of the Society of Nuclear Medicine Toronto, Canada, Jun. 26, 2001, available May 4, 2001; 1 pg.

Ke et al., "Folate-receptor-targeted radionuclide imaging agents," Advanced Drug Delivery Reviews, 2004; vol. 56: 1143-60.
Kemp et al. "New Protective Groups for Peptide Synthesis-I the Bic Group Base and Solvent Lability of the 5-B enzi soxazolymethyl eneoxycarbonyl amino function" Tet. Lett. 1975;52:4625-4628.
Kennedy, Michael D., et al., "Evaluation of Folate Conjugate Uptake and Transport by the Choroid Plexus of Mice", (May 2003), vol. 20, No. 5, pp. 714-719.
Kilonda et al., "The Synthesis of 7-carbonyl homolgues of 1-deoxynojirimycin," Tetrahedron Letters (1994) 35(48): 9047-9050.
Kim et al., "Synthesis and biological activity of 10-thia-10-deaza analogs of folic acid, pteroic acid, and related compounds", *Journal of Medical Chemistry*, 18: 776-780 (1975).
Kobayashi et al., "Z-360, a novel Cholecystokinin-2/gastlin receptor antagonist, inhibits Gemcitabine induced expression of the vascular endothelial growth factor gene in human pancreatic cancer cells," Biol.Pharm. Bull. 33 (2) 216-222 (2010).
Korner et al., "CCK(2) receptor splice variant with intron 4 retention in human gastrointestinal and lung tumours," Apr. 2010, J Cell Mol Med. , vol. 14, pp. 933-943.
Kranz et al., "Conjugates of folate and anti-T-cell-receptor antibodies specifically target folate-receptor-positive tumor cells for lysis," *Proc. Natl. Acad. Sci. USA*, 1995; 92(20), pp. 9057-9061.
Kumar H.P. et al., "Folate transport in Lactobacillus salivarius. Characterization of the transport mechanism and purification and properties of the binding component," *J. Biol. Chem..* 1987; 262(15):7171-7179.
Kutsky RJ. Handbook of Vitamins, Minerals, and Hormones, 2nd Edition. New York: Van Nostrand Reinhold: 1981;263-277.
Ladino et al., "Folate-maytansinoids: target-selective drugs of low molecular weight," *Int. J. Cancer*, 73(6): 859 864 (1997).
Lambooy J. P., "Riboflavin Analogs Utilized for Metabolism by a Lactobacillus Casei Mutant," *Int. J. Biochem.*, vol. 16, No. 2, 1984, pp. 231-234.
Landuer W. et al., "The Interaction in Teratogenic Activity of the Two Niacin Analogs 3-acetylpyridine and 6-aminonicotinamide," *J Exp Zool*, 151(3):253-258 (1962).
Langone, J.J., et al., "Radioimmunoassays for the Vinca Alkaloids, Vinblastine and Vincristine", 1979, *Analytical Biochemistry*, No. 95, pp. 214-221.
Laplanche, et al.,"Physiologically Based Pharmacokinetic (PBPK) Modeling of Everolimus (RAD001) in Rats Involving Non-Linear Tissue Uptake," Journal of Pharmacokinetics and Pharmacodynamics, 2007, vol. 34, No. 3, 373-400.
Lauffer D.J., Mullican M.D., A practical synthesis of (S) 3-tert-Butoxycarbonylamino-2-oxo-2,3,4,5-tetrahydro-1,5-benzodiazepine-l-acetic acid methyl ester as a conformationally restricted dipeptide-Mimetic for caspase-1 (ICE) inhibitors. Biorganic and Medicinal Chem. Lett. 12(8) 1225-1227, 2002.
Leamon Christopher P., "Aspects of Folate-Mediated Drug Delivery . . . Beyond Purdue" PowerPoint Presentation presented at Purdue University on May 4, 1999, (22 pages).
Leamon CP et al, "Cytotoxicity of folate-Pseudomonas exotoxin conjugates toward tumor cells. Contribution of translocation domain," *J. Biol. Chem.* 268(33): 24847-24854 (1993).
Leamon CP et al., "Comparative Preclinical Activity of the Folate-targeted Vinca Alkaloid Conjugates EC140 and EC145," *Int J Cancer*, 2007; 121(7):1585-92.
Leamon CP et al., "Cytotoxicity of momordin-folate conjugates in cultured human cells," *J. Biol. Chem.*, 1992; 267(35): 24966-24971.
Leamon CP et al., "Delivery of macromolecules into living cells: a method that exploits folate receptor endocytosis," *Proc. Natl. Acad. Sci. USA* 88(13): 5572-5573 (1991).
Leamon CP et al., "Folate-mediated targeting: from diagnostics to drug and gene delivery," *Drug Discovery Today* 6: 44-51 (2001).
Leamon CP et al., "Folate-targeted chemotherapy," Adv Drug Deliv Rev, 2004;56(8): 1127-41.
Leamon CP et al., "Membrane folate-binding proteins are responsible for folate-protein conjugate endocytosis into cultured cells," *Biochem. J.* 291: 855-860 (1993).
Leamon CP et al., "Selective targeting of malignant cells with cytotoxin-folate conjugates," *J. Drug Target.* 2(2): 101-112 (1994).

(56) References Cited

OTHER PUBLICATIONS

Leamon CP et al., "Synthesis and biological evaluation of EC140: A novel folate-targeted vinca alkaloid conjugate," Bioconjug Chem, 2006;17(5):1226-32.
Leamon CP et al., "Synthesis and Biological Evaluation of EC20: A New Folate-Derived, (99m)Tc-Based Radiopharmaceutical," Bioconjug. Chem. 13(6): 1200-1210 (2002).
Leamon CP et al., "Synthesis and biological evaluation of EC72: a new folate-targeted chemotherapeutic," Bioconjug Chem., 2005;16(4):803-11.
Leamon et al., "Folate Receptor specific anti-tumor activity of EC0305, a folate-tubulysin conjugate," AACR Annual Meeting, 2007, 67, 9, (abstract only).
Leamon et al., "Folate-mediated drug delivery: effect of alternative conjugation chemistry," J. Drug Target 7(3): 157-169 (1999).
Leamon, Christopher P., et al., "Folate-Liposome-Mediated Antisense Oligodeoxynucleotide Targeting to Cancer Cells: Evaluation in Vitro and in Vivo", 2003, Bioconjugate Chemistry, vol. 14, No. 4, pp. 738-747.
Leamon, et al., "Patient selection and targeted treatment in the management of platinum-resistant ovarian cancer," Pharmacogenomics and Personalized Medicine, 6:113-125 (2013).
Lee et al, "Measurement of Endosome pH Following Folate Receptor-Mediated Endocytosis," Biochim. Biophys. Acta 1312(3): 237-242 (1996).
Lee et al. "Prolonged circulating lives of single-chain Fv proteins conjugated with polyethylene glycol: a comparison of conjugation chemistries and compounds" Bioconjugate Chemistry, 1999;10(6):973-81. Abstract Only.
Lee et al., "The Human Cholecystokinin-BI Gastrin Receptor," Journal of Biological Chemistry 268 (11) 8164-8169, 1993.
Lee et al., "Synthesis and evaluation of taxol-folic acid conjugates as targeted antineoplastics," Bioorg Med Chem. 10(7): 2397-2414, (2002).
Lee JW et al., "Reduction of azides to primary amines in substrates bearing labile ester functionality. Synthesis of a PEG-solubilized, "Y"-shaped iminodiacetic acid reagent for preparation of folate-tethered drugs," Organic Letters, 1999; 1(2):179-181.
Lee W.W. et al., "Folic acid antagonists. Methotrexate analogs containing spurious amino acids. Dichlorohomofolic acid," Journal of Medical Chemistry, 17: 326-330 (1974).
Lee, Francis Y. F., et al., "BMS-247550: A Novel Epothilone Analog With a Mode of Action Similar to Paclitaxel But Possessing Superior Antitumor Efficacy," Clin Cancer Res, 2001, No. 7, pp. 1429-1437.
Lee, R. J. and Huang, L., "Folate-Targeted, Anionic Liposome-Entrapped Polylysine-Condensed Dna for Tumor Cell-Specific Gene Transfer," J. Biol. Chem. 271(14): 8481-8487 (1996).
Lee, R. J. and Low, P. S, "Delivery of liposomes into cultured KB cells via folate receptor-mediated endocytosis," J. Biol. Chem. 269(5): 3198-3204 (1994).
Lee, R. J. and Low, P. S., "Folate-mediated tumor cell targeting of liposome-entrapped doxorubicin in vitro," Biochim. Biophys. Acta 1233: 134-144 (1995).
Lemon, Julia, et al., "Conversion of Pterolyglutamic Acid to Pteroic Acid by Bacterial Degradation," Archives of Biochemistry, 1948; vol. 19, pp. 311-316.
Levy, Carl C., et al. "The Enzymatic Hydrolysis of Methotrexate and Folic Acid", 1967, The Journal of Biological Chemistry, vol. 242, No. 12, pp. 2933-2938.
Lewis et al., "Receptor-mediated folate uptake is positively regulated by disruption of actin cytoskeleton," Cancer Res. 58(14): 2952-2956 (1998).
Li et al, "Targeted delivery of antisense oligodeoxynucleotides by LPDII," J. Liposome Res. 7(1): 63 (1997).
Li et al. "Local concentration of folate binding protein GP38 in sections of human ovarian carcinoma by concentration of in vitro quantitative autoradiography." J. Nucl. Med. 1996; 37:665-672.

Linder et al., In vitro & in vivo studies with a-and y-isomers of 99'Tc-oxa folate show uptake of both isomers in folate receipt (+) KB Cell Lines J. Nuclear Med. 2000;41(5):470 Suppl.
Lindstedt, E.W. et al.; "Anti-tnf-alpha therapy for sight threatening uveitis." Br. J. Opthalmol. (2005) 89 p. 533-536.
Liu et al., "Targeted Drug Delivery to Chemoresistant Cells: Folic Acid Derivatization of FdUMP[10] Enhances Cytotoxicity Toward 5-FU-Resistant Human Colorectal Tumor Cells," J. Org. Chem. 66: 5655-5663 (2001).
Lonsdale D, "A Review of the Biochemistry, Metabolism and Clinical Benefits of Thiamin(e) and Its Derivatives," publication, Advance Access Publication, vol. 3, Feb. 2006, pp. 49-59.
Lopes et al., "Acyloxymethyl as a drug protecting group. Part 5.1 Kinetics and mechanism of the hydrolysis of tertiary N-acyloxymethylsulfonamides," J. Chem. Soc., Perkin Trans. 2, pp. 431-439 (1999).
Lorusso, P. M. et al., "Phase I Study of Folate Conjugate EC145 (Vintafolide) in Patients with Refractory Solid Tumors," J. Clinical Oncology, 2012, 30, No. 32, 4011-4016.
Low P.S. et al., "Folate Receptor-Targeted Drugs for Cancer and Inflammatory Diseases," Adv Drug Deliv Rev, 2004;56(8):1055-238 (should this be 1055-1058?).
Lu et al., "Folate receptor-targeted immunotherapy of cancer: mechanism and therapeutic potential," Advanced Drug Delivery Reviews, 2004; vol. 56: 1161-76.
Lu et al., "Folate-targeted enzyme prodrug cancer therapy utilizing penicillin-V amidase and a doxorubicin prodrug," J. Drug Target, 7(1): 43-53 (1999).
Lu, J. Y. and Low, P. S., "Folate targeting of haptens to cancer cell surfaces mediates immunotherapy of syngeneic murine tumors," Cancer Immunol Immunother, 51: 153-162 (2002).
Lu, J. Y. and Low, P. S., "Folate-mediated delivery of macromolecular anticancer therapeutic agents," Adv. Drug Del Rev, 2002; 54(5): 675-693.
Luo et al., "Efficient syntheses of pyrofolic acid and pteroyl azide, reagents for the production of carboxyl-differentiated derivatives of folic acid," J. Am. Chem. Soc., 119: 10004-10013 (1997).
Machine Translation of WO 2004/005326, Jan. 15, 2004, pp. 1-5.
Mack D.O. et al., "The Carboxylation Activity of Vitamin K Analogs with Substitutions at Position 2, 3, or 5," Journal of Biological Chemistry, 1979; vol. 254, pp. 2656-2664.
Mancuso A.J. et al., "Activated Dimethyl Sulfoxide: Useful Reagents for Synthesis," Synthesis, 1981, pp. 165-184.
Mengel, Andreas: GMP news, 2002, www.gmp-compliance.ord/eca_news_159.html, downloaded Mar. 19, 2014.
March, Advanced Organic Chemistry, 1992, John Wiley & Sons, 4th Ed., pp. 362-363, 816, 885, 896.
Mashkovskiy M.D. Drugs, Moscow, New wave, 2001, vol. I, p. 11.
Mathais et al., "Receptor-mediated targeting of 67Ga-deferoxamine-folate to folate-receptor-positive human KB tumor xenografts," Nucl Med Biol, 26(1): 23-25 (1999).
Mathais et al., "Synthesis of [(99m)Tc]DTPA-folate and its evaluation as a folate-receptor-targeted radiopharmaceutical," Bioconjug Chem, 11(2): 253-257 (2000).
Mathias et al., "Indium-111-DTPA-Folate as a potential folate-receptor-targeted radiopharmaceutical," J. Nucl. Med., 39(9): 1579-1585 (1998).
Mathias et al., "Tumor-Selective Radiopharmaceutical Targeting Via Receptor-Mediated Endocytosis of Gallium-67-Deferoxamine-Folate," J. Nucl. Med, 37(6): 1003-1008 (1996).
Mathias, C. J., "A kit formulation for preparation of [(111)In]In-DTPA-folate, a folate-receptor-targeted radiopharmaceutical," Nucl. Med. Biol., 25(6): 585-587 (1998).
Matsui et al., "Studies on mitomycins. III. The synthesis and properties of mitomycin derivatives," J Antibiot, 21: 189-198 (1968).
Matulic-Adamic J et al., "An efficient synthesis of the ribozyme-folate conjugate," Tetrahedron Letters, 2002; 43(25):4439-4441.
McAlinden TP et al., "Synthesis and Biological Evaluation of a Fluorescent Analogue of Folic Acid," Biochemistry, 1991; 30: 5674-81.
McHugh M et al., "Demonstration of a High Affinity Folate Binder in Human Cell Membranes and Its Characterization in Cultured Human KB Cells," J Biol Chem, 1979; 254(22):11312-8.

(56) References Cited

OTHER PUBLICATIONS

Mehvar R "Dextrans for targeted and sustained delivery of therapeutic and imaging agents" [Review] Journal of Controlled Release, 2000;69(1):1-25. Abstract Only.

Melani et al., "Targeting of interleukin 2 to human ovarian carcinoma by fusion with a single-chain Fv of antifolate receptor antibody," Cancer Res. 58(18): 4146-4154 (1998).

Melby, E.L. et al, "Entry of Protein Toxins in Polarized Epithelial Cells"; Cancer Research, 1993; 53: 1755-1760.

Mezzanzanica et al. "Human T-lymphocytes targeted against an established human ovarian carcinoma with a bispecific F(ab')2 antibody prolong host survival in a murine xenograft model" Cancer Res. 1991; 51:5716-5721.

Miller L.J. Does the Human Pancreas have a type A or B personality? Gastroenterology 111, 1767-1770,1996.

Miotti et al., "Characterization of Human Ovarian Carcinoma-Associated Antigens Defined by Novel Monoclonal Antibodies with Tumor-Restricted Specificity" Int. J. Cancer, 1987;39:297-303.

Mislick et al., "Transfection of folate-polylysine DNA complexes: evidence for lysosomal delivery," Bioconjug. Chem.6(5): 512-515 (1995).

Mock D.M. et al., "Urinary Biotin Analogs Increase in Humans During Chronic Supplementation: the Analogs are Biotin Metabolites," Am J Physiol Endocrinol Metab, 1997; 272: E83-E85.

Monstein et al., "Cholecystokinin A and Cholecystokinin-B/Gastrin receptor mRNA expression in the gastrointestinal tract and pancreas of the rat and human. A polymerase chain reaction study," Scand J Gastroenterol 31383-390, 1996.

Morshed et al., "Folate transport proteins mediate the bidirectional transport of 5-methyltetrahydrofolate in cultured human proximal tubule cells," J. Nutr., 127(6): 1137-1147 (1997).

Muller, Prodrug approaches for Enhancing the Bioavailability of Drugs with Low Solubility, Chemistry & Biodiversity, 2009, 6, pp. 2071-2083.

Na, Wang, and Kohn, "7-N-(Mercaptoalkyl)mitomycins: Implications of Cyclization for Drug Function," J Am Chem Soc 124:4666-77 (2002.

Nair et al., "Folate analogs altered in the C9-N10 bridge region. 14. 11-Oxahomofolic acid, a potential antitumor agent", Journal of Medical Chemistry, 23: 59-65 (1980).

Nair et al., "Folate analogs altered in the C9-N10 bridge region. 18. Synthesis and antitumor evaluation of 11-oxahomoaminopterin and related compounds," Journal of Medical Chemistry, 24: 1068-1073 (1981).

Nair et al., "Folate analogs altered in the C9-N10 bridge region: N10-tosylisohomofolic acid and N10-tosylisohomoaminopterin," Journal of Medical Chemistry, 21: 673-677 (1978).

Nair et al., "Folate analogs altered in the C9-N10 bridge region: 11-thiohomofolic acid," Journal of Medical Chemistry, 22: 850-855 (1979).

Nair et al., "Folate analogs. 20. Synthesis and antifolate activity of 1',2',3',4',5',6'-hexahydrohomofolic acid," Journal of Medical Chemistry, 26: 135-140 (1983).

Nair et al., "Folate analogs. 21. Synthesis and antifolate and antitumor activities of N10-(cyanomethyl)-5,8-dideazafolic acid," Journal of Medical Chemistry, 26: 605-607 (1983).

Nair et al., "Folate analogs. 22. Synthesis and biological evaluation of two analogs of dihydrofolic acid possessing a 7,8-dihydro-8-oxapterin ring system," Journal of Medical Chemistry, 26: 1164-1168 (1983).

Nair et al., "Folate analogues altered in the C9-N10 bridge region. 10-Oxafolic acid and 10-oxaaminopterin," Journal of Medical Chemistry, 19: 825-829 (1976).

Nauta, Jeroen, et al., "Renal and Biliary Abnormalities in a New Murine Model of Autosomal Recessive Polycystic Kidney Disease", 1993, Pediatr. Nephrol. No. 7, pp. 163-172.

Neuss, N. et al., "Vinca Alkaloids. XXX (1). Chemistry of the Deoxyvinblastines (Deoxy-VLB), Leurosine (VLR), and Pleurosine, Dimeric Alkaloids From Vinca," Tetrahedron Letters, No. 7, pp. 783-787 (1968).

Neuzil J. et al., "Vitamin E Analogs: A New Class of Multiple Action Agents with Anti-Neoplastic and Anti-Atherogenic Activity," Apoptosis, 2002; vol. 7, pp. 179-187.

Ngo et al, Computational Complexity, Protein Structure protection, and the Levinthal Paradox, 1994, pp. 491-497.

Nielsen P. et al., "Phosphates of Riboflavin and Riboflavin Analogs: A Reinvestigation by High-Performance Liquid Chromatography," Analytical Biochemistry, vol. 130, 1983, pp. 359-368.

Nimmo-Smith R.N. et al., "Some Effects of 2-deaminopteroylglutamic Acid upon Bacterial Growth," J. Gen. Microbial., 1953; 9: 536-544.

NIOSH List of antineoplastic and Other Hazardous Drugs in Healthcare settings 2010, pp. 1-16, published Sep. 20, 2010.

Nishikawa, Yuji et al., "Growth Inhibition of Hepatoma Cells Induced by Vitamin K and Its Analogs," Journal of Biological Chemistry, 1995; vol. 270, No. 47, pp. 28304-28310.

Nomura, Makoto et al., "Development of an Efficient Intermediate a-[2-(Trimethylsilyl)ethoxy]-2-N-[2-(trimethylsilyl)ethoxycarbonyl]folic Acid, for the Synthesis of Folate (y)-Conjugates, and Its Application to the Synthesis of Folate-Nucleoside Congugates," Journal of Organic Chemistry, 2000, vol. 65, pp. 5016-5021.

Nosaka K.et al., "Separate Determination of Anticoccidial Thiamine Analogs by High-performance Liquid Chromatography," ActaA Vitaminol. Et Enzymol, 1984, vol. 6 (2), pp. 137-142.

Oatis et al., "Synthesis of quinazoline analogues of folic acid modified at position 10," Journal of Medical Chemistry, 20: 1393-1396 (1977).

Olsnes S. et al., "Immunotoxins-entry into cells and mechanisms of action," Immunology Today, 1989; vol. 10, No. 9, pp. 291-295.

Olszewska-Pazdrak B, Townsend CM Jr, Hellmich MR. Agonist-independent activation of Src tyrosine kinase by a cholecystokinin-2 (CCK2) receptor splice variant39, Sep. 24, 2004, J Biol Chern., vol. 279, pp. 40400-40404.

Paranjpe, et al., "Tumor-targeted bioconjugate based delivery of camptothecin: design, synthesis and in vitro evaluation," ScienceDirect Journal of Controlled Release 100 (2004) 275-292.

Parker et al., "Folate receptor expression in carcinomas and normal tissues determined by a quantitative radioligand binding assay," Analytical Biochemistry, 2005; 335:284-293.

Pastan et al, eds. "The Pathways of Endocytosis" Endocytosis, Plenum Press, New York 1985;1-40.

Pathalk et al., Enzymic protecting group techniques in organic synthesis, Stereosel. Biocatal. 775-797 (2000).

Patrick et al., "Folate Receptors As Potential Therapeutic Targets in Choroid Plexus Tumors of Sv40 Transgenic Mice," J. Neurooncol,. 32(2): 111-123 (1997).

Patrick et al., "Intracerebral bispecific ligand-antibody conjugate increases survival of animals bearing endogenously arising brain tumors," Int. J. Cancer, 78(4): 470-79 (1998).

Patterson et al., "Design, synthesis, and biological properties of highly potent tubulysin D analogues," Chemistry—A European Journal, 2007; 13(34): 9534-9541.

Patterson et al., "Expedient synthesis of N-Methyl tubulysin analogues with high cytotoxicity," Journal of Organic Chemistry, 2008; 73:4365-4369.

Paulos CM et al., "Ligand Binding and Kinetics of Folate Receptor Recycling in Vivo: Impact on Receptor-Mediated Drug Delivery," Molecular Pharmacology, 2004; 66:1406-1414.

Paulos et al., "Folate receptor-mediated targeting of therapeutic and imaging agents to activated macrophages in rheumatoid arthritis," Advanced Drug Delivery Reviews, 2004; vol. 56: 1205-17.

PCT International Search Report for PCT/US2015/051941 dated Dec. 18, 2015.

PCT International Search Report prepared for PCT/US2016/030150 dated Apr. 29, 2016.

PCT International Search Report/Written Opinion for PCT/US2008/056824, completed Jul. 24, 2009.

PCT International Search Report/Written Opinion for PCT/US2009/061049, completed Mar. 15, 2010.

PCT International Search Report/Written Opinion prepared for PCT/US2010/061897, dated Mar. 11, 2011.

PCT International Search Report/Written Opinion prepared for PCT/US2015/020397, dated Jun. 18, 2015.

(56) References Cited

OTHER PUBLICATIONS

PCT International Search Report/Written Opinion prepared for PCT/US2015/25790, dated Jul. 7, 2015.
PCT International Search Report/Written Opinion prepared for PCT/US2013/065079, dated May 1, 2014.
Peltier, Hillary M., et al., "The Total Synthesis of Tubulysin D," 2006, *J. Am. Chem. Soc.*, No. 128, pp. 16018-16019.
Peterson et al. "Enzymatic cleavage of peptide-linked radiolabels from immunoconjugates" Bioconjugate Chemistry, 1999;10(4):553-7. Abstract Only.
Piontek, Klaus B., et al. "A Functional Floxed Allele of Pkd1 that Can Be Conditionally Inactivated In Vivo", *J. Am. Soc. Nephrol.* vol. 15, pp. 3035-3043.
Pizzorno et al. "5,10-Dideazatetrahydrofolic acid (DDATHF) transport in CCRFCEM and MA104 cell lines." J. Biol, Chem., 1993; 268(2):247-258.
Pizzorno G., et al., "Intracellular metabolism of 5,10-dideazatetrahydrofolic acid in human leukemia cell lines," *Molecular Pharmacology*, 1991, 39 (1), pp. 85-89.
Plante et al., "Polyglutamyl and polylysyl derivatives of the lysine analogues of folic acid and homofolic acid," *Journal of Medical Chemistry*, 19: 1295-1299 (1976).
Politis I. et al., "The Effect of Various Vitamin E Derivatives on the Urokinase-Plasminogen Activator System of Ovine Macrophages and Neutrophils," *British Journal of Nutrition*, vol. 89, 2003, pp. 259-265.
Polyak et al., "Introduction of spacer peptides N-terminal to a cleavage recognition motif in recombinant fusion proteins can improve site-specific cleavage," Protein Eng., 1997; 10(6):615-9.
Pouvreau, Isabelle et al.: "Effect of macrophage depletion by liposomes containing dichloromethylene-diphosphonate on endotoxin induce uveitis." J. Neuroimmun. (1998)86 p. 171-181.
Prabhu V. et al., "*Arabidopsis* dihydropteroate synthase: general properties and inhibition by reaction product and sulfonamides," *Phytochem.*, 1997; 45(1): 23-27.
Prasad et al., "Functional coupling between a bafilomycin A1-sensitive proton pump and a probenecid-sensitive folate transporter in human placental choriocarcinoma cells," *Biochim. Biophys. Acta*, 1994; 1222(2): 309.
Pratt, A.G. et al. "The Hydrolysis of Mono-, Di, and Triglutamate Derivatives of Folic Acid With Bacterial Enzymes," *The Journal of Biological Chemistry*, 1968, vol. 243, No. 24, pp. 6367-6372.
Principles of Ion Exchange Chromatography, http://www.separations.us.tosohbioscience.com/ServiceSupport/TechSupport/ResourceCenter/PrinciplesofChromatography/IonExchange, downloaded Dec. 23, 2009.
Punj, V. et al., "Effect of Vitamin D Analog (1α Hydroxy D5) Immunoconjugated to Her-2 Antibody on Breast Cancer," *Int. J. Cancer*, 2004; 108: 922-929.
Putnam et al., "Polymer conjugates with anticancer activity", Advances in Polymer Science 1995, 122, 55-123.
Raghavan B et al., "Cytotoxic Simplified Tubulysin Analogues," *J. Med. Chem.*, 2008; 51(6), pp. 1530-1533.
Ranasinghe, M. G. et al.; "A Facile Synthesis of Unsymmetrical Thiolsulfonates via Sulfonylation of Mercaptans," *Synthetic Communications*, 1988; 18(3), pp. 227-232.
Rao et al., Journal of Medicinal Chemistry, 1985, 28:1079-1088.
Reddy et al., "In vivo structural activity and optimization studies of folate-tubulysin conjugates," *Molecular pharmaceutics* 2009, 6, 1518-25.
Reddy et al., "Preclinical evaluation of (99m)Tc-EC20 for imaging folate receptor-positive tumors," J Nucl Med. May 2004;45(5):857-66.
Reddy et al., "Optimization of folate-conjugated liposomal vectors for folate receptor-mediated gene therapy," *J. Pharm. Sci*, 88(11): 1112-1118 (1999).
Reddy et al., "Preclinical evaluation of EC145, a folate-vinca alkaloid conjugate," *Cancer Res.*, 2007; 67:4434-42.
Reddy et al., "Retargeting of viral vectors to the folate receptor endocytic pathway," *J Control Release*, 74(1-3): 77-82 (2001).
Reddy, J. A., Low, P. S., "Folate-Mediated Targeting of Therapeutic and Imaging Agents to Cancers," *Crit. Rev. Ther. Drug Carrier Syst.*, vol. 15, No. 6, 1998, pp. 587-627.
Regueiro-Ren et al., "Synthesis and Biological Activity of Novel Epothilone Aziridines," Organic Letters, 2001; vol. 3, No. 17: 2693-96.
Remy et al., Proceedings of the National Academy of Sciences of the United States of America, 1999, vol. 96, No. 10, pp. 5394-5399.
Renz P. et al., "Synthesis of 4-Aza-5, 6-diethylbenzimidazole and Biosynthetic Preparation of 4- and 7-Aza-5, 6-dimethylbenzimidazolylcobamide," *Z. Naturforsch*, 1997, vol. 52c, pp. 287-291.
Reubi et al., "Localization of Cholecystokinin A and Cholecystokinin-BI Gastrin receptors in the human stomach," Gastroenterology (1997) 112:1197-1205.
Reubi et al., "Cholecystokinin(CCK)-A and CCK-B/gastrin receptors in human tumors," Apr. 1, ,CancerRes., vol. 57, pp. 1377-1386, 1997.
Reubi, J. C., and Waser, B. Unexpected high incidence of cholecystokinin B/gastrin receptors in human medullary thyroid carcinomas. Int. J. Cancer vol. 67, pp. 644-647,1996.
Rijnboutt et al., "Endocytosis of GPI-linked membrane folate receptor-alpha," *J. Cell Biol.*, 132(1-2): 35-47 (1996).
Roberts et al., "Folic acid analogs. Modifications in the benzene-ring region. 3. Neohomofolic and neobishomofolic acids. An improved synthesis of folic acid and its analogs," *Journal of Medical Chemistry*, 16: 697-699 (1973).
Roberts et al., "Folic acid analogs. Modifications in the benzene-ring region. 2. Thiazole analogs," *Journal of Medical Chemistry*, 15: 1310-1312 (1972).
Roberts et al., "Folic acid analogs. Modifications in the benzene-ring region. 1. 2'- and 3'-Azafolic acids," *Journal of Medical Chemistry*, 14: 125-130 (1971).
Roberts et al., "Folic acid analogs. Modifications in the benzene-ring region. 4.3'-Ethyl- and 3'-isopropylfolic acids," *Journal of Medical Chemistry*, 17: 219-222 (1974).
Rosario Herranz. Cholecystokinin antagonists: Pharmacological and therapeutic potential. Medicinal Research reviews 23 (5) 559-605, 2003.
Rose W.C., "Taxol-Based Combination Chemotherapy and Other In Vivo Preclinical Antitumor Studies," *J Natl Cancer Inst Monogr*, 1993, No. 15, pp. 47-53.
Ross et al., "Differential regulation of folate receptor isoforms in normal and malignant tissues in vivo and in established cell lines. Physiologic and clinical implications," *Cancer*, 73(9): 2432-2443, (1994).
Rothberg et al, "Cholesterol controls the clustering of the glycophospholipid-anchored membrane receptor for 5-methyltetrahydrofolate," *J. Cell Biol.*, 111(6): 2931-2938 (1990).
Rothberg et al., "The glycophospholipid-linked folate receptor internalizes folate without entering the clathrin-coated pit endocytic pathway," *J. Cell Biol.*, 110(3): 637-649 (1990).
Rothenberg et al. "Further observations on the folate-binding factor in some leukemic cells" J. Clin. Invest. 1971; 50(3):719-726.
Roy et al., "Folate-mediated targeting of T cells to tumors," Advanced Drug Delivery Reviews, 2004; vol. 56: 1219-31.
Roy et al., "Targeting T cells against brain tumors with a bispecific ligand-antibody conjugate," *Int. J. Cancer* 76(5): 761-66 (1998).
Rudinger, peptide Hormones, JA Parsons, Ed., 1976, pp. 1-7.
Sabharanjak et al., "Folate receptor endocytosis and trafficking," Advanced Drug Delivery Reviews, 2004; vol. 56: 1099-1109.
Sadasivan et al., "The complete amino acid sequence of a human folate binding protein from KB cells determined from the cDNA," *J. Biol. Chem.*, 1989; 264: 5806-5811.
Saillan-Barreau Dufresne M. Clerc P. Sanchez D. Corominola H. Moriscot C. Guy Crotte O.Escrieut C. Vaysse N. Gomis R. Tarasova N. Fourmy D. Evidence for a functional role of the Cholecystokinin-B/gastrin receptor in the human fetal and adult pancreas. Diabetes 48 2015-2021, 1999.
Sanderson et al., "In vivo drug-linker stability of an anti-CD30 dipeptide-linked auristatin immunoconjugate," *Clinical Cancer Research*, 2005; 11:843-852.

(56) References Cited

OTHER PUBLICATIONS

Sargent D.R. et al., "Antimetabolites of Pantothenic Acid, Ureido- and Carbamoyl-Derivatives," *Texas Reports on Biology and Medicine*, 1975, vol. 33, No. 3, pp. 433-443.
Sasse F. et al., "Tubulysins, New Cytostatic Peptides from Myxobacteria Acting on Microtubuli Production, Isolation, Physico-Chemical and Biological Properties," *The Journal of Antibiotics*, 2000; vol. 53, No. 9, pp. 879-885.
Scott J.M, "Preparation and Purification of Pteroic Acid from Pteroylglutamic Acid (Folic Acid)," *Methods in Enzymology*, 1980, vol. 66, pp. 657-660.
Search Report for Taiwan Patent Application No. 093101735, dated Jul. 14, 2007, 1 page.
Selhub et al. "Renal folate adsorption and the kidney folate binding protein I. Urinary Clearance studies" Am. J Physiol. 252:F750-F756.
Selhub et al. "Renal folate adsorption and the kidney folate binding protein II. Microinfusion studies" Am. J. Physiol. 252:F757-F760.
Selhub et al. "The folate binding protein of rat kidney. Purification, properties, and cellular distribution" J. Biol. Chem. 1984;259(10):6601-6606.
Semb J. et al., "Pteroic Acid Derivatives. V. Pteroyl-α-glutamyl-α-glutamylglutamic Acid, Pteroyl-γ-glutamyl-α-glutamylglutamic Acid, Pteroyl-α-glutamyl-γ-glutamylglutamic Acid," *JACS*, 1949; 71 (7): 2310-2315.
Senter et al., "Development of a Drug-Release Strategy Based on the Reductive Fragmentation of Benzyl Carbamate Disulfides," *J. Org. Chem.*, 55: 2975-2978 (1990).
Sethi, T., Herget, T., Wu, S. V., Walsh, J. H., and Rozengurt, E. CCK-A and CCK-B receptors are expressed in small cell lung cancer lines and mediate Ca2+ mobilization and clonal growth. Cancer Res., vol. 53, pp. 5208-5213, 1993.
Shealy Y.F., "Synthesis and Evaluation of Some New Retinoids for Cancer Chemoprevention," *Preventive Medicine*, 1989, vol. 18, pp. 624-645.
Shillingford, Jonathan M., et al., "The mTOR Pathway is Regulated by Polycystin-1, and its Inhibition Reverses Renal Cystogenesis in Polycyctic Kidney Disease", Apr. 4, 2006, *PNAS*. vol. 103, No. 14, pp. 5466-5471.
Shimizu M. et al., "Synthesis and biological activities of new 1alpha, 25-dihydroxy-19-norvitamin D3 analogs with modifications in both the A-ring and the side chain," *Bioorganic & Medicinal Chemistry*, 2006; 14(12): 4277-94.
Shimizu, Kazui, et al., "Novel vitamin D3 antipsoriatic antedrugs: 16-En-22-oxa-1a,25-(OH)2D3 analogs," *Bioorganic & Medicinal Chemistry*, 2006;14: 1838-1850.
Shoup T.M. et al., "Synthesis of Fluorine-18-Labeled Biotin Derivatives: Biodistribution and Infection Localization," *J. Nucl. Med.*, 1994; 35: 1685-1690.
SIGMA, 2004, pp. 1-2.
Singh et al, Recent trends in targeted anticancer prodrug and conjugate design, Curr Med Chem, 2008, 15(18): 1802-1826.
Sirotnak. "Obligate genetic expression in tumor cells of a fetal membrane property mediating "Folate" transport: biological significance and implications for improved therapy of human cancer" Cancer Res., 1985;45(9):3992-4000.
Skinner W.A. et al., "Structure-Activity Relations in the Vitamin E Series. II. Derivatives of α-Tocopherol Substituted at the 5-Methyl Group," *J. Med. Chem.*, 1969; 12 (1): 64-66.
Smart et al., "Clustered folate receptors deliver 5-methyltetrahydrofolate to cytoplasm of MA104 cells," *J. Cell Biol.*, 134(5): 1169-1177 (1996).
Smart et al., "Protein kinase C activators inhibit receptor-mediated potocytosis by preventing internalization of caveolae," *J. Cell Biol.*, 124(3): 307-313 (1994).
Smith et al., *Characterization of the CCK-C (cancer) receptor in human pancreatic cancer.* 2002, Int. J. Mol. Med., vol. 10, pp. 689-694.
Smith, "Quantitative analysis of gastrin mRNA and peptide in normal and cancerous human pancreas," International Journal of Molecular Medicine 2(3) 309-315 1998.
Speckamp, et al.; "New Developments in the Chemistry of N-Acyliminium Ions and Related Intermediates" Tetrahedron 2000 vol. 56(24) 3817-3856.
Spry C. et al., "A Class of Pantothenic Acid Analogs Inhibits Plasmodium Falciparum Pantothenate Kinase and Represses the Proliferation of Malaria Parasites," *Antimicrobial Agents and Chemotherapy*, 2005; 49(11): 4649-4657.
Stein et al. "Normal tissue reactivity of four anti-tumor monoclonal antibodies of clinical interest" Int. J. Cancer 1991;47(2):163-169.
Steinberg, G. et al., "Synthesis and Evaluation of Pteroic Acid-Conjugated Nitroheterocyclic Phosphoramidates as Folate Receptor-Targeted Alkylating Agents," *J. Med. Chem.* 44: 69-73 (2001).
Steinmetz, H. et al., "Isolation, Crystal and Solution Structure Determination, and Biosynthesis of Tubulysins-Powerful Inhibitors of Tubulin Polymerization from Microbacteria", *Angew. Chem. Int. Ed.*, 2004, No. 43, pp. 4888-4892.
Sun et al., "Blockade of cholecystokin-2 receptor and cyclooxygenase 2 synergistically induces cell apoptosis and inhibits the proliferation of human gastric cancer cells in vitro," Cancer Letters 263 (2) 302-311 2008.
Takahata Y. et al., "Synthesis, Properties and Microbiological Activity of Hydrophobic Derivatives of Vitamin B12," *J. Nutr. Sci. Vitaminol.*, 1995, vol. 41, pp. 515-526.
Takasu, H. et al., "c-Fos protein as a target of anti-osteoclastogenic action of vitamin D, and synthesis of new analogs," *The Journal of Clinical Investigation*, 2006; vol. 116, No. 2, pp. 528-535.
Takeda, K. et al., "A Synthesis of a New Type of Alkoxycarbonylating Reagents from 1,1-Bis[6-(trifluoromethyl)benzotriazolyl] Carbonate (BTBC) and Their Reactions," *Sythesis*, 1987; 6: 557-560.
Tanaka et al. "Preparation and characterization of a disulfide-linked bioconjugate of annexin V with the B-chain of urokinase: an improved fibrinolytic agent targeted to phospholipid-containing thrombi" Biochemistry, 1996;35(3):922-9. Abstract Only.
Tang C, Biemond I. Lamers CB. Cholecystokinin receptors in human pancreas and gall bladder muscle: a comparative study. Gastroenterology 111,1621-1626, 1996.
Temple et al., "Synthesis of pseudo cofactor analogs as potential inhibitors of the folate enzymes," *Journal of Medical Chemistry*, 25: 161-166 (1982).
Testa B, Prodrug Research: Futile or Fertile?, Biochem Pharm, 2004, 68, pp. 2097-2106.
Thaden et al. "Photoaffinity behavior of a conjugate of oligonucleoside methylphosphonate, rhodamine, and psoralen in the presence of complementary oligonucleotides" Bioconjugate Chemistry, 1993;4(5):386-94. Abstract Only.
Theti, D. S. et al., "Selective delivery of CB300638, a cyclopenta[g]quinazoline-based thymidylate synthase inhibitor into human tumor cell lines overexpressing the alpha-isoform of the folate receptor," Cancer Res, 2003; 63(13): 3612-3618.
Todisco A., Ramamoorthy S., Witham T., Pausawasdi N., Srinivasan S., Dickinson C.J., Askari F.K, Krametter D. Molecular Mechanisms for the antiapoptotic actions of gastrin. Am J Physiol Gastrointest Liver Physiol280: G298-G307, 2001.
Toffoli et al. "Expression of folate binding protein as a prognostic factor for response to platinum-containing chemotherapy and survival in human ovarian cancer" Int. J. Cancer (Pred. Oncol) 1998; 79:121-126.
Toffoli et al., "Overexpression of folate binding protein in ovarian cancers," *Int. J. Cancer* 74(2): 193-198 (1997).
Toraya T. et al., "Immobilized Derivatives of Vitamin B12 Coenzyme and Its Analogs," *Methods in Enzymology*, vol. 67, pp. 57-66.
Toraya T. et al., "The Synthesis of Several Immobilized Derivatives of Vitamin B12 Coenzyme and Their Use as Affinity Adsorbents for a Study of Interactions of Diol Dehydrase with the Coenzyme," *The Journal of Biological Chemistry*, 1990; vol. 255, No. 8, pp. 3520-3525.
Trachewsky D., "Antihypertensive Effect of Riboflavin Analogs in Rats with Mineralocorticoid-Induced Hypertension," *Hypertension*, 1981; vol. 3, No. 1, pp. 75-80.

(56) References Cited

OTHER PUBLICATIONS

Truneh A. et al., "Temperature-sensitive differential affinity of TRAIL for its receptors. DR5 is the highest affinity receptor," *J Biol Chem*, 2000; 275(30):23319-25.

Turek et al., "Endocytosis of folate-protein conjugates: ultrastructural localization in KB cells," *J. Cell Sci.* 106: 423-430 (1993).

Turk et al., "Characterization of a novel pH-sensitive peptide that enhances drug release from folate-targeted liposomes at endosomal pHs," *Biochim Biophys Acta*, 1559(1): 56-68 (2002).

Ueda M. et al., "Effect of Vitamin B12 Derivatives on Urinary Excretion of Methylmalonic Acid in Liver Diseases," *Acta Med. Okayama*, 1970; vol. 24, pp. 365-372.

Umemoto et al., "Molecular design of methotrexate-antibody conjugates for targeted cancer treatment", Journal of Bioactive and Compatible Polymers, 1992, 7(2), 191-219.

Univesity of Maryland Medical Center (UMMC), Vitamin B9 (folic acid), 2014, http://umm.edu/health/medical/altmed/supplement/vitamin-b9-folic-acid, pp. 1-8.

Varma, R. et al., "GPI-anchored proteins are organized in submicron domains at the surface," *Nature*, 394(6695): 798-801 (1998).

Verwey, J., "Mitomycin C-Induced Renal Toxicity, a Dose-Dependent Side Effect?," *Eur J Cancer Clin Onco*, 1987; vol. 23, No. 2, pp. 195-199.

Vesely D.L. et al., "Biotin Analogs Activate Guanylate Cyclase," *Molecular and Cellular Biochemistry*, 1984; vol. 60, pp. 109-114.

Vlahov et al., "Carbohydrate-Based Synthetic Approach to Control Toxicity Profiles of Folate-Drug Conjugates," Journal of Organic Chemistry 75: 3685-3691 (2010).

Vlahov I. et al., "An assembly concept for the consecutive introduction of unsymmetrical disulfide bonds: synthesis of a releasable multidrug conjugate of folic acid," 2007, J. Org Chem, 72, 5968-5972.

Vlahov I. et al., "Design and regioselective synthesis of a new generation of targeted therapeutics. Part 3: Folate conjugates of aminopterin hydrazide for the treatment of inflammation," 2011, Bioorg. Med. Chem. Lett., 21, 1202-1205.

Vlahov I.R. et al., "Design and regioselective synthesis of a new generation of targeted chemotherapeutics. Part 1: EC145, a folic acid conjugate of desacetylvinblastine monohydrazide," *Bioorg Med Chem Lett*, 2006; 16(19):5093-6.

Vlahov, I. et al., "Design and regioselective synthesis of a new generation of targeted chemotherapeutics. Part II: Folic acid conjugates of tubulysins and their hydrazides," Bioorg. Med. Chem. Lett., 2008, 18(16), 4558-4561.

Voet et al, Biochemistry, John Wiley & Sons Inc., 1995, pp. 235-241.

Vogel et al., "Peptide-Mediated Release of Folate-Targeted Liposome Contents From Endosomal Compartments," *J. Am. Chem. Soc.*, 1996; 118(7): 1581-1586.

Vyas D. et al., "A practical synthesis of mitomycin A and its analogs," *J Org Chem*, 1986; 31:4307-4309.

Wang et al., "Structure-activity and high-content imaging analyses for novel tubulysins," Chemical Biology & Drug Design, 2007; 70(2): 75-86.

Wang et al., "Vitamin E Analogs Trigger Apoptosis in HER2/erbB2-Overexpressing Breast Cancer Cells by Signaling Via the Mitochondrial Pathway," *Biochemical and Biophysical Research Communication*, 2005; vol. 326, pp. 282-289.

Wang et al., "Delivery of antisense oligodeoxyribonucleotides against the human epidermal growth factor receptor into cultured KB cells with liposomes conjugated to folate via polyethylene glycol," *Proc. Natl. Acad. Sci. USA*, 92(8): 3318-3322 (1995).

Wang et al., "Design and synthesis of [111In]DTPA-folate for use as a tumor-targeted radiopharmaceutical," *Bioconjug Chem.*, 8(5): 673-679 (1997).

Wang et al., "Synthesis, purification, and tumor cell uptake of 67Ga-deferoxamine-folate, a potential radiopharmaceutical for tumor imaging," *Bioconj. Chem.*, 1996; 7(1): 56-62.

Wang S. et al., "Folate-mediated targeting of antineoplastic drugs, imaging agents, and nucleic acids to cancer cells," *J. Control Rel*, 1998; 53(1-3): 39-48.

Wang, L. et al., "Synthesis, biological, and antitumor activity of a highly potent 6-substituted pyrrolo[2,3-d]pyrimidine thienoyl antifolate inhibitor with proton-coupled folate transporter and folate receptor selectivity over the reduced folate carrier that inhibits β-glycinamide ribonucleotide formyltransferase," 2011, J. Med. Chem., 54, 7150-7164.

Water, from http://www.biology-ionline.org/dictionary/Water, pp. 103, accessed Apr. 24, 2014.

Weinberg et al., Cholecystokinin A and B receptors are differentially expressed in normal and pancreatic adenocarcinoma. J. Clinical Investigation 100,597-603, 1997.

Weinstein, "Commentary: Three Decades of Folic Acid Antagonists in Dermatology," *Arch Dermatol*, Jun. 1983, vol. 119, 525-527.

Weinstock et al., "Folic acid analogs. II. p-{[(2,6-Diamino-8-purinyl)methyl]amino}-benzoyl-L-glutamic acid and related compounds," *Journal of Medical Chemistry*, 13: 995-997 (1970).

Weitman et al. "Distribution of the folate receptor GP38 in normal and malignant cell lines and tissues" Cancer Res. 1992;52(12):3396-3401.

Weitman et al., "Cellular localization of the folate receptor: potential role in drug toxicity and folate homeostasis," *Cancer Res.*, 1992; 52(23): 6708-6711.

Weitman et al., "Distribution of the folate receptor GP38 in normal and malignant cell lines and tissues," *Cancer Res.*, 1992; 52(12): 3396-3401.

Westerhof et al. "Membrane transport of natural folates and antifolate compounds in murine L1210 Leukemia cells: role of carrier-and receptor mediated transport systems" Cancer Res. 1991;51:5507-5513.

Westerhof G.R. et al., "Carrier- and Receptor-Mediated Transport of Folate Antagonists Targeting Folate-Dependent Enzymes: Correlates of Molecular-Structure and Biological Activity," *Molecular Pharmacology*, 1995, 48, pp. 459-471.

Westerhof GR et al., "A photoaffinity analogue of folic acid as a probe for the identification and function of a membrane folate binding protein (mFBP) in human CCRF-CEM leukemia cells," *Proccedings of the American Association for Cancer Research*, 1991; 32:328.

Weygand, et al., Chemishe. Berichte (1950) 83, 460-467.

Wiener et al., "Targeting dendrimer-chelates to tumors and tumor cells expressing the high-affinity folate receptor," *Invest. Radiol.* 32(12): 748-54 (1997).

Wikipedia, Analog (Chemistry), http://en.wikipedia.org/wiki/Analog_(chemistry), downloaded Dec. 16, 2009.

Wikipedia, Complex (Chemistry), http://en.wikipedia.org/wiki/Complex_(chemistry), downloaded Dec. 23, 2009.

Wikipedia, Conjugate, http://en.wikipedia.org/wiki/Conjugate, downloaded Dec. 17, 2009.

Wikipedia, Derivative (Chemistry), http://en.wikipedia.org/wiki/Derivative_(chemistry), downloaded Dec. 16, 2009.

Wikipedia, Folic acid, http://en.wikipedia.org/wiki/Folic_acid, downloaded Apr. 7, 2009.

Wikipedia, Functional analog, http://en.wikipedia.org/wiki/Functional_analog, downloaded Apr. 7, 2009.

Wikipedia, List of Purification Methods in Chemistry, http://en.wikipedia.org/wiki/List_of_purification_methods_in_chemistry, downloaded Dec. 16, 2009.

Wikipedia, Solution, http://en.wikipedia.org/wiki/Solution, downloaded Dec. 17, 2009.

Wikipedia, Structural analog, http://en.wikipedia.org/wiki/Structural_analog, downloaded Apr. 7, 2009.

Williams et al. "Renal tubular transport of folic acid and methotrexate in the monkey" Am. J. Physiol 1982; 242(5):F484-490.

Wolf et al., Journal of the American Chemical Society, 1947, 69: 2753-2759.

Wu et al., "Enhancing the enantioselectivity of candida lipase catalyzed ester hydrolysis via noncovalent enzyme modification," *Journal of American Chemical Society*, 1990; 112:1990-1995.

(56) References Cited

OTHER PUBLICATIONS

Wu M. et al., "Clustering of GPI-anchored folate receptor independent of both cross-linking and association with caveolin," *J. Membr. Biol.* 159(2): 137-147 (1997).

Yang, et al., "Characterization of the pH of Folate Receptor-Containing Endosomes and the Rate of Hydrolysis of Internalized Acid-Labile Folate-Drug Conjugates," JPET 321: 462-468, 2007.

Zaragoza, D., Side Reactions in Organic Synthesis, 2005, Wiley-VCH Verlag GmbH & Co. KGaA, Weinheim, Preface, p. 9.

Zhao et al., "Tumor-selective targeted delivery of genes and antisense oligodeoxyribonucleotides via the folate receptor," Advanced Drug Delivery Reviews, 2004; vol. 56: 1193-1204.

Zhou et al., Blocking gastrin and CCK-B autocrine loop affects cell proliferation and apoptosis in vitro. Molecular and Cellular Biochemistry 343 (1-2) 133-141 (2010).

Zimmer H. et al., "Potential anticancer agents V., Synthesis of folic acid and pteroic acid analogs derived of caffeine and theophylline," *Arzneimittelforschung*, 1966, 16(4), pp. 541-545.

Zimmerman, J., "Folic acid transport in organ-cultured mucosa of human intestine. Evidence for distinct carriers," *Gastroenterol.* 99(4): 964-972 (1990).

\* cited by examiner

Binding of compound 19 (CRL-LS288) in HEK CCK2i4svR cells

Binding of compound 19 (CRL-LS288) in HEK CCK2R cells

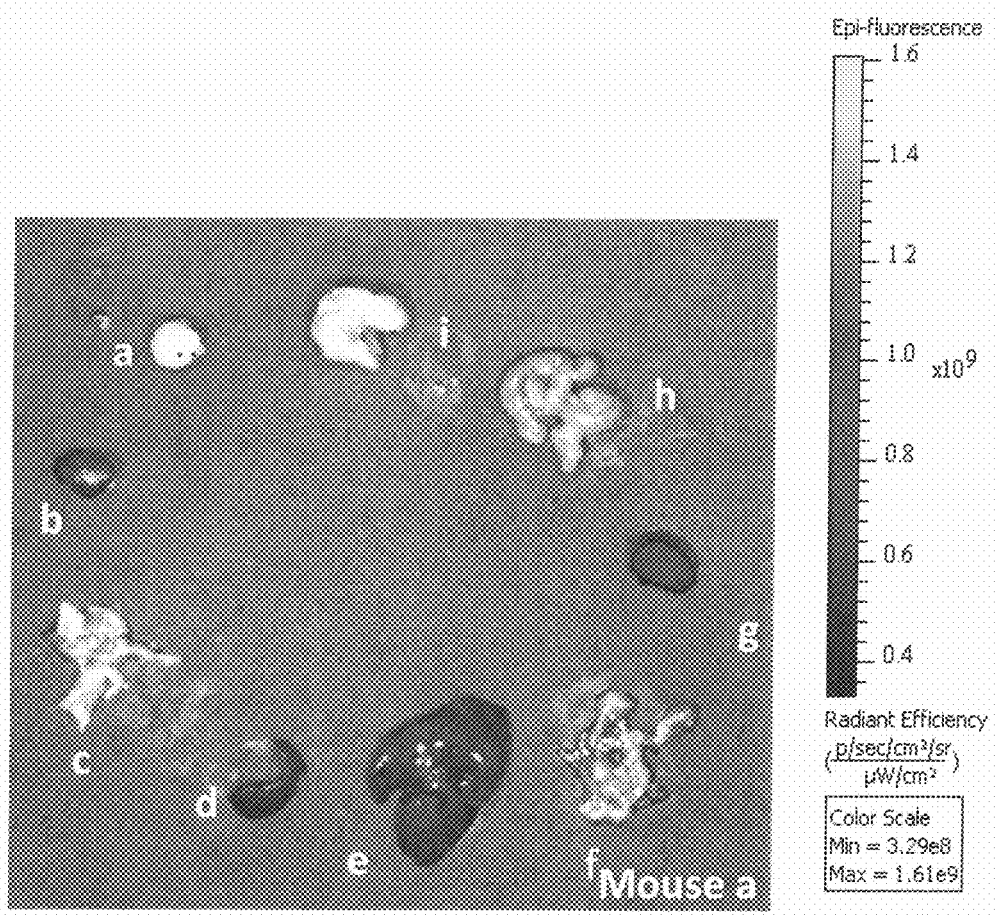

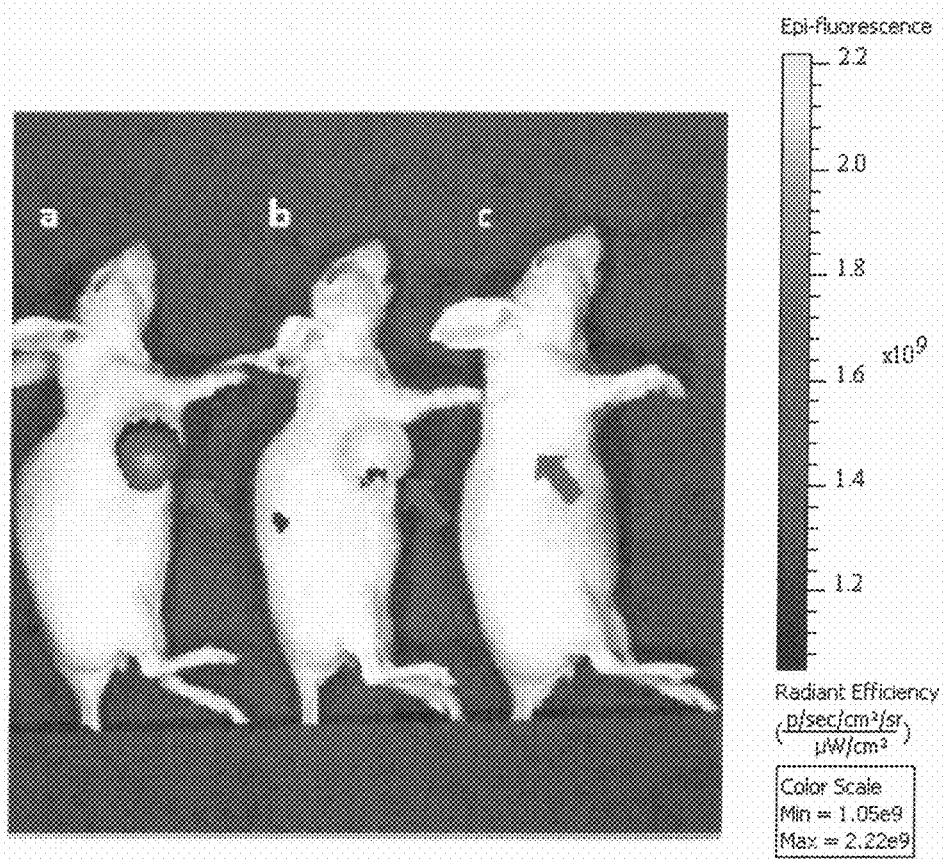

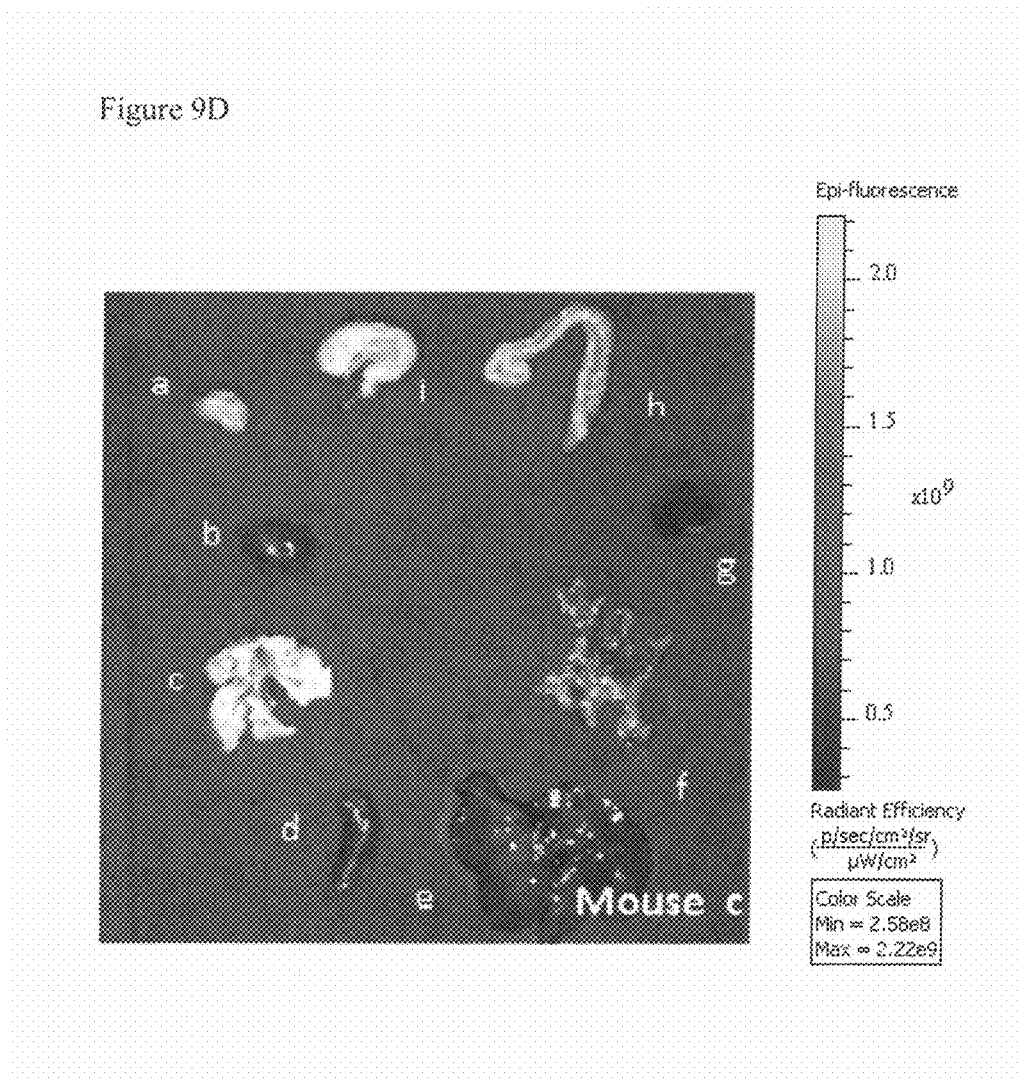

CHOLECYSTOKININ B RECEPTOR TARGETING FOR IMAGING AND THERAPY

CROSS-REFERENCE TO RELATED APPLICATIONS

This application is a U.S. national counterpart application of international application serial No. PCT/US2013/027463 filed Feb. 22, 2013, which claims priority to U.S. Provisional Patent Application Ser. No. 61/602,831 filed on Feb. 24, 2012, the entire disclosures of which are hereby incorporated by reference.

TECHNICAL FIELD

The invention relates to methods of detecting, diagnosing, imaging and treating cancer in a subject.

BACKGROUND OF INVENTION

The cholecystokinin B receptor (also known as CCK2R, CCKBR, and the gastrin receptor) is a trans-membrane, G protein-coupled receptor. CCK2R is primarily expressed in (i) the brain and central nervous system, and (ii) the mucosa of the gastrointestinal tract, including parietal and ECL cells. It is reported to be most abundantly expressed in the cerebral cortex of the mammalian brain where it has been implicated in the regulation of memory/learning and response to stress[1]. In the alimentary canal, its presence has been detected in the GI tissues, as well as exocrine and endocrine pancreas. Conflicting reports suggest the receptor is also expressed in peripheral tissues such as adipocytes and pancreas[2-9], along with CCK1R, a G protein-coupled receptor with 50% homology to CCK2R. The natural ligands of CCK2R are gastrin and cholecystokinin peptides[1].

A number of different types of human tumors have been found that overexpress or ectopically express CCK2R in high densities or at high frequencies including medullary thyroid cancers, insulinomas, small cell lung cancers, non small cell lung cancers, bronchial and ileal carcinoids, GIST tumors, and colon cancers, hepatocellular carcinomas, and pancreatic cancers[10-18]. One manner in which disregulation of CCK2R signaling may contribute to tumor formation or growth relates to gastrin signaling through the receptor. Gastrin is a peptide hormone that stimulates secretion of gastric acid (HCl) by the parietal cells of the stomach upon binding of CCK2R. Gastrin has been reported to be an inhibitor of cancer cell apoptosis, likely through its ability to induce activation of the serine/threonine protein kinase PKB/Akt[19-21]. Several reports have shown that inhibiting the CCK2R receptor and the gastrin autocrine loop induces apoptosis and inhibits the proliferation of the cancer cell lines in vivo.

CCK2 receptors found in tumor tissue have been reported to include both normal protein as well as a constitutively active a CCK2R-receptor splice variant (CCK2i4svR) that has the fourth intron inappropriately retained, resulting in the addition of 69 amino acids in the third intracellular loop domain of the receptor, the domain known to be important for signal transduction[24-29].

Cytotoxic agents that target CCK2R might serve to block uncontrolled activation of the receptor in tumors. Helpfully, because CCK2R is expressed in normal brain tissue, the blood brain barrier will block polar compounds that could affect normal activity of the receptor in the brain. Therefore, where CCK2R and its splice variant are expressed outside of the brain by a tumor, the tumor will be the only tissue targeted by CCK2R and CCK2i4svR-specific cytotoxic agents.

CCK2R-specific antagonists have been developed and extensive structure-activity relationships have reported. Both in vitro and in vivo studies have demonstrated that the growth potentiating effects of gastrin can be abolished in the presence of selective CCK2R antagonists. One such antagonist is Z-360, an orally-active CCK2R antagonist (Zeria Pharmaceuticals Co., Ltd., Tokyo, Japan) that has a $K_i$=0.47 nmol/L with a selectivity ratio over CCK1R=672. Preclinical studies have shown that oral administration of Z-360 along with the chemotherapeutic gemcitabine significantly inhibited subcutaneous PANC-1 tumor growth compared with either agent alone (27.1% inhibition) and significantly increased survival compared with the vehicle. This antagonist is currently in Phase II human clinical trials for treatment of pancreatic cancer in combination therapy with gemcitabine[29-31,34-35]. The modest anti-tumor effect of the antagonist may be due to several factors. First, many cancers involve multiple genetic mutations that are not easily treated by a single agent. There exist multiple redundancies, cross talk and possible compensatory mechanisms between signaling pathways. Consequently blocking one part of a pathway may not always provide enough improvement/antitumor activity that could be translated to improved survival outcome. Secondly, ongoing mutations in the primary molecular target of the drug may also result in drug resistance towards some of these therapies. Third, the presence of a constitutively active splice variant CCK2i4svR means that blocking CCK2R activity using an antagonist may be less effective.

The development of additional agents that selectively target CCK2R and that have the ability to deliver payloads (cytotoxic or diagnostic) would broaden the arsenal of agents that could be used in the treatment and diagnosis of tumors in which CCK2R is expressed. Such agents may also be used in the diagnosis and imaging of cancer in a subject.

BRIEF SUMMARY OF INVENTION

The present invention relates to a small group of highly related benzazepine compounds that selectively target and bind CCK2R and the splice variant CCK2i4svR. The benzazepine compounds are linked to one or more therapeutic or imaging agents, and these conjugates are used in the treatment, diagnosis and imaging of tumors expressing CCK2R and the splice variant.

The invention is thus directed to conjugates comprising a targeting ligand linked to an active moiety. The targeting ligand is a benzazepine compound that selectively binds to CCK2R and/or CCK2i4svR. The active moiety is a therapeutic agent or imaging agent. The targeting ligand and the active moiety are joined by a linker as described herein.

In a first embodiment, the invention is directed to conjugates comprising $$B-[L-D]_n$$

wherein B is a targeting ligand, L is a linker, D is an active moiety, and n is an integer of between 1 and 5. In a particular aspect, n=1.

The targeting ligand Z-360 is an excellent example of a targeting ligand that may be used in the conjugates of the invention.

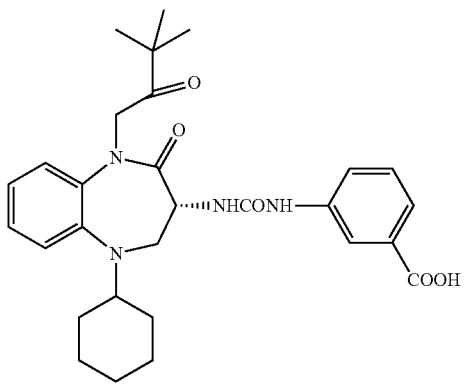

Z-360

Additional, non-limiting examples of targeting ligands of the present invention are compounds of Formula I

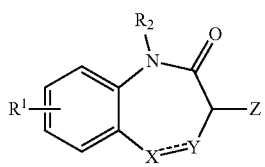

Formula I wherein:

the bond between X and Y is a single bond or a double bond;

$R^1$=H, $CH_3$ or heterocycle with $R^2$;

$R^2$=heterocycle with $R^1$, $CH_3$, $CH_2CON(Et)_2$, $CH_2COC(CH_3)_3$, $CH_2CONHC(CH_3)_3$,

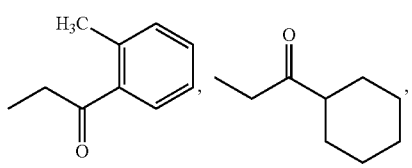

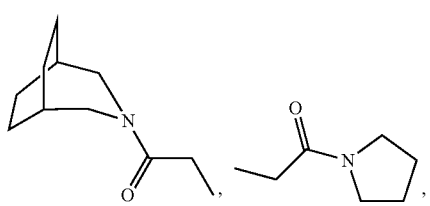

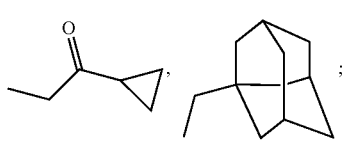

X=$CR^3$ or $NR^4$;

$R^3$=phenyl, cyclohexyl, $CH_3$, $CH_2$—$CH_3$,

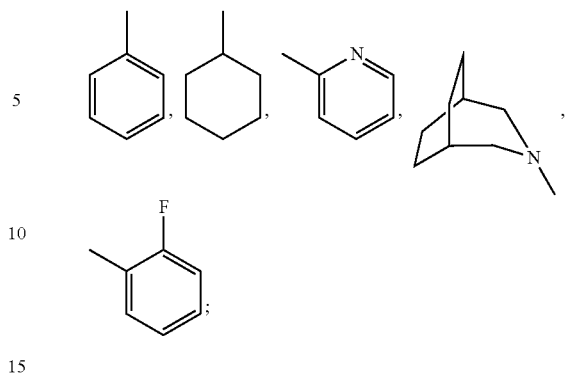

$R^4$=phenyl, cyclohexyl,

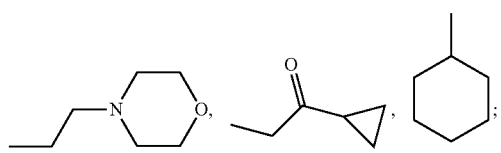

Y=$CH_2$, N (dashed=double bond), C=O;

Z=

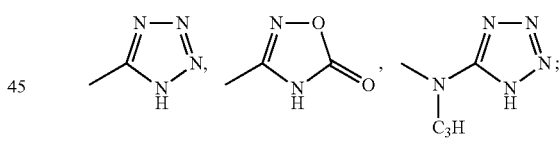

$R^5$=absent, phenyl, Cl, $CO_2H$, $CH_3$, $OCH_3$, $NHCH_3$, F, $SCH_2CO_2H$, $SCH_2CO_2Et$, and analogs, derivatives, salts and esters thereof.

The active moiety D is a therapeutic agent or an imaging agent. Therapeutic agents include, but are not limited to, radio-therapeutic agents, immunotherapeutic agents, photo-dynamic therapy agents and chemotherapeutic agents. Imaging agents include, but are not limited to, radio-imaging agents, optical imaging agents, PET imaging agents, MRI contrast agents, CT contrast agents, and FRET imaging agents. In some aspects, the therapeutic agent is tubulysin B hydrazide or desacetyl vinblastine monohydrazide. In some aspects, the imaging agent is fluorescein (FITC), rhodamine, or a cyanine-based near infrared dye such as 50456, IR800CW, or LS288.

The linker L is a bivalent or polyvalent hydrophilic spacer comprised of charged or polar amino acids, sugars or sugar-containing oligomers, or a hydrophilic polymer such as polyethylene glycol. Specific examples of the linker are L1, L2 or L3

L1: HN-Glu-Arg-Asp-CO
L2: HN-Glu-PS-Glu-PS-CO
L3: HN-Octanoyl-Glu-PS-Glu-PS-CO
wherein PS is the following formula

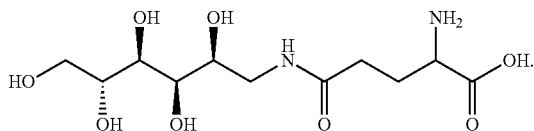

In one aspect, the embodiment includes conjugates of the following formula

B-[L-D]$_n$ wherein B is a targeting ligand of Formula I

Formula I

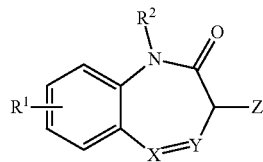

wherein:
the bond between X and Y is a single bond or a double bond;
R$^1$=H, CH$_3$ or heterocycle with R$^2$;
R$^2$=heterocycle with R$^1$, CH$_3$, CH$_2$CON(Et)$_2$, CH$_2$COC(CH$_3$)$_3$, CH$_2$CONHC(CH$_3$)$_3$,

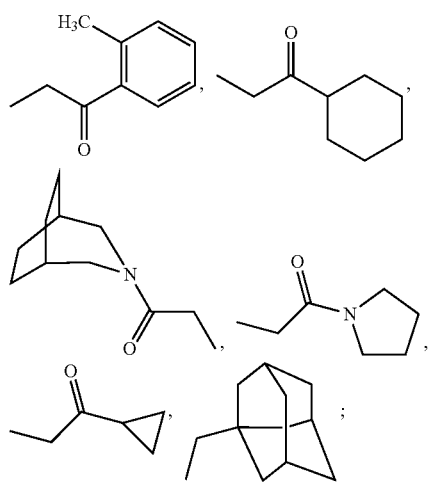

X=CR$^3$ or NR$^4$;
R$^3$=phenyl, cyclohexyl, CH$_3$, CH$_2$—CH$_3$,

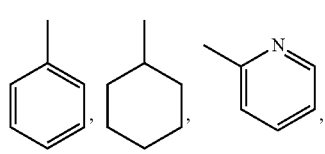

-continued

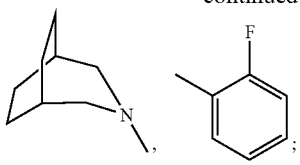

R$^4$=phenyl, cyclohexyl,

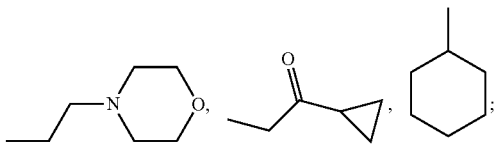

Y=CH$_2$, N (dashed=double bond), C=O;
z=

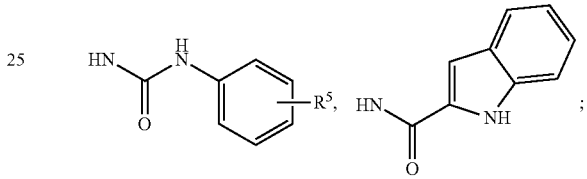

R$^5$=absent, phenyl, Cl, CO$_2$H, CH$_3$, OCH$_3$, NHCH$_3$, F, SCH$_2$CO$_2$H, SCH$_2$CO$_2$Et,

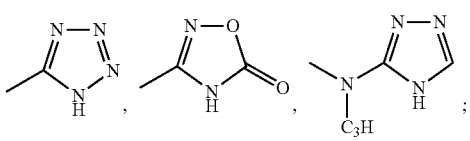

and analogs, derivatives, salts and esters thereof,
L is a bivalent or polyvalent linker,
D is an active moiety, wherein each active moiety is individually selected from therapeutic agents and imaging agents, and n is an integer of between 1 and 5.

In a second embodiment, the invention is directed to methods for detecting a tumor in a subject, comprising administering a conjugate as defined herein to a subject suspected of having a tumor and detecting the conjugate in the subject, wherein the active moiety D of the conjugate is an imaging agent.

In this embodiment, imaging agents include, but are not limited to, radio-imaging agents, optical imaging agents, PET imaging agents, MRI contrast agents, CT contrast agents, and FRET imaging agents. In some aspects, the imaging agent is fluorescein (FITC), rhodamine, S0456, IR800CW, or LS288. In other aspects, the imaging agent is radio-imaging agent comprising $^{111}$In, $^{99m}$Tc, $^{64}$Cu, $^{67}$Cu, $^{67}$Ga or $^{68}$Ga.

In this embodiment, the conjugate is detected utilizing flow cytometry, confocal microscopy, fluorescence activated cell sorters, a fluorescence imaging system, a radioimaging system, MRI, SPECT-CT, or PET imaging.

In a third embodiment, the invention is directed to methods for diagnosing cancer in a subject, comprising administering a conjugate as defined herein to a subject suspected of having cancer and detecting the conjugate in the subject, wherein the active moiety D of the conjugate is an imaging agent.

In this embodiment, imaging agents include, but are not limited to, radio-imaging agents, optical imaging agents, PET imaging agents, MRI contrast agents, CT contrast agents, and FRET imaging agents. In some aspects, the imaging agent is fluorescein (FITC), rhodamine, S0456, IR800CW, or LS288. In other aspects, the imaging agent is radio-imaging agent comprising $^{111}$In, $^{99m}$Tc, $^{64}$Cu, $^{67}$Cu, $^{67}$Ga or $^{68}$Ga.

In this embodiment, the conjugate is detected utilizing flow cytometry, confocal microscopy, fluorescence activated cell sorters, a fluorescence imaging system, a radioimaging system, MRI, SPECT-CT, or PET imaging.

In a fourth embodiment, the invention is directed to methods for imaging cancer in a subject, comprising administering a conjugate as defined herein to a subject suspected of or having cancer and detecting the conjugate in the subject, wherein the active moiety D of the conjugate is an imaging agent.

In this embodiment, imaging agents include, but are not limited to, radio-imaging agents, optical imaging agents, PET imaging agents, MRI contrast agents, CT contrast agents, and FRET imaging agents. In some aspects, the imaging agent is fluorescein (FITC), rhodamine, S0456, IR800CW, or LS288. In other aspects, the imaging agent is radio-imaging agent comprising $^{111}$In, $^{99m}$Tc, $^{64}$Cu, $^{67}$Cu, $^{67}$Ga or $^{68}$Ga.

In this embodiment, the conjugate is detected utilizing flow cytometry, confocal microscopy, fluorescence activated cell sorters, a fluorescence imaging system, a radioimaging system, MRI, SPECT-CT, or PET imaging.

In a fifth embodiment, the invention is directed to methods for treating a subject having cancer, comprising administering a therapeutically-effective amount of a conjugate as defined herein to a subject having cancer, wherein the active moiety D of the conjugate is a therapeutic agent.

In this embodiment, therapeutic agents include, but are not limited to, radio-therapeutic agents, immunotherapeutic agents, photodynamic therapy agents and chemotherapeutic agents. In some aspects, the therapeutic agent is tubulysin B hydrazide or desacetyl vinblastine monohydrazide.

In certain aspects of this embodiment, the conjugate will be in a pharmaceutical composition comprising the conjugate and a pharmaceutically acceptable diluent or carrier.

In relevant embodiments of the invention, cells of the tumor express CCK2R or CCK2i4svR, or both. The tumor may be, but is not limited to, medullary thyroid cancers, insulinomas, small cell lung cancers, non small cell lung cancers, astrocytoma, gastric cancer, bronchial and ileal carcinoids, GIST tumors, and colon cancers, prostate cancer, hepatocellular carcinomas, and pancreatic cancers.

In relevant embodiments of the invention, the cancers that may be diagnosed, imaged or treated include those that express CCK2R or CCK2i4svR, or both. The cancers include, but are not limited to, medullary thyroid cancers, insulinomas, small cell lung cancers, non small cell lung cancers, astrocytoma, gastric cancer, bronchial and ileal carcinoids, GIST tumors, and colon cancers, prostate cancer, hepatocellular carcinomas, and pancreatic cancers.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF DRAWINGS

FIGS. 8A-C display the overlay of fluorescent imaging of conjugate 19 over white light images of mice and their dissected organs, displaying the preferential binding of the conjugate to CCK2R tumor cells. Tumors and kidneys are shown with arrows. Dissected organs are labeled as follows: a-tumor, b-heart, c-lungs, d-spleen, e-liver, f-pancreas g-kidneys, h-small intestines, i-stomach. Mouse a is injected with 10 nMols of CRL-LS288+excess CRL whereas mouse b is injected with only 10 nmol CRL-LS288

FIGS. 9A-D display the overlay of fluorescent imaging of conjugate 19 over white light images of mice and their dissected organs, displaying the preferential binding of the conjugate to CCK2i4svR tumor cells. Tumors and kidneys are shown with. Dissected organs are labeled as follows: a-tumor, b-heart, c-lungs, d-spleen, e-liver, f-pancreas g-kidneys, h-small intestines, i-stomach. Mouse a is injected with 10 nMols of CRL-LS288, whereas mouse b is injected with 10 nmol CRL-LS288+excess CRL and mouse c is a CCK2R negative tumor injected with 10 nMols of CRL-LS288.

DETAILED DESCRIPTION OF THE INVENTION

I. Definitions

Figure 1:
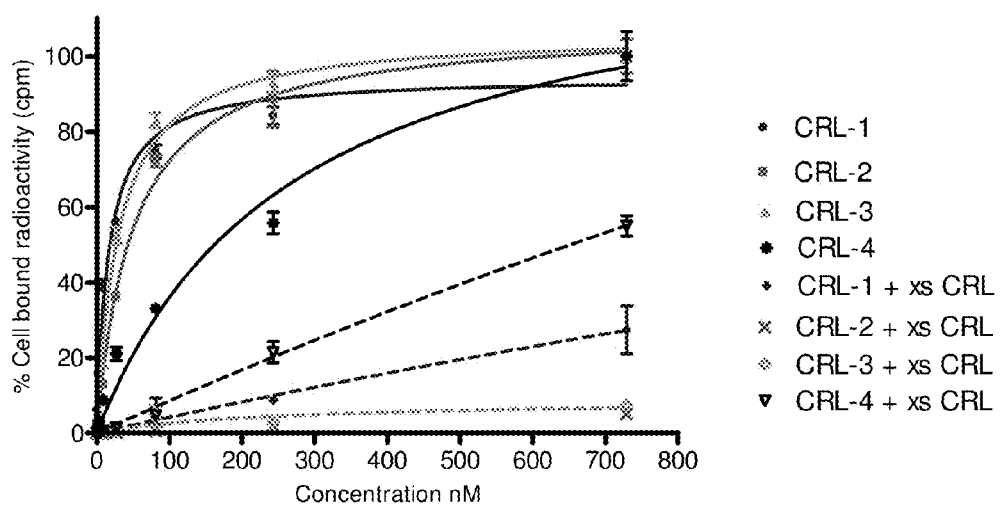
FIG. 1 graphically displays the binding of CRL-1, CRL-2, CRL-3 and CRL-4 to HEK CCK2R tumor cells.

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

Unless otherwise clear by the context, each reference to CCK2R is a reference to both CCK2R and CCK2i4svR.

II. Conjugates

The present invention is based on the discovery that useful therapeutic and imaging agents (active moieties) can be joined via a linker to benzazepine compounds (targeting ligands) that selectively bind CCK2R and the splice variant CCK2i4svR. Through diligent efforts the inventors developed linkers and identified locations on the targeting ligands to which the active moieties could be linked without interfering with the ability of the targeting ligands to selectively bind CCK2R and CCK2i4svR. The inventors have thus developed conjugates that comprise a targeting ligand linked to an active moiety, where the targeting ligand is a benzazepine compound that selectively binds to CCK2R and/or CCK2i4svR, and the active moiety is a therapeutic agent or imaging agent.

In particular, the invention is directed to conjugates comprising

wherein B is a targeting ligand, L is a polyvalent linker, D is an active moiety, and n is an integer of between 1 and 5. These conjugates target and bind CCK2R or CCK2i4svR, or both.

The conjugates are targeted to cells that express or over-express CCK2R or CCK2i4svR through the targeting ligand. Once delivered, the conjugates bind to the receptors. In certain embodiments, the conjugates remain on the surface of the cell for a period of time sufficient for detecting, imaging and/or diagnosis. In other embodiments, the conjugates are internalized into the cell by endogenous cellular mechanisms, such as endocytosis, for subsequent detection, imaging and/or diagnosis, or treatment. While attached to the surface or once internalized, the conjugates may remain intact or be decomposed, degraded, or otherwise altered to allow the release of the active moiety forming the conjugate. It is appreciated that in detecting, imaging and/or diagnostic configurations, the active moiety may remain attached to the conjugate or be released either before or after the conjugate has been internalized into the targeted cell. It is further appreciated that in therapeutic configurations, the active moiety is advantageously released from the conjugate once it has been internalized into the targeted cell, or alternatively may be therapeutically active while still bound to the targeting ligand.

In a certain aspect, the invention includes conjugates that have a binding constant $K_d$ of about 100 nM or less. In another aspect, the conjugates have a $K_d$ of about 75 nM or less. In another aspect, the conjugates have a $K_d$ of about 50 nM or less. In another aspect, the conjugates have a Kd of about 25 nM or less. In another embodiment, the conjugates described herein exhibit selectivity for CCK2R expressing or CCK2R over-expressing cells or tissues relative to normal tissues such as blood, lung, liver, spleen, duodenum, skin, muscle, bladder, and prostate, with at least 3-fold selectivity, or at least 5-fold selectivity. In one variation, the conjugates described herein exhibit selectivity for CCK2R expressing or CCK2R over-expressing cells or tissues relative to normal tissues with at least 10-fold selectivity. It is appreciated that the selectivity observed for imaging is indicative of the selectivity that may be observed in treating disease states responsive to the selective or specific elimination of cells or cell populations that express or over-express CCK2R. Based on this dual capability of CCK2R-targeted conjugates, it is anticipated that a CCK2R-targeted imaging agent may be employed to identify patients that will likely respond to a CCK2R-targeted therapeutic agent.

Examples of conjugates of the present invention include CRL-1, CRL-2, CRL-3, CRL-4, conjugate 17, conjugate 18, conjugate 19, conjugate 22, and conjugate 23.

CRL-1

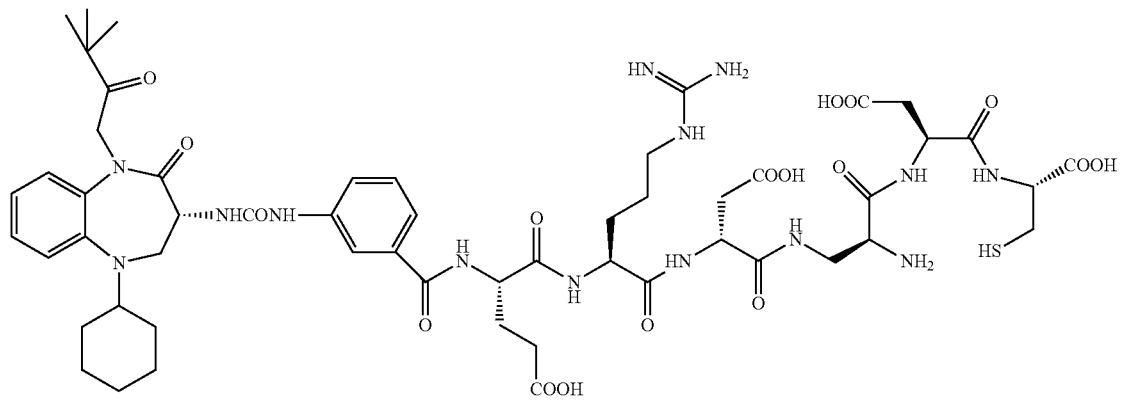

CRL-2

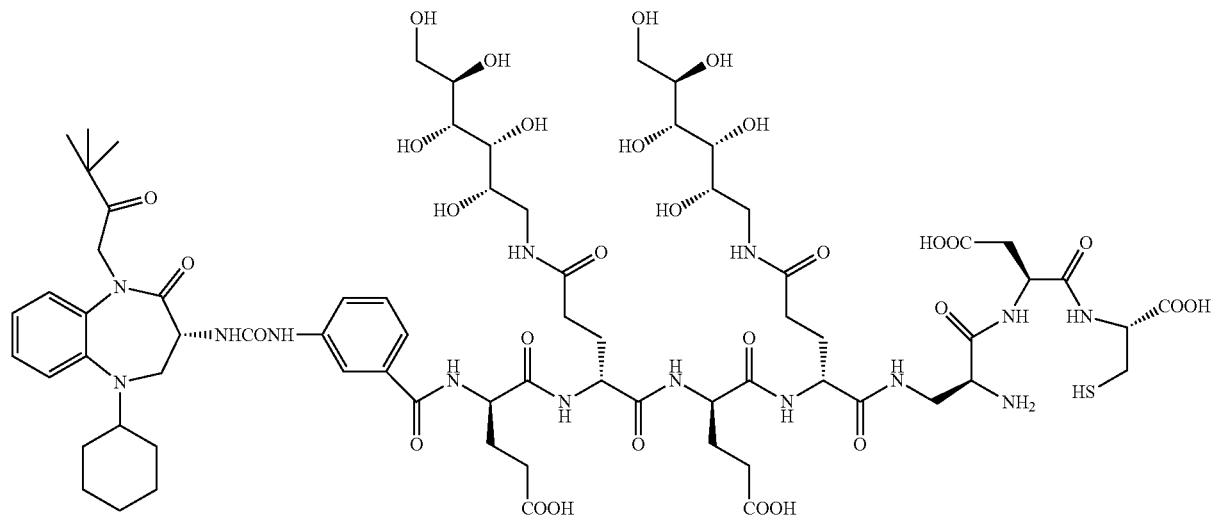

CRL-3

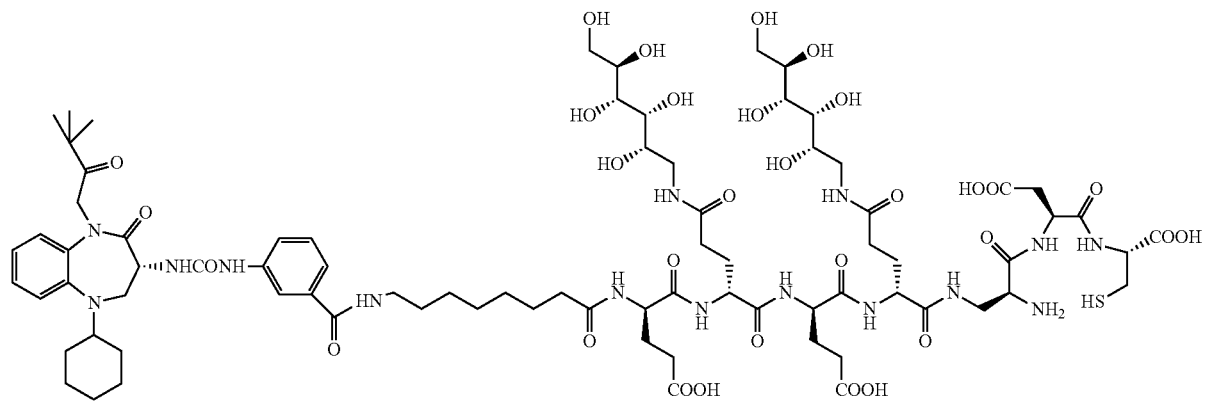

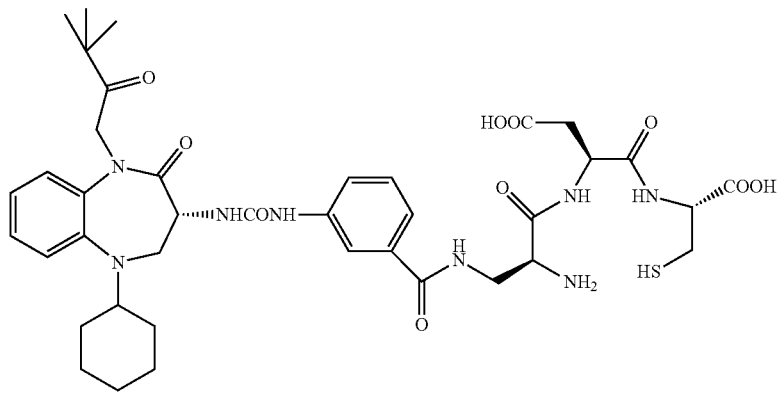
CRL-4
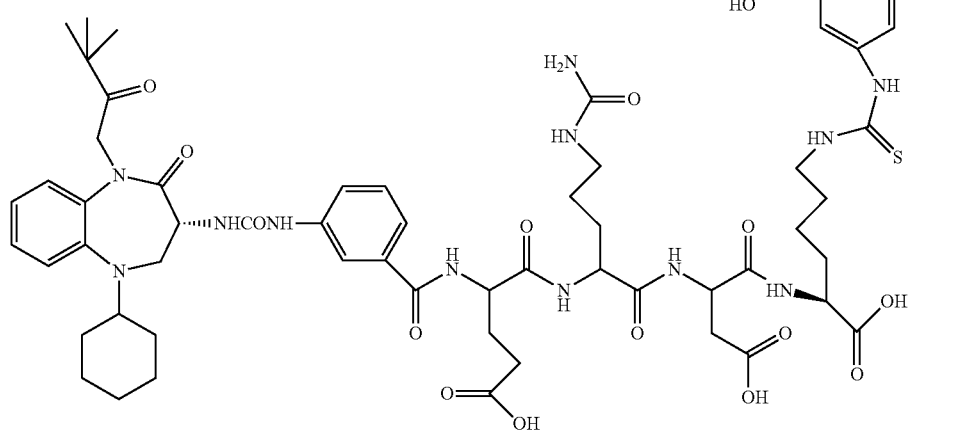
Conjugate 17
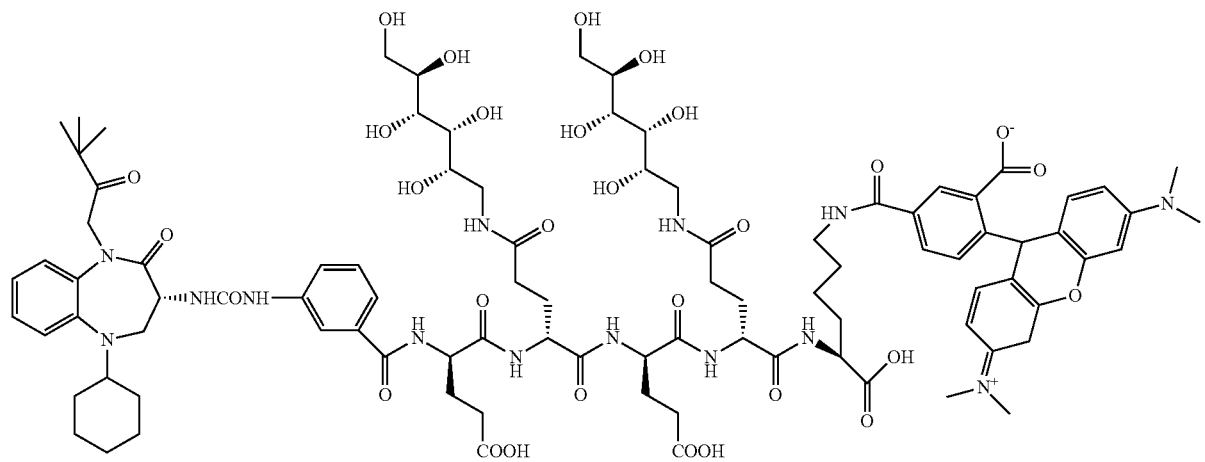
Conjugate 18

-continued
Conjugate 19
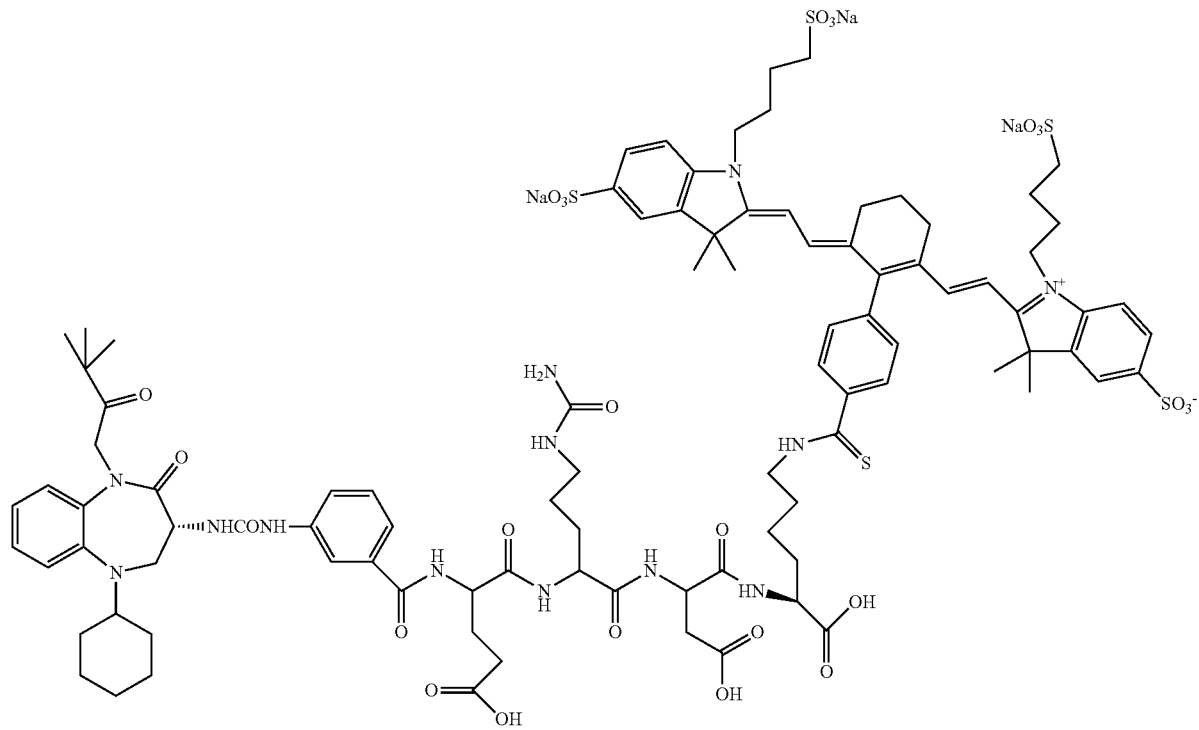
Conjugate 22
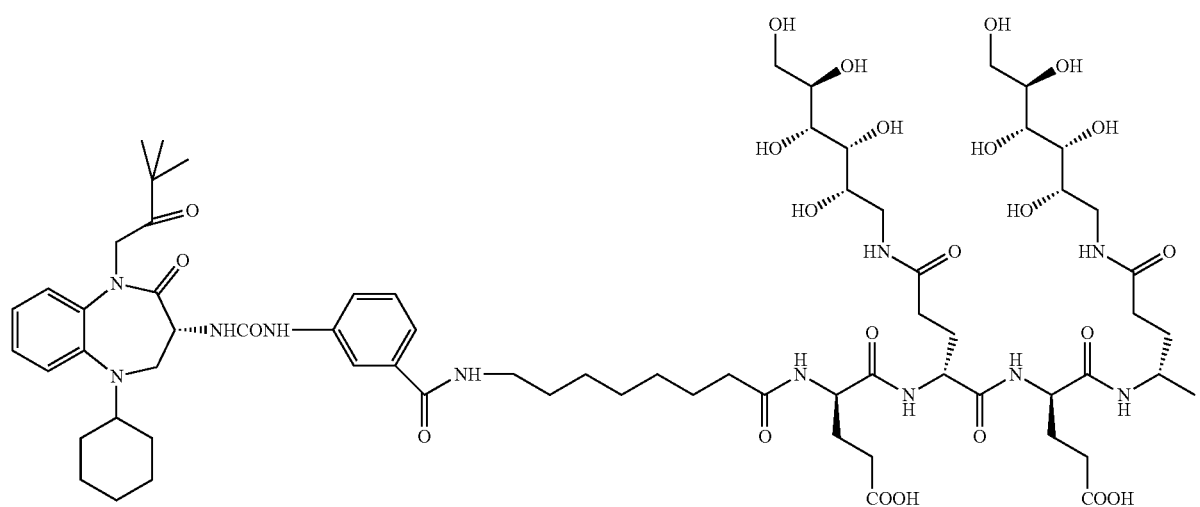
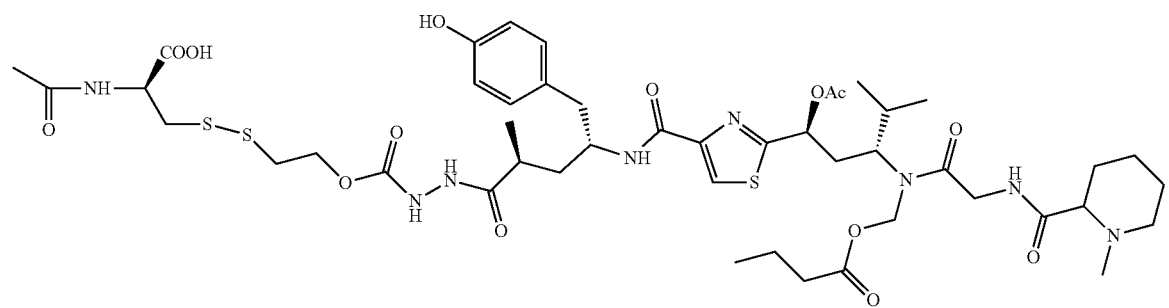

-continued
Conjugate 23
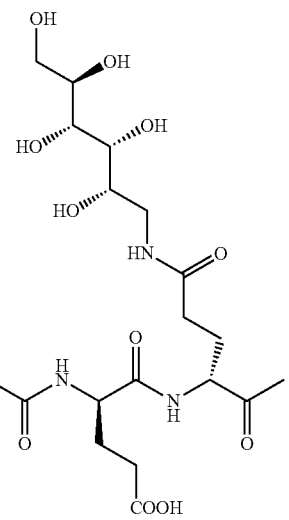
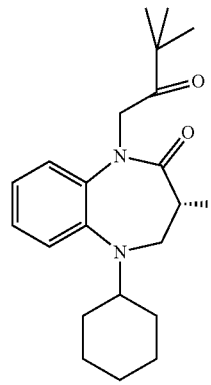
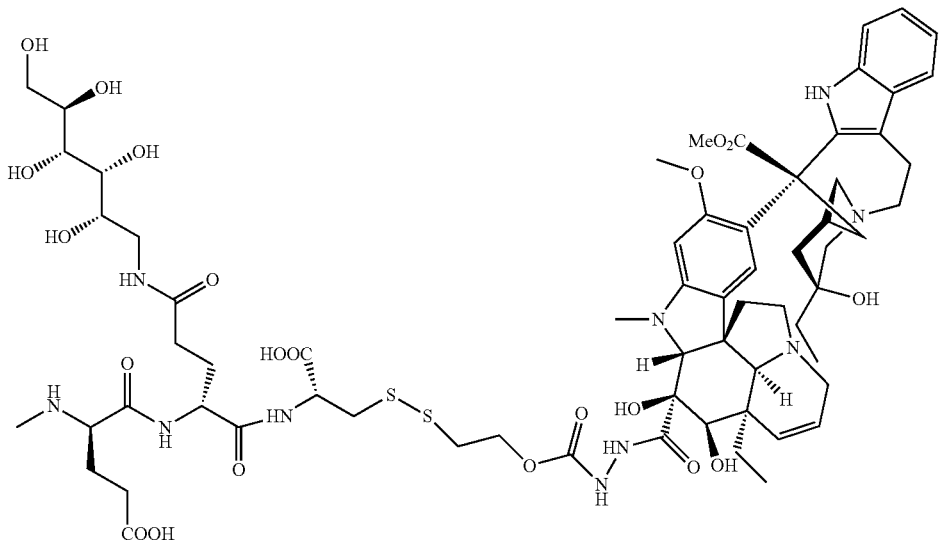

A. Target Ligands

The targeting ligands B of the conjugates are benzazepines where a benzene ring is fused to an azepine ring. An example of a targeting ligand that is used in the conjugates of the invention is the benzodiazepine Z-360

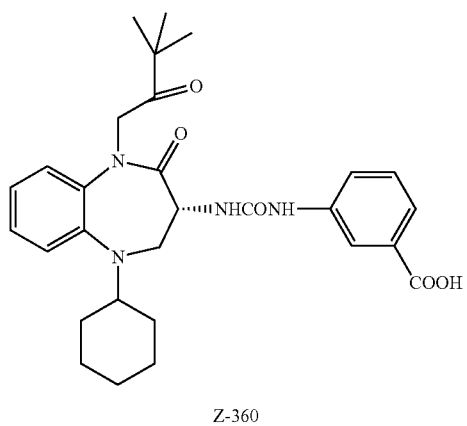

Z-360 and analogs, derivatives, salts and esters thereof.

The targeting ligands B also encompass the benzazepines of Formula I

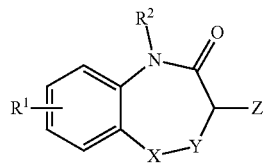

Formula I wherein:
the bond between X and Y is a single bond or a double bond;
$R^1$=H, $CH_3$ or heterocycle with $R^2$;
$R^2$=heterocycle with $R^1$, $CH_3$, $CH_2CON(Et)_2$, $CH_2COC(CH_3)_3$, $CH_2CONHC(CH_3)_3$,

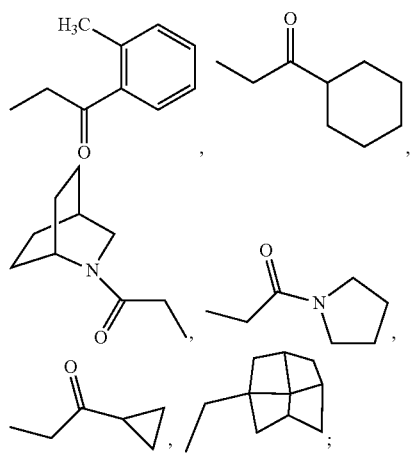

X=$CR^3$ or $NR^4$;
$R^3$=phenyl, cyclohexyl, $CH_3$, $CH_2$—$CH_3$,

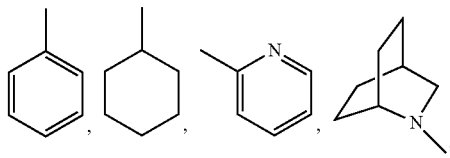

$R^4$=phenyl, cyclohexyl,

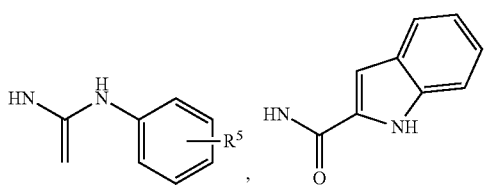

Y=$CH_2$, N (dashed=double bond), C=O;
Z=

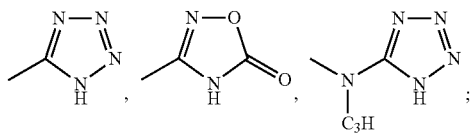

$R^5$=absent, phenyl, Cl, $CO_2H$, $CH_3$, $OCH_3$, $NHCH_3$, F, $SCH_2CO_2H$, $SCH_2CO_2Et$, and analogs, derivatives, salts and esters thereof.

B. Active Moieties

The invention takes advantage of the excellent properties of the conjugates. Due to their ability to carry a "payload", the targeting ligands can be labeled and still bind to cells that express one or both of CCK2R and CCK2i4svR. Upon binding of the receptors, the conjugates can be detected due to the properties of an imaging agent, or exert cytotoxic effects due to the properties of a therapeutic agent. The active moieties D of the conjugates of the present invention are thus therapeutic agents and imaging agents. The only limitation on suitable therapeutic agents and imaging agents is the requirement that they have a position on the molecule to which can be conjugated the linker L, or that they can be derivatized to possess such a position without losing the activity of the active moiety or compromising the ability of the targeting ligand to bind to its receptor with high affinity.

Therapeutic Agents

The therapeutic agents described herein function through any of a large number of mechanisms of action. Generally, therapeutic agents disrupt cellular mechanisms that are important for cell survival and/or cell proliferation and/or cause apoptosis. The therapeutic agents can be any compound known in the art which is cytotoxic, enhances tumor permeability, inhibits tumor cell proliferation, promotes apoptosis, decreases anti-apoptotic activity in target cells, is used to treat diseases caused by infectious agents, enhances an endogenous immune response directed to the pathogenic cells, or is useful for treating a disease state caused by any type of pathogenic cell.

Therapeutic agents suitable for use in accordance with this invention include adrenocorticoids and corticosteroids, alkylating agents, antiandrogens, antiestrogens, androgens, aclamycin and aclamycin derivatives, estrogens, antimetabolites such as cytosine arabinoside, purine analogs, pyrimidine analogs, and methotrexate, busulfan, carboplatin, chlorambucil, cisplatin and other platinum compounds, taxanes, such as tamoxiphen, taxol, paclitaxel, paclitaxel derivatives, Taxotere®, and the like, maytansines and analogs and derivatives thereof, cyclophosphamide, daunomycin, doxorubicin, rhizoxin, T2 toxin, plant alkaloids, prednisone, hydroxyurea, teniposide, mitomycins, discodermolides, microtubule inhibitors, epothilones, tubulysin (e.g., tubulysin B hydrazide), cyclopropyl benz[e]indolone, seca-cyclopropyl benz[e]indolone, 0-Ac-seca-cyclopropyl benz[e]indolone, bleomycin and any other antibiotic, nitrogen mustards, nitrosureas, vincristine, vinblastine, and analogs and derivative thereof such as desacetyl vinblastine monohydrazide, colchicine, colchicine derivatives, allocolchicine, thiocolchicine, trityl cysteine, Halicondrin B, dolastatins such as dolastatin 10, amanitins such as a-amanitin, camptothecin, irinotecan, and other camptothecin derivatives thereof, geldanamycin and geldanamycin derivatives, estramustine, nocodazole, MAP4, colcemid, inflammatory and proinflammatory agents, peptide and peptidomimetic signal transduction inhibitors, and any other art-recognized drug or toxin. Other drugs that can be used in accordance with the invention include penicillins, dinitrophenol, fluorescein, CpG oligonucleotides, staurosporine and othe kinase inhibitors, Sutent, resiquimod and other Toll-like receptor agonists, cephalosporins, vancomycin, erythromycin, clindamycin, rifampin, chloramphenicol, aminoglycoside antibiotics, gentamicin, amphotericin B, acyclovir, trifluridine, ganciclovir, zidovudine, amantadine, ribavirin, and any other art-recognized antimicrobial compound. The only limitation on suitable therapeutic agents is the requirement that they have a position on the molecule that can be conjugated to the linker L, or that they can be derivatized to possess such a position. Illustrative therapeutic agents are described in U.S. patent application publication nos. US 20050002942, US 20010031252, and US 20030086900, the disclosures of each of which are incorporated herein by reference in their entireties.

Specific sub-groups of therapeutic agents include, but are not limited to, radio-therapeutic agents, immunotherapeutic agents, photodynamic therapy agents and chemotherapeutic agents. The skilled artisan will understand that there is a wide variety of radio-therapeutics that will be suitable for use in the conjugates of the present invention. Suitable examples include, but are not limited to, $^{90}Y$, $^{131}I$, $^{177}Lu$, $^{67}Cu$, $^{111}In$, $^{186}Re$, $^{211}At$, and $^{223}Ra$.

The skilled artisan will also understand that there is a wide variety of chemotherapeutics that will be suitable for use in the conjugates of the present invention. Suitable examples include, but are not limited to, tubulysin B hydrazide and desacetyl vinblastine monohydrazide, calicheamycin, auristatin, maytansinoids and any other cytotoxic agent with $IC_{50}$ value below 10 nM.

It should also be appreciated that the ligand can be used to target a nanomedicines or nanoparticle, including but not limited to a liposome, a lipoplex, a polyplex, a dendrimer, a polymer, a nanoparticle, or a virus. It should further be recognized that the aforementioned particles might serve as carriers for DNA, RNA, siRNA, peptides, proteins, and other biologics.

Imaging Agents

Imaging agents suitable for use in the conjugates of the invention include, but are not limited to, radio-imaging agents, optical imaging agents, PET imaging agents, MRI contrast agents, CT contrast agents, and FRET imaging agents, and other agents that may be used to detect or visualize a tumor, cancer or transformed cell, whether in vitro, in vivo and ex vivo. Illustrative imaging agents are described in U.S. patent application publication no. US 20040033195 and international patent application publication no. WO 03/097647, the disclosures of each of which are incorporated herein by reference in their entireties.

Applications for conjugates comprising radio-imaging agents include and may not be limited to diagnosis of disease and or locating metastatic disease, detecting disease recurrence following surgery, monitoring response to therapy, development of a radio-therapeutic conjugate and selecting patients for subsequent CCK2R targeted therapy. Radio-imaging agents include radioactive isotopes, such as a radioactive isotope of a metal, coordinated to a chelating group. Illustrative radioactive metal isotopes include technetium, rhenium, gallium, gadolinium, indium, copper, and the like, including isotopes $^{111}In$, $^{99m}Tc$, $^{64}Cu$, $^{67}Cu$, $^{67}Ga$, $^{68}Ga$, and the like, or they may include radionuclides that are effective in radiotherapy. Additional illustrative examples of radionuclide imaging agents are described in U.S. Pat. No. 7,128,893, the disclosure of which is incorporated herein by reference in its entirety.

Illustratively, the following chelating groups are described that can be used with the radio-imaging agents:

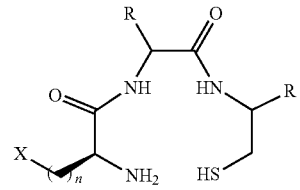

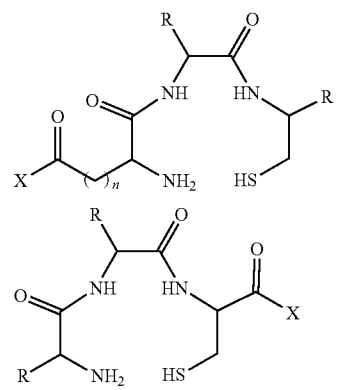

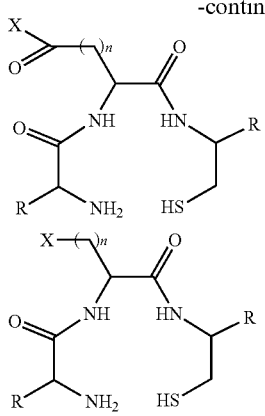

where X is oxygen, nitrogen, or sulfur, and where X is attached to linker L, and n is an integer from 1 to about 5.

Additional illustrative chelating groups are tripeptide or tetrapeptides, including but not limited to tripeptides having the formula:

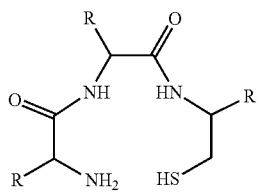

wherein R is independently selected in each instance from H, alkyl, heteroalkyl, cycloalkyl, heterocyclyl, alkenyl, alkynyl, aryl, heteroaryl, arylalkyl, heteroarylalkyl, and the like, each of which is optionally substituted. It is to be understood that one R includes a heteroatom, such as nitro, oxygen, or sulfur, and is the point of attachment of linker L.

Applications for conjugates comprising optical imaging agents include locating and resecting large tumor masses, delineation of normal and malignant tissue, intraoperative detection of sentinel lymph nodes, and fluorescent probe for minimally invasive laparoscopic procedures as an alternative to second look surgery. The skilled artisan will also understand that there is a wide variety of optical imaging agents that will be suitable for use in the conjugates of the present invention. The only limitations on suitable optical imaging agents is the requirement that they have a position on the molecule to which can be conjugated the linker L, or that they can be derivatized to possess such a position. Examples include, but are not limited to, Oregon Green fluorescent agents, including but not limited to Oregon Green 488, Oregon Green 514, and the like, AlexaFluor fluorescent agents, including but not limited to AlexaFluor 488, AlexaFluor 647, and the like, fluorescein, and related analogs, BODIPY fluorescent agents, including but not limited to BODIPY F1, BODIPY 505, 50456, and the like, rhodamine fluorescent agents, including but not limited to tetramethylrhodamine, and the like, near infra-red fluorescent agents, including but not limited to DyLight 680, DyLight 800, 800CW, LS288, 50456, indocyanine green and the like, Texas Red, phycoerythrin, and others. Illustrative optical imaging agents are shown in the following general structure:

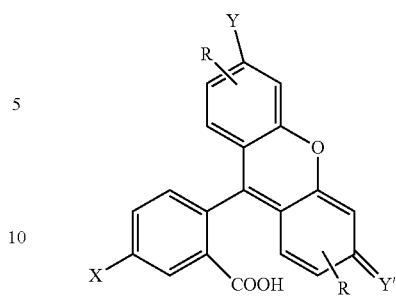

where X is oxygen, nitrogen, or sulfur, and where X is attached to linker L; Y is ORa, NRa$_2$, or NRa$_{3+}$; and Y' is O, NRa, or NRa$_{2+}$; where each R is independently selected in each instance from H, fluoro, sulfonic acid, sulfonate, and salts thereof, and the like; and Ra is hydrogen or alkyl.

According to another aspect, illustrative optical imaging agents are shown in the following general structure:

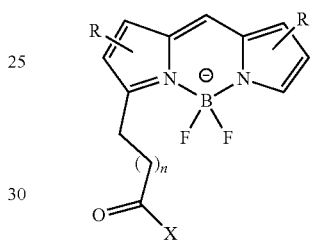

where X is oxygen, nitrogen, or sulfur, and where X is attached to linker L; and each R is independently selected in each instance from H, alkyl, heteroalkyl, and the like; and n is an integer from 0 to about 4.

The skilled artisan will also understand that there is a wide variety of PET imaging agents and FRET imaging agents that will be suitable for use in the conjugates of the present invention. The only limitations on suitable PET and FRET imaging agents is the requirement that they have a position on the molecule to which can be conjugated the linker L, or that they can be derivatized to possess such a position. Examples of PET imaging agents include, but are not limited to, $^{18}$F, $^{11}$C, $^{64}$Cu, $^{65}$Cu, and the like. Examples of FRET imaging agents include, but are not limited to, $^{64}$eu, $^{65}$eu, and the like. It appreciated that in the case of $^{18}$F and $^{11}$C, the imaging isotope may be present on any part of the linker, or alternatively may be present on a structure attached to the linker. For example in the case of $^{18}$F, fluoroaryl groups, such as fluorophenyl, difluorophenyl, fluoronitrophenyl, and the like are described. For example in the case of $^{11}$C, alkyl and alkyl aryl are described.

Exemplary optical imaging agents include, but are not limited to, fluorescein (FITC), rhodamine, LS288, 50456, IR800CW, or another near infrared dye.

C. Linkers

The targeting ligand B, or analog or derivative thereof, is covalently attached to the polyvalent linker L, and the active moiety D, or analog or derivative thereof, is also covalently attached to the polyvalent linker L. Exemplary linkers include, but are not limited to, a hydrophilic linkers comprised of charged or polar amino acids, sugars or sugar-containing oligomers, and hydrophilic polymers such as polyethylene glycol.

In a first embodiment, the linker L is L1, L2 or L3
L1: HN-Glu-Arg-Asp-CO
L2: HN-Glu-PS-Glu-PS-CO
L3: HN-Octanoyl-Glu-PS-Glu-PS-CO
wherein PS is the following formula

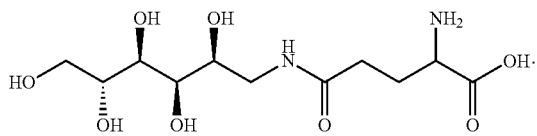

The linkers used in the production of the conjugates may also comprise one or more spacer linkers and/or one or more releasable linkers, and combinations thereof, in any order. It is appreciated that spacer linkers may included when predetermined lengths are selected for separating targeting ligand from the active moiety. It is also appreciated that in certain configurations, releasable linkers may be included. For example, as described herein in one embodiment, the conjugates may be used to deliver therapeutic agents for treating cancer or other diseases involving pathogenic cells. In such embodiments, it is appreciated that once delivered, the therapeutic agent is desirably released from the conjugate.

In one variation, releasable linkers, and optional spacer linkers are covalently bonded to each other to form the linker. In another variation, a releasable linker is directly attached to the active moiety, or analog or derivative thereof. In another variation, a releasable linker is directly attached to the targeting ligand. In another variation, either or both the targeting ligand and the active moiety, or analog or derivative thereof, is attached to a releasable linker through one or more spacer linkers. In another variation, each of the targeting ligand and the active moiety, or analog or derivative thereof, is attached to a releasable linker, each of which may be directly attached to each other, or covalently attached through one or more spacer linkers.

From the foregoing, it should be appreciated that the arrangement of the targeting ligand, and the active moieties, or analogs or derivatives thereof, and the various releasable and optional spacer linkers may be varied widely. In one aspect, the targeting ligand and the active moiety, and the various releasable and optional spacer linkers are attached to each other through heteroatoms, such as nitrogen, oxygen, sulfur, phosphorus, silicon, and the like. In variations, the heteroatoms, excluding oxygen, may be in various states of oxidation, such as N(OH), S(O), S(O)$_2$, P(O), P(O)$_2$, P(O)$_3$, and the like. In other variation, the heteroatoms may be grouped to form divalent radicals, such as for example hydroxylamines, hydrazines, hydrazones, sulfonates, phosphinates, phosphonates, and the like, including radicals of the formulae —(NHR$_1$NHR$_2$)—, —SO—, —(SO$_2$)—, and —N(R$_3$)O—, wherein R$_1$, R$_2$, and R$_3$ are each independently selected from hydrogen, alkyl, aryl, arylalkyl, substituted aryl, substituted arylalkyl, heteroaryl, substituted heteroaryl, and alkoxyalkyl. In another variation, more than one targeting ligand is attached to the polyvalent linker. In another variation, more than one active moiety is attached to the polyvalent linker. In another variation, more than one targeting ligand and more than one active moiety is attached to the polyvalent linker.

It is appreciated that the arrangement and/or orientation of the various hydrophilic linkers may be in a linear or branched fashion, or both. For example, the hydrophilic linkers may form the backbone of the linker forming the conjugate between the targeting ligand and the active moiety. Alternatively, the hydrophilic portion of the linker may be pendant to or attached to the backbone of the chain of atoms connecting the targeting ligand to the active moiety. In this latter arrangement, the hydrophilic portion may be proximal or distal to the backbone chain of atoms.

In another embodiment, the linker is more or less linear, and the hydrophilic groups are arranged largely in a series to form a chain-like linker in the conjugate. Said another way, the hydrophilic groups form some or all of the backbone of the linker in this linear embodiment.

In another embodiment, the linker is branched with hydrophilic groups. In this branched embodiment, the hydrophilic groups may be proximal to the backbone or distal to the backbone. In each of these arrangements, the linker is more spherical or cylindrical in shape.

In one variation, the linker is shaped like a bottle-brush. In one aspect, the backbone of the linker is formed by a linear series of amides, and the hydrophilic portion of the linker is formed by a parallel arrangement of branching side chains, such as by connecting monosaccharides, sulfonates, and the like, and derivatives and analogs thereof.

It is understood that the linker may be neutral or ionizable under certain conditions, such as physiological conditions encountered in vivo. For ionizable linkers, under the selected conditions, the linker may deprotonate to form a negative ion, or alternatively become protonated to form a positive ion. It is appreciated that more than one deprotonation or protonation event may occur. In addition, it is understood that the same linker may deprotonate and protonate to form inner salts or zwitterionic compounds.

In another embodiment, the hydrophilic spacer linkers are neutral, i.e. under physiological conditions, the linkers do not significantly protonate nor deprotonate. In another embodiment, the hydrophilic spacer linkers may be protonated to carry one or more positive charges. It is understood that the protonation capability is condition dependent. In one aspect, the conditions are physiological conditions, and the linker is protonated in vivo. In another embodiment, the spacers include both regions that are neutral and regions that may be protonated to carry one or more positive charges. In another embodiment, the spacers include both regions that may be deprotonated to carry one or more negative charges and regions that may be protonated to carry one or more positive charges. It is understood that in this latter embodiment that zwitterions or inner salts may be formed.

In one aspect, the regions of the linkers that may be deprotonated to carry a negative charge include carboxylic acids, such as aspartic acid, glutamic acid, and longer chain carboxylic acid groups, and sulfuric acid esters, such as alkyl esters of sulfuric acid. In another aspect, the regions of the linkers that may be protonated to carry a positive charge include amino groups, such as polyaminoalkylenes including ethylene diamines, propylene diamines, butylene diamines and the like, and/or heterocycles including pyrollidines, piperidines, piperazines, and other amino groups, each of which is optionally substituted. In another embodiment, the regions of the linkers that are neutral include poly hydroxyl groups, such as sugars, carbohydrates, saccharides, inositols, and the like, and/or polyether groups, such as polyoxyalkylene groups including polyoxyethylene, polyoxypropylene, and the like.

In one embodiment, the hydrophilic spacer linkers described herein include are formed primarily from carbon, hydrogen, and oxygen, and have a carbon/oxygen ratio of about 3:1 or less, or of about 2:1 or less. In one aspect, the hydrophilic linkers described herein include a plurality of ether functional groups. In another aspect, the hydrophilic linkers described herein include a plurality of hydroxyl functional groups. Illustrative fragments that may be used to form such linkers include polyhydroxyl compounds such as carbohydrates, polyether compounds such as polyethylene glycol units, and acid groups such as carboxyl and alkyl sulfuric acids. In one variation, oligoamide spacers, and the like may also be included in the linker.

In one illustrative embodiment, conjugates of the present invention include linkers having predetermined length and diameter dimensions. In one aspect, linkers are described herein that satisfy one or more minimum length requirements, or a length requirement falling within a predetermined range. In another aspect, satisfaction of a minimum length requirement may be understood to be determined by computer modeling of the extended conformations of linkers. In another aspect, satisfaction of a minimum length requirement may be understood to be determined by having a certain number of atoms, whether or not substituted, forming a backbone chain of atoms connecting the target ligand with the active moiety. In another embodiment, the backbone chain of atoms is cyclized with another divalent fragment. In another aspect, linkers are described herein that satisfy one or more maximum or minimum diameter requirements. In another aspect, satisfaction of a maximum or minimum diameter requirement may be understood to be determined by computer modeling of various conformations of linkers modeled as the space-filling, CPK, or like configurations. In another aspect, satisfaction of a maximum or minimum diameter requirement may be understood to be apply to one or more selected portions of the linker, for example the portion of the linker proximal to the targeting ligand, or the portion of the linker proximal to the active moiety, and the like. In another aspect, linkers are described herein that satisfy one or more chemical composition requirements, such as linkers that include one or more polar groups that may positively interact with the one or more side chains found in the CCK2R receptor. In one variation, linkers are described herein that satisfy one or more chemical composition requirements, such as linkers that include one or more non-polar groups that may positively interact with the CCK2R receptor.

In another embodiment, linkers are described that include at least one releasable linker. In one variation, linkers are described that include at least two releasable linkers. In another variation, linkers are described that include at least one self-immolative linker. In another variation, linkers are described that include at least one releasable linker that is not a disulfide. In another embodiment, linkers are described that do not include a releasable linker.

It is appreciated that releasable linkers may be used when the active moiety to be delivered is advantageously liberated from the targeting ligand-linker conjugate so that free active moiety will have the same or nearly the same effect at the target as it would when administered without the targeting provided by the conjugates described herein. In another embodiment, the linker is a non-releasable linker. It is appreciated that non-releasable linkers may be used when the active moiety is advantageously retained by the targeting ligand-linker conjugate, such as in imaging, diagnostic, uses of the conjugates described herein.

It is to be understood that the choice of a releasable linker or a non-releasable linker may be made independently for each application or configuration of the conjugates, without limiting the invention described herein.

It is to be further understood that the linkers described herein comprise various atoms, chains of atoms, functional groups, and combinations of functional groups. Where appropriate in the present disclosure, the linker may be referred to by the presence of spacer linkers, releasable linkers, and heteroatoms. However, such references are not to be construed as limiting the definition of the linkers described herein.

The linker comprising spacer and/or releasable linkers (i.e., cleavable linkers) can be any biocompatible linker. The releasable or cleavable linker can be, for example, a linker susceptible to cleavage under the reducing or oxidizing conditions present in or on cells, a pH-sensitive linker that may be an acid-labile or base-labile linker, or a linker that is cleavable by biochemical or metabolic processes, such as an enzyme-labile linker. According to at least one embodiment, the spacer and/or releasable linker comprises about 1 to about 30 atoms, or about 2 to about 20 atoms. Lower molecular weight linkers (i.e., those having an approximate molecular weight of about 30 to about 300) are also described. Precursors to such linkers may be selected to have either nucleophilic or electrophilic functional groups, or both, optionally in a protected form with a readily cleavable protecting group to facilitate their use in synthesis of the intermediate species.

The term "releasable linker" as used herein refers to a linker that includes at least one bond that can be broken under physiological conditions (e.g., a pH-labile, acid-labile, redox-labile, or enzyme-labile bond). The cleavable bond or bonds may be present in the interior of a cleavable linker and/or at one or both ends of a cleavable linker. It should be appreciated that such physiological conditions resulting in bond breaking include standard chemical hydrolysis reactions that occur, for example, at physiological pH, or as a result of compartmentalization into a cellular organelle such as an endosome having a lower pH than cytosolic pH. Illustratively, the bivalent linkers described herein may undergo cleavage under other physiological or metabolic conditions, such as by the action of a glutathione mediated mechanism. It is appreciated that the lability of the cleavable bond may be adjusted by including functional groups or fragments within the bivalent linker that are able to assist or facilitate such bond breakage, also termed anchimeric assistance. The lability of the cleavable bond can also be adjusted by, for example, substitutional changes at or near the cleavable bond, such as including alpha branching adjacent to a cleavable disulfide bond, increasing the hydrophobicity of substituents on silicon in a moiety having a silicon-oxygen bond that may be hydrolyzed, homologating alkoxy groups that form part of a ketal or acetal that may be hydrolyzed, and the like. In addition, it is appreciated that additional functional groups or fragments may be included within the bivalent linker that are able to assist or facilitate additional fragmentation of the conjugates after bond breaking of the releasable linker.

In another embodiment, the linker includes radicals that form one or more spacer linkers and/or releasable linkers that are taken together to form the linkers described herein having certain length, diameter, and/or functional group requirements.

Another illustrative embodiment of the linkers described herein, include releasable linkers that cleave under the conditions described herein by a chemical mechanism involving beta elimination. In one aspect, such releasable linkers include beta-thio, betahydroxy, and beta-amino substituted carboxylic acids and derivatives thereof, such as esters, amides, carbonates, carbamates, and ureas. In another aspect, such releasable linkers include 2- and 4-thioarylesters, carbamates, and carbonates.

It is to be understood that releasable linkers may also be referred to by the functional groups they contain, illustratively such as disulfide groups, ketal groups, and the like, as described herein. Accordingly, it is understood that a cleavable bond can connect two adjacent atoms within the releasable linker and/or connect other linkers, or the targeting ligand, or the active moiety, as described herein, at either or both ends of the releasable linker. In the case where a cleavable bond connects two adjacent atoms within the releasable linker, following breakage of the bond, the releasable linker is broken into two or more fragments. Alternatively, in the case where a cleavable bond is between the releasable linker and another moiety, such as an additional heteroatom, a spacer linker, another releasable linker, the active moiety, or analog or derivative thereof, or the targeting ligand, or analog or derivative thereof, following breakage of the bond, the releasable linker is separated from the other moiety.

In another embodiment, the releasable and spacer linkers may be arranged in such a way that subsequent to the cleavage of a bond in the bivalent linker, released functional groups anchimerically assist the breakage or cleavage of additional bonds, as described above.

An illustrative embodiment of such a bivalent linker or portion thereof includes compounds having the formula:

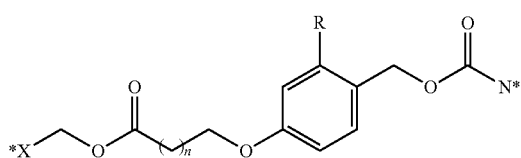

where X is an heteroatom, such as nitrogen, oxygen, or sulfur, n is an integer selected from 0, 1, 2, and 3, R is hydrogen, or a substituent, including a substituent capable of stabilizing a positive charge inductively or by resonance on the aryl ring, such as alkoxy, and the like, and the symbol (*) indicates points of attachment for additional spacer or releasable linkers, or heteroatoms, forming the bivalent linker, or alternatively for attachment of the active moiety, or analog or derivative thereof, or the targeting ligand, or analog or derivative thereof. It is appreciated that other substituents may be present on the aryl ring, the benzyl carbon, the alkanoic acid, or the methylene bridge, including but not limited to hydroxy, alkyl, alkoxy, alkylthio, halo, and the like. Assisted cleavage may include mechanisms involving benzylium intermediates, benzyne intermediates, lactone cyclization, oxonium intermediates, beta-elimination, and the like. It is further appreciated that, in addition to fragmentation subsequent to cleavage of the releasable linker, the initial cleavage of the releasable linker may be facilitated by an anchimerically-assisted mechanism.

In this embodiment, the hydroxyalkanoic acid, which may cyclize, facilitates cleavage of the methylene bridge, by for example an oxonium ion, and facilitates bond cleavage or subsequent fragmentation after bond cleavage of the releasable linker. Alternatively, acid catalyzed oxonium ion-assisted cleavage of the methylene bridge may begin a cascade of fragmentation of this illustrative releasable linker, or fragment thereof. Alternatively, acid-catalyzed hydrolysis of the carbamate may facilitate the beta elimination of the hydroxyalkanoic acid, which may cyclize, and facilitate cleavage of methylene bridge, by for example an oxonium ion. It is appreciated that other chemical mechanisms of bond breakage or cleavage under the metabolic, physiological, or cellular conditions described herein may initiate such a cascade of fragmentation. It is appreciated that other chemical mechanisms of bond breakage or cleavage under the metabolic, physiological, or cellular conditions described herein may initiate such a cascade of fragmentation.

Illustrative mechanisms for cleavage of the bivalent linkers described herein include the following 1,4 and 1,6 fragmentation mechanisms

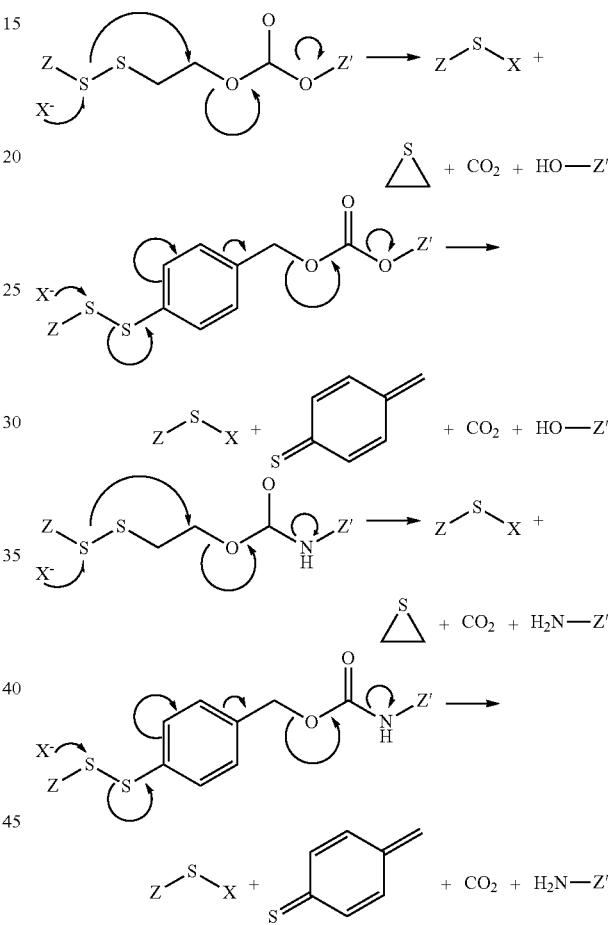

where X is an exogenous or endogenous nucleophile, glutathione, or bioreducing agent, and the like, and either of Z or Z' is a targeting ligand, or an active moiety, or either of Z or Z' is a targeting ligand, or an active moiety connected through other portions of the bivalent linker. It is to be understood that although the above fragmentation mechanisms are depicted as concerted mechanisms, any number of discrete steps may take place to effect the ultimate fragmentation of the bivalent linker to the final products shown. For example, it is appreciated that the bond cleavage may also occur by acid catalyzed elimination of the carbamate moiety, which may be anchimerically assisted by the stabilization provided by either the aryl group of the beta sulfur or disulfide illustrated in the above examples. In those variations of this embodiment, the releasable linker is the carbamate moiety. Alternatively, the fragmentation may be initiated by a nucleophilic attack on the disulfide group, causing cleavage to form a thiolate. The thiolate may intermolecularly displace a carbonic acid or carbamic acid moiety and form the corresponding thiacyclopropane. In the case of the benzyl-containing bivalent linkers, following an illustrative breaking of the disulfide bond, the resulting phenyl thiolate may further fragment to release a carbonic acid or carbamic acid moiety by forming a resonance stabilized intermediate. In any of these cases, the releaseable nature of the illustrative bivalent linkers described herein may be realized by whatever mechanism may be relevant to the chemical, metabolic, physiological, or biological conditions present.

Other illustrative mechanisms for bond cleavage of the releasable linker include oxonium-assisted cleavage as follows:

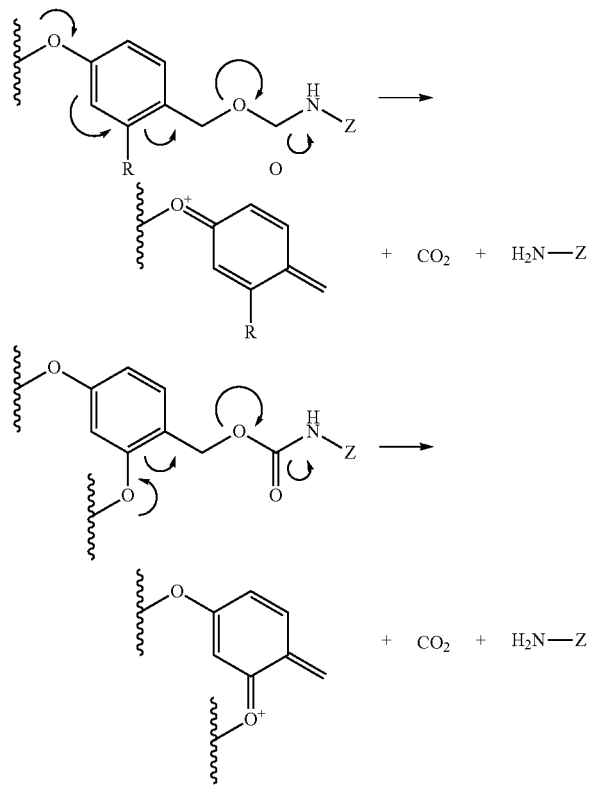

where Z is the targeting ligand, or analog or derivative thereof, or the active moiety, or analog or derivative thereof, or each is a targeting ligand or active moiety in conjunction with other components of the polyvalent linker, such as an active moiety or targeting ligand including one or more spacer linkers and/or other releasable linkers. In this embodiment, acid-catalyzed elimination of the carbamate leads to the release of $CO_2$ and the nitrogen-containing moiety attached to Z, and the formation of a benzyl cation, which may be trapped by water, or any other Lewis base.

According to at least one embodiment, the releasable linker includes a disulfide.

In another embodiment, the releasable linker may be a divalent radical comprising alkyleneaziridin-1-yl, alkylenecarbonylaziridin-1-yl, carbonylalkylaziridin-1-yl, alkylenesulfoxylaziridin-1-yl, sulfoxylalkylaziridin-1-yl, sulfonylalkylaziridin-1-yl, or alkylenesulfonylaziridin-1-yl, wherein each of the releasable linkers is optionally substituted with a substituent $X^2$, as defined below.

Additional illustrative releasable linkers include methylene, 1-alkoxyalkylene, 1-alkoxycycloalkylene, 1-alkoxyalkylenecarbonyl, 1-alkoxycycloalkylenecarbonyl, carbonylarylcarbonyl, carbonyl(carboxyaryl)carbonyl, carbonyl (biscarboxyaryl)carbonyl, haloalkylenecarbonyl, alkylene (dialkylsilyl), alkylene(alkylarylsilyl), alkylene(diarylsilyl), (dialkylsilyl)aryl, (alkylarylsilyl)aryl, (diarylsilyl)aryl, oxycarbonyloxy, oxycarbonyloxyalkyl, sulfonyloxy, oxysulfonylalkyl, iminoalkylidenyl, carbonylalkylideniminyl, aminocycloalkylidenyl, carbonylcycloalkylideniminyl, alkylenethio, alkylenearylthio, and carbonylalkylthio, wherein each of the releasable linkers is optionally substituted with a substituent $X^2$, as defined below.

In the preceding embodiment, the releasable linker may include oxygen, and the releasable linkers can be methylene, 1-alkoxyalkylene, 1-alkoxycycloalkylene, 1-alkoxyalkylenecarbonyl, and 1-alkoxycycloalkylenecarbonyl, wherein each of the releasable linkers is optionally substituted with a substituent $X^2$, as defined below, and the releasable linker is bonded to the oxygen to form an acetal or ketal. Alternatively, the releasable linker may include oxygen, and the releasable linker can be methylene, wherein the methylene is substituted with an optionally-substituted aryl, and the releasable linker is bonded to the oxygen to form an acetal or ketal. Further, the releasable linker may include oxygen, and the releasable linker can be sulfonylalkyl, and the releasable linker is bonded to the oxygen to form an alkylsulfonate.

In another embodiment of the above releasable linker embodiment, the releasable linker may include nitrogen, and the releasable linkers can be aminoalkylidenyl, carbonylalkylideniminyl, iminocycloalkylidenyl, and carbonylcycloalkylideniminyl, wherein each of the releasable linkers is optionally substituted with a substituent $X^2$, as defined below, and the releasable linker is bonded to the nitrogen to form an hydrazone. In an alternate configuration, the hydrazone may be acylated with a carboxylic acid derivative, an orthoformate derivative, or a carbamoyl derivative to form various acylhydrazone releasable linkers.

Alternatively, the releasable linker may include oxygen, and the releasable linkers can be alkylene(dialkylsilyl), alkylene(alkylarylsilyl), alkylene(diarylsilyl), (dialkylsilyl)aryl, (alkylarylsilyl)aryl, and (diarylsilyl)aryl, wherein each of the releasable linkers is optionally substituted with a substituent $X^2$, as defined below, and the releasable linker is bonded to the oxygen to form a silanol.

In the above releasable linker embodiment, the active moiety can include a nitrogen atom, the releasable linker may include nitrogen, and the releasable linkers can be carbonylarylcarbonyl, carbonyl(carboxyaryl)carbonyl, carbonyl(biscarboxyaryl)carbonyl, and the releasable linker can be bonded to the heteroatom nitrogen to form an amide, and also bonded to the active moiety nitrogen to form an amide.

In the above releasable linker embodiment, the active moiety can include an oxygen atom, the releasable linker may include nitrogen, and the releasable linkers can be carbonylarylcarbonyl, carbonyll(carboxyaryl)carbonyl, carbonyl(biscarboxyaryl)carbonyl, and the releasable linker can form an amide, and also bonded to the active moiety oxygen to form an ester.

The substituents $X^2$ can be alkyl, alkoxy, alkoxyalkyl, hydroxy, hydroxyalkyl, amino, aminoalkyl, alkylaminoalkyl, dialkylaminoalkyl, halo, haloalkyl, sulfhydrylalkyl, alkylthioalkyl, aryl, substituted aryl, arylalkyl, substituted arylalkyl, heteroaryl, substituted heteroaryl, carboxy, carboxyalkyl, alkyl carboxylate, alkyl alkanoate, guanidinoalkyl, $R^4$ carbonyl, $R^5$-carbonylalkyl, $R^6$-acylamino, and $R^7$-acylaminoalkyl, wherein $R^4$ and $R^5$ are each independently selected from amino acids, amino acid derivatives, and peptides, and wherein $R^6$ and $R^7$ are each independently selected from amino acids, amino acid derivatives, and peptides.

In this embodiment the releasable linker can include nitrogen, and the substituent $X^2$ and the releasable linker can form a heterocycle. The heterocycles can be pyrrolidines, piperidines, oxazolidines, isoxazolidines, thiazolidines, isothiazolidines, pyrrolidinones, piperidinones, oxazolidinones, isoxazolidinones, thiazolidinones, isothiazolidinones, and succinimides.

In a specific embodiment, the linkers for use in the conjugates of the present invention include the following:

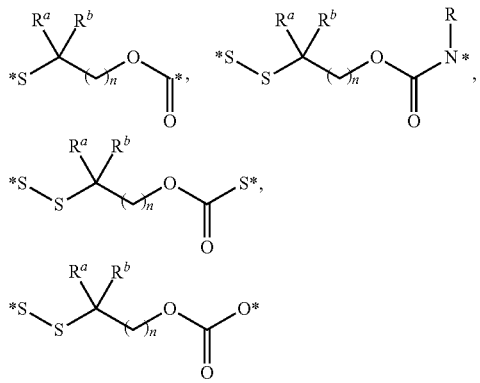

where n is an integer selected from 1 to about 4; $R^a$ and $R^b$ are each independently selected from the group consisting of hydrogen and alkyl, including lower alkyl such as $C_1$-$C_4$ alkyl that are optionally branched; or $R^a$ and $R^b$ are taken together with the attached carbon atom to form a carbocyclic ring; R is an optionally substituted alkyl group, an optionally substituted acyl group, or a suitably selected nitrogen protecting group; and (*) indicates interchangeable points of attachment for the targeting ligand and the active moiety.

In a further specific embodiment, the linkers for use in the conjugates of the present invention include the following:

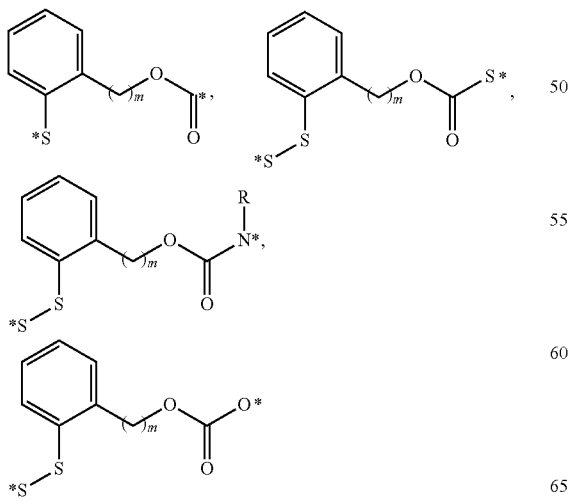

where m is an integer selected from 1 to about 4; R is an optionally substituted alkyl group, an optionally substituted acyl group, or a suitably selected nitrogen protecting group; and (*) indicates interchangeable points of attachment for the targeting ligand and the active moiety.

In an additional specific embodiment, the linkers for use in the conjugates of the present invention include the following:

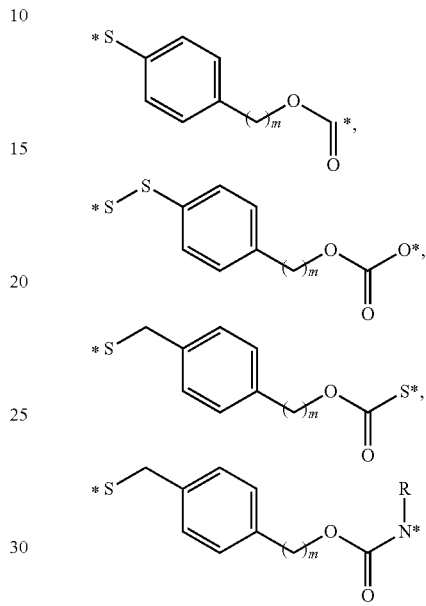

where m is an integer selected from 1 to about 4; R is an optionally substituted alkyl group, an optionally substituted acyl group, or a suitably selected nitrogen protecting group; and (*) indicates interchangeable points of attachment for the targeting ligand and the active moiety.

In a further additional specific embodiment, the linkers for use in the conjugates of the present invention include the following:

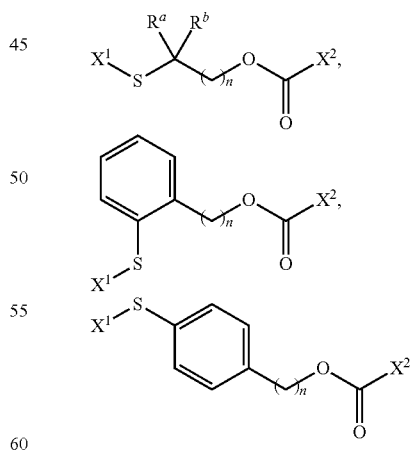

wherein n and m are each independently selected integers from 1 to about 4; $R^a$ and $R^b$ are each independently selected from the group consisting of hydrogen and alkyl, including lower alkyl such as $C_1$-$C_4$ alkyl that are optionally branched; or $R^a$ and $R^b$ are taken together with the attached carbon atom to form a carbocyclic ring; and $X^1$ and $X^2$ are each independently selected leaving groups that may be nucleophilically displaced by a targeting ligand, an active moiety, another bivalent linker, or another part of the conjugate.

Additional linkers and means for preparing the linkers of the preceding four embodiments are provided in US 2009/0203889 and WO 2006/012527, the disclosures of both of which are incorporated herein by reference in their entireties.

In another embodiment, the linker includes one or more spacer linkers. Such spacer linkers can be 1-alkylenesuccinimid-3-yl, optionally substituted with a substituent $X^1$, as defined below, and the releasable linkers can be methylene, 1-alkoxyalkylene, 1-alkoxycycloalkylene, 1-alkoxyalkylenecarbonyl, 1-alkoxycycloalkylenecarbonyl, wherein each of the releasable linkers is optionally substituted with a substituent $X^2$, as defined above, and wherein the spacer linker and the releasable linker are each bonded to the spacer linker to form a succinimid-1-ylalkyl acetal or ketal.

The spacer linkers can be carbonyl, thionocarbonyl, alkylene, cycloalkylene, alkylenecycloalkyl, alkyl enecarbonyl, cycloalkylenecarbonyl, carbonylalkylcarbonyl, 1-alkylenesuccinimid-3-yl, 1-(carbonylalkyl)succinimid-3-yl, alkylenesulfoxyl, sulfonyl alkyl, alkylenesulfoxylalkyl, alkylenesulfonylalkyl, carbonyltetrahydro-2H-pyranyl, carbonyltetrahydrofuranyl, 1-(carbonyltetrahydro-2H-pyranyl)succinimid-3-yl, and 1-(carbonyltetrahydrofuranyl)succinimid-3-yl, wherein each of the spacer linkers is optionally substituted with a substituent $X^1$ as defined below. In this embodiment, the spacer linker may include an additional nitrogen, and the spacer linkers can be alkylenecarbonyl, cycloalkylenecarbonyl, carbonylalkylcarbonyl, 1-(carbonylalkyl)succinimid-3-yl, wherein each of the spacer linkers is optionally substituted with a substituent $X^1$ as defined below, and the spacer linker is bonded to the nitrogen to form an amide. Alternatively, the spacer linker may include an additional sulfur, and the spacer linkers can be alkylene and cycloalkylene, wherein each of the spacer linkers is optionally substituted with carboxy, and the spacer linker is bonded to the sulfur to form a thiol. In another embodiment, the spacer linker can include sulfur, and the spacer linkers can be 1-alkylenesuccinimid-3-yl and 1-(carbonylalkyl)succinimid-3-yl, and the spacer linker is bonded to the sulfur to form a succinimid-3-ylthiol.

In an alternative to the above-described embodiments, the spacer linker can include nitrogen, and the releasable linker can be a divalent radical comprising alkyleneaziridin-1-yl, carbonylalkylaziridin-1-yl, sulfoxylalkylaziridin-1-yl, or sulfonylalkylaziridin-1-yl, wherein each of the releasable linkers is optionally substituted with a substituent $X^2$, as defined above. In this alternative embodiment, the spacer linkers can be carbonyl, thionocarbonyl, alkylenecarbonyl, cycloalkylenecarbonyl, carbonylalkylcarbonyl, 1-(carbonylalkyl)succinimid-3-yl, wherein each of the spacer linkers is optionally substituted with a substituent $X^1$ as defined below, and wherein the spacer linker is bonded to the releasable linker to form an aziridine amide.

The substituents $X^1$ can be alkyl, alkoxy, alkoxyalkyl, hydroxy, hydroxyalkyl, amino, aminoalkyl, alkylaminoalkyl, dialkylaminoalkyl, halo, haloalkyl, sulfhydrylalkyl, alkylthioalkyl, aryl, substituted aryl, arylalkyl, substituted arylalkyl, heteroaryl, substituted heteroaryl, carboxy, carboxyalkyl, alkyl carboxylate, alkyl alkanoate, guanidinoalkyl, $R^4$carbonyl, $R^5$-carbonylalkyl, $R^6$-acylamino, and $R^7$-acylaminoalkyl, wherein $R^4$ and $R^5$ are each independently selected from amino acids, amino acid derivatives, and peptides, and wherein $R^6$ and $R^7$ are each independently selected from amino acids, amino acid derivatives, and peptides. In this embodiment the spacer linker can include nitrogen, and the substituent $X^1$ and the spacer linker to which they are bound to form a heterocycle.

Additional illustrative spacer linkers include alkyleneamino-alkylenecarbonyl, alkylene-thio-(carbonylalkylsuccinimid-3-yl), and the like, as further illustrated by the following formulae:

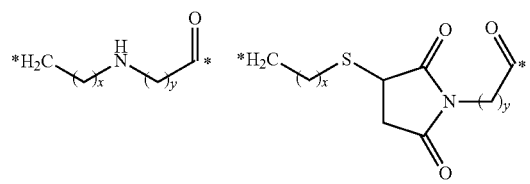

where the integers x and y are 1, 2, 3, 4, or 5.

In another embodiment, linkers that include hydrophilic regions are also described. In one aspect, the hydrophilic region of the linker forms part or all of a spacer linker included in the conjugates described herein. Illustrative hydrophilic spacer linkers are described in WO 2008/002993, published Dec. 31, 2008, the disclosure of which is incorporated herein by reference.

The term "cycloalkyl" as used herein includes molecular fragments or radicals comprising a bivalent chain of carbon atoms, a portion of which forms a ring. It is to be understood that the term cycloalkyl as used herein includes fragments and radicals attached at either ring atoms or non-ring atoms, such as, such as cyclopropyl, cyclohexyl, 3-ethylcyclopent-1-yl, cyclopropylethyl, cyclohexylmethyl, and the like.

The term "cycloalkylene" as used herein includes molecular fragments or radicals comprising a bivalent chain of carbon atoms, a portion of which forms a ring. It is to be understood that the term cycloalkyl as used herein includes fragments and radicals attached at either ring atoms or non-ring atoms, such as cycloprop-1,1-diyl, cycloprop-1,2-diyl, cyclohex-1,4-diyl, 3-ethylcyclopent-1,2-diyl, 1-methylenecyclohex-4-yl, and the like.

The terms "heteroalkyl" and "heteroalkylene" as used herein includes molecular fragments or radicals comprising monovalent and divalent, respectively, groups that are formed from a linear or branched chain of carbon atoms and heteroatoms, wherein the heteroatoms are selected from nitrogen, oxygen, and sulfur, such as alkoxyalkyl, alkyleneoxyalkyl, aminoalkyl, alkylaminoalkyl, alkyleneaminoalkyl, alkylthioalkyl, alkylenethioalkyl, alkoxyalkylaminoalkyl, alkylaminoalkoxyalkyl, alkyleneoxyalkylaminoalkyl, and the like.

The term "heterocyclyl" as used herein includes molecular fragments or radicals comprising a monovalent chain of carbon atoms and heteroatoms, wherein the heteroatoms are selected from nitrogen, oxygen, and sulfur, a portion of which, including at least one heteroatom, form a ring, such as aziridine, pyrrolidine, oxazolidine, 3-methoxypyrrolidine, 3-methylpiperazine, and the like. Accordingly, as used herein, heterocyclyl includes alkylheterocyclyl, heteroalkylheterocyclyl, heterocyclylalkyl, heterocyclylheteroalkyl, and the like. It is to be understood that the term heterocyclyl as used herein includes fragments and radicals attached at either ring atoms or non-ring atoms, such as tetrahydrofuran-2-yl, piperidin-1-yl, piperidin-4-yl, piperazin-1-yl, morpholin-1-yl, tetrahydrofuran-2-ylmethyl, piperidin-1-ylethyl, piperidin-4-ylmethyl, piperazin-1-ylpropyl, morpholin-1-ylethyl, and the like.

The term "aryl" as used herein includes molecular fragments or radicals comprising an aromatic mono or polycyclic ring of carbon atoms, such as phenyl, naphthyl, and the like.

The term "heteroaryl" as used herein includes molecular fragments or radicals comprising an aromatic mono or polycyclic ring of carbon atoms and at least one heteroatom selected from nitrogen, oxygen, and sulfur, such as pyridinyl, pyrimidinyl, indolyl, benzoxazolyl, and the like.

The term "substituted aryl" or "substituted heteroaryl" as used herein includes molecular fragments or radicals comprising aryl or heteroaryl substituted with one or more substituents, such as alkyl, heteroalkyl, halo, hydroxy, amino, alkyl or dialkylamino, alkoxy, alkylsulfonyl, aminosulfonyl, carboxylate, alkoxycarbonyl, aminocarbonyl, cyano, nitro, and the like. It is to be understood that the alkyl groups in such substituents may be optionally substituted with halo.

The term "iminoalkylidenyl" as used herein includes molecular fragments or radicals comprising a divalent radical containing alkylene as defined herein and a nitrogen atom, where the terminal carbon of the alkylene is double-bonded to the nitrogen atom, such as the formulae —(CH)=N—, —(CH$_2$)2(CH)=N—, —CH$_2$C(Me)=N—, and the like.

The term "amino acid" as used herein includes molecular fragments or radicals comprising an aminoalkylcarboxylate, where the alkyl radical is optionally substituted with alkyl, hydroxy alkyl, sulfhydrylalkyl, aminoalkyl, carboxyalkyl, and the like, including groups corresponding to the naturally occurring amino acids, such as serine, cysteine, methionine, aspartic acid, glutamic acid, and the like.

For example, and according to at least one embodiment, amino acid is a divalent radical having the general formula:

—N(R)—(CR'R")$q$—C(O)— where R is hydrogen, alkyl, acyl, or a suitable nitrogen protecting group, R' and R" are hydrogen or a substituent, each of which is independently selected in each occurrence, and q is an integer such as 1, 2, 3, 4, or 5. Illustratively, R' and/or R" independently correspond to, but are not limited to, hydrogen or the side chains present on naturally occurring amino acids, such as methyl, benzyl, hydroxymethyl, thiomethyl, carboxyl, carboxylmethyl, guanidinopropyl, and the like, and derivatives and protected derivatives thereof. The above described formula includes all stereoisomeric variations. For example, the amino acid may be selected from asparagine, aspartic acid, cysteine, glutamic acid, lysine, glutamine, arginine, serine, ornitine, threonine, and the like. In one variation, the amino acid may be selected from phenylalanine, tyrosine, and the like, derivatives thereof, and substituted variants thereof.

The terms "arylalkyl" and "heteroarylalkyl" as used herein includes molecular fragments or radicals comprising aryl and heteroaryl, respectively, as defined herein substituted with a linear or branched alkylene group, such as benzyl, phenethyl, α-methylbenzyl, picolinyl, pyrimidinylethyl, and the like.

It is to be understood that the above-described terms can be combined to generate chemically-relevant groups, such as "haloalkoxyalkyl" referring to for example trifluoromethyloxyethyl, 1,2-difluoro-2-chloroeth-1-yloxypropyl, and the like.

The term "amino acid derivative" as used herein refers generally to aminoalkylcarboxylate, where the amino radical or the carboxylate radical are each optionally substituted with alkyl, carboxylalkyl, alkylamino, and the like, or optionally protected; and the intervening divalent alkyl fragment is optionally substituted with alkyl, hydroxy alkyl, sulfhydrylalkyl, aminoalkyl, carboxyalkyl, and the like, including groups corresponding to the side chains found in naturally occurring amino acids, such as are found in serine, cysteine, methionine, aspartic acid, glutamic acid, and the like.

The term "peptide" as used herein includes molecular fragments or radicals comprising a series of amino acids and amino acid analogs and derivatives covalently linked one to the other by amide bonds.

In another embodiment, the bivalent linker comprises a spacer linker and a releasable linker taken together to form 3-thiosuccinimid-1-ylalkyloxymethyloxy, where the methyl is optionally substituted with alkyl or substituted aryl.

In another embodiment, the bivalent linker comprises a spacer linker and a releasable linker taken together to form 3-thiosuccinimid-1-ylalkylcarbonyl, where the carbonyl forms an acylaziridine with the active moiety, or analog or derivative thereof.

In another embodiment, the bivalent linker comprises a spacer linker and a releasable linker taken together to form 1-alkoxycycloalkylenoxy.

In another embodiment, the bivalent linker comprises a spacer linker and a releasable linker taken together to form alkyleneaminocarbonyl (dicarboxylarylene)carboxylate.

In another embodiment, the bivalent linker comprises a releasable linker, a spacer linker, and a releasable linker taken together to form dithioalkylcarbonylhydrazide, where the hydrazide forms a hydrazone with the active moiety, or analog or derivative thereof. In another embodiment, the bivalent linker comprises a spacer linker and a releasable linker taken together to form 3-thiosuccinimid-1-ylalkylcarbonylhydrazide, where the hydrazide forms an hydrazone with the active moiety, or analog or derivative thereof.

In another embodiment, the bivalent linker comprises a spacer linker and a releasable linker taken together to form 3-thioalkylsulfonylalkyl(disubstituted silyl)oxy, where the disubstituted silyl is substituted with alkyl or optionally substituted aryl.

In another embodiment, the bivalent linker comprises a plurality of spacer linkers selected from the group consisting of the naturally occurring amino acids and stereoisomers thereof.

In another embodiment, the bivalent linker comprises a releasable linker, a spacer linker, and a releasable linker taken together to form 3-dithioalkyloxycarbonyl, where the carbonyl forms a carbonate with the active moiety, or analog or derivative thereof.

In another embodiment, the bivalent linker comprises a releasable linker, a spacer linker, and a releasable linker taken together to form 3-dithioarylalkyloxycarbonyl, where the carbonyl forms a carbonate with the active moiety, or analog or derivative thereof, and the aryl is optionally substituted.

In another embodiment, the bivalent linker comprises a spacer linker and a releasable linker taken together to form 3-thiosuccinimid-1-ylalkyloxyalkyloxyalkylidene, where the alkylidene forms an hydrazone with the active moiety, or analog or derivative thereof, each alkyl is independently selected, and the oxyalkyloxy is optionally substituted with alkyl or optionally substituted aryl.

In another embodiment, the bivalent linker comprises a releasable linker, a spacer linker, and a releasable linker taken together to form 3-dithioalkyloxycarbonylhydrazide.

In another embodiment, the bivalent linker comprises a releasable linker, a spacer linker, and a releasable linker taken together to form 3-dithioalkylamino, where the amino forms a vinylogous amide with the active moiety, or analog or derivative thereof.

In another embodiment, the bivalent linker comprises a releasable linker, a spacer linker, and a releasable linker taken together to form 3-dithioalkylamino, where the amino forms a vinylogous amide with the active moiety, or analog or derivative thereof, and the alkyl is ethyl.

In another embodiment, the bivalent linker comprises a releasable linker, a spacer linker, and a releasable linker taken together to form 3-dithioalkylaminocarbonyl, where the carbonyl forms a carbamate with the active moiety, or analog or derivative thereof.

In another embodiment, the bivalent linker comprises a releasable linker, a spacer linker, and a releasable linker taken together to form 3-dithioalkylaminocarbonyl, where the carbonyl forms a carbamate with the active moiety, or analog or derivative thereof, and the alkyl is ethyl.

In another embodiment, the polyvalent linker includes additional spacer linkers and releasable linkers connected to form a polyvalent 3-thiosuccinimid-1-ylalkyloxymethyloxy group, illustrated by the following formula

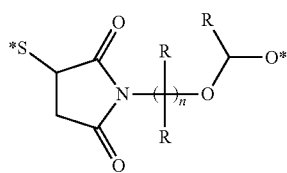

where n is an integer from 1 to 6, the alkyl group is optionally substituted, and the methyl is optionally substituted with an additional alkyl or optionally substituted aryl group, each of which is represented by an independently selected group R. The (*) symbols indicate points of attachment of the polyvalent linker fragment to other parts of the conjugates described herein.

In another embodiment, the polyvalent linker includes additional spacer linkers and releasable linkers connected to form a polyvalent 3-thiosuccinimid-1-ylalkylcarbonyl group, illustrated by the following formula

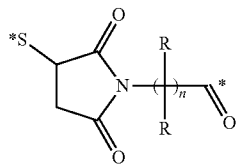

where n is an integer from 1 to 6, and the alkyl group is optionally substituted. The (*) symbols indicate points of attachment of the polyvalent linker fragment to other parts of the conjugates described herein. In another embodiment, the polyvalent linker includes spacer linkers and releasable linkers connected to form a polyvalent 3-thioalkylsulfonyl-alkyl(disubstituted silyl)oxy group, where the disubstituted silyl is substituted with alkyl and/or optionally substituted aryl groups.

In another embodiment, the polyvalent linker includes spacer linkers and releasable linkers connected to form a polyvalent dithioalkylcarbonylhydrazide group, or a polyvalent 3-thiosuccinimid-1-ylalkylcarbonylhydrazide, illustrated by the following formulae

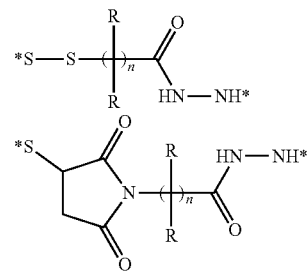

where n is an integer from 1 to 6, the alkyl group is optionally substituted, and the hydrazide forms an hydrazone with (B), (D), or another part of the polyvalent linker (L). The (*) symbols indicate points of attachment of the polyvalent linker fragment to other parts of the conjugates described herein.

In another embodiment, the polyvalent linker includes spacer linkers and releasable linkers connected to form a polyvalent 3-thiosuccinimid-1-ylalkyloxyalkyloxyalkylidene group, illustrated by the following formula

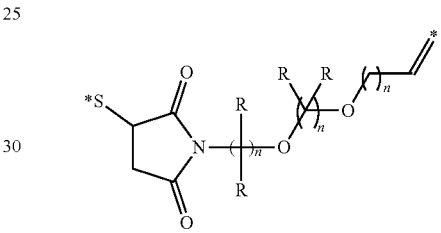

where each n is an independently selected integer from 1 to 6, each alkyl group independently selected and is optionally substituted, such as with alkyl or optionally substituted aryl, and where the alkylidene forms an hydrazone with the targeting ligand, the active moiety, or another part of the polyvalent linker. The (*) symbols indicate points of attachment of the polyvalent linker fragment to other parts of the conjugates described herein.

Additional illustrative linkers are described in WO 2006/012527, the disclosure of which is incorporated herein by reference. Additional linkers are described in the following Table 1, where the (*) atom is the point of attachment of additional spacer or releasable linkers, the active moiety, and/or the targeting ligand.

TABLE 1

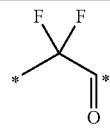

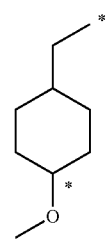

TABLE 1-continued

TABLE 1-continued

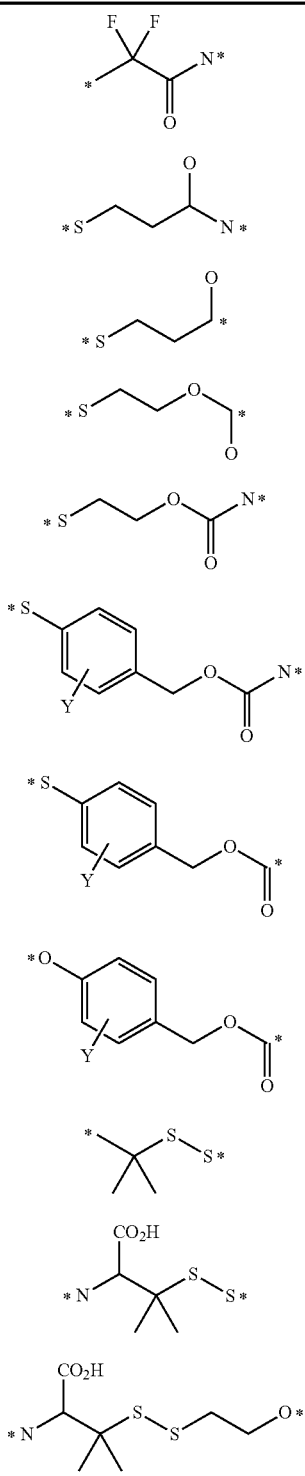

As suggested above, the conjugates of the invention may have 1, 2, 3, 4 or 5 active moieties linked to a single targeting ligand. In particular aspects of the invention, only one active moiety will be linked to a single targeting ligand. However, when there are two or more active moieties linked to a single targeting ligand, the active moieties may be the same or different. For example, where there are two active moieties linked to a single targeting ligand, the active moieties may be two different therapeutic agents, two different imaging agents, or a therapeutic agent and an imaging agent.

It is to be understood that analogs and derivatives of each of the foregoing B, L, and D are also contemplated and described herein, and that when used herein, the terms targeting moiety (or B), linker (or L), and active moiety (or D) collectively refer to such analogs and derivatives.

III. Methods of Detection, Diagnosis and Imaging

The present invention also includes methods of using the conjugates in a variety of applications, such as in methods of detecting, diagnosing and imaging cancer. For example, in one aspect the invention is directed to methods for detecting a tumor in a subject, comprising administering a conjugate as defined herein to a subject suspected of having a tumor and detecting the conjugate in the subject, wherein the active moiety D of the conjugate is an imaging agent. In a related aspect, the invention includes methods for diagnosing cancer in a subject, comprising administering a conjugate as defined herein to a subject suspected of having cancer and detecting the conjugate in the subject, wherein the active moiety D of the conjugate is an imaging agent. In a further related aspect, the invention includes methods for imaging cancer in a subject, comprising administering a conjugate as defined herein to a subject suspected of or having cancer and detecting the conjugate in the subject, wherein the active moiety D of the conjugate is an imaging agent.

IV. Methods of Treatment

In another aspect, the invention is directed to methods for treating a subject having cancer, comprising administering a therapeutically-effective amount of a conjugate as defined herein to a subject having cancer, wherein the active moiety D of the conjugate is a therapeutic agent. Upon binding of the receptors, the therapeutic agent can exert an effect, either directly on the cell to which it is bound or to neighboring cells, due to the properties of the therapeutic agent.

V. Pharmaceutical Formulations

The methods of the present invention using the conjugates may be practiced in one or more of in vitro, in vivo and ex vivo applications. When used in vivo and ex vivo, the conjugates may be prepared as a pharmaceutical composition comprising the conjugate and one or more pharmaceutically-acceptable carriers and/or diluents. The skilled artisan will understand that the specific elements comprising a pharmaceutical composition will depend on factors that include the identity of the targeting ligand and the active moiety in the conjugate, the identity of the cancer or tumor to be detected or treated, the location in the subject of the cancer or tumor, available means for detecting the imaging agent, and the means used to administer the conjugate to the subject.

The pharmaceutical compositions of the present invention may be formulated, for example, for oral, sublingual, intranasal, intraocular, rectal, transdermal, mucosal, pulmonary, topical or parenteral administration. Parenteral modes of administration include without limitation, intradermal, subcutaneous (s.c., s.q., sub-Q, Hypo), intramuscular (i.m.), intravenous (i.v.), intraperitoneal (i.p.), intra-arterial, intramedulary, intracardiac, intra-articular (joint), intrasynovial (joint fluid area), intracranial, intraspinal, and intrathecal (spinal fluids). Any known device useful for parenteral injection or infusion of pharmaceutical compositions can be used to effect such administration.

Examples of parenteral dosage forms include aqueous solutions of the conjugates, in an isotonic saline, 5% glucose or other well-known pharmaceutically-acceptable liquid carriers such as liquid alcohols, glycols, esters, and amides. The parenteral dosage form in accordance with this invention can be in the form of a reconstitutable lyophilizate comprising the dose of the conjugate. In one aspect of the present embodiment, the conjugates may be formulated into prolonged or extended release formulations such as, for example, the biodegradable carbohydrate matrices described in U.S. Pat. Nos. 4,713,249, 5,266,333, and 5,417,982, the disclosures of each of which are incorporated herein by reference in their entireties, or alternatively, a slow pump (e.g., an osmotic pump) can be used.

In one aspect on the invention, at least one additional therapeutic factor can be administered to a subject in combination with or as an adjuvant to the conjugates and methods of the present invention to enhance the conjugate-mediated elimination of the population of pathogenic cells, or more than one therapeutic factor can be used. In one example, the therapeutic factor can be selected from a chemotherapeutic agent, or another therapeutic factor capable of complementing the efficacy of the administered conjugate of the present invention. In another example, chemotherapeutic agents which are, for example, cytotoxic themselves, can work to enhance tumor permeability, are also suitable for use as an additional therapeutic factor.

The therapeutic factor can be administered to the subject prior to, after, or at the same time as the conjugate, and the therapeutic factor can be administered as part of the same composition containing the conjugate or as part of a different composition than the conjugate. Any such therapeutic composition containing the therapeutic factor at a therapeutically effective dose can be used in the present invention.

VI. Administration to Subjects

A. Methods of Detection, Diagnosis and Imaging

The amount of conjugate used in the methods of detection, diagnosis and imaging described herein will also depend on a variety of factors, including the identity of the targeting ligand, the identity of the imaging agent, the identity of the cancer or tumor to be detected, the location in the subject of the cancer or tumor, available means for detecting the imaging agent, the means used to administer the conjugate to the subject, and the weight of the subject. Generally, the conjugates will be administered to a subject in a method of detection, diagnosis or imaging in an amount of between about 0.1 mg to about 50 mg. Particular examples include about 0.5 mg to about 10 mg, and from about 1 mg to about 5 mg. In non-limiting examples, about 1 mg, 2 mg, 3 mg, 4 mg, 5 mg, 6 mg, 7 mg, 8 mg, 9 mg or 10 mg of a conjugate of the invention may be a suitable amount of conjugate to be administered to a subject for use in the methods of detection, diagnosis and imaging described herein.

The skilled artisan will understand that each of the methods of detection, diagnosis and imaging can be practiced using one type of conjugate, or more than one type of conjugate, such as two, three, four or more. When two or more types of conjugates are used, the methods can be practiced by administering two or more types of conjugate to the subject concurrently or sequentially, separated in time by 5, 10, 15, 20, 25, 30 or more minutes, depending on the method being practiced. Illustratively, for example, the subject can be administered conjugates with different targeting ligands, but the same active moiety in a co-dosing protocol. In other embodiments, the subject can be administered conjugates comprising the same targeting ligand linked to different active moieties, or different targeting ligand linked to different active moieties.

When used in methods of detection, diagnosis and imaging, the conjugates are preferably administered to a subject parenterally, e.g., intradermally, subcutaneously, intramuscularly, intraperitoneally, intravenously, or intrathecally. However, the skilled artisan will understand that in some instances, administration may be oral, sublingual, intranasal, intraocular, rectal, transdermal, mucosal, pulmonary, or topical.

In addition to detecting the conjugates, the skilled artisan will understand that the amount of signal detected can be compared to other values, such as control values from a subject known to not have a tumor or cancer, or values obtained on an earlier date from the same subject. Thus, each of the methods of the present invention may alternatively comprise measuring the amount of conjugate in the subject, rather than simply detecting it, and optionally further comparing the measured amount to a control value or a value obtained at an earlier time in the same subject.

The means used to detect the conjugates vary based on factors including the identity of the imaging agent, whether the method is being practiced in vitro, in vivo or ex vivo, and when practiced in vivo, the location in the subject to be visualized. Suitable means for detecting a conjugate comprising a radio-imaging agent include, but are not limited to radioimaging systems, MRI, SPECT-CT, and PET imaging. Suitable means for detecting a conjugate comprising an optical imaging agent include, but are not limited to flow cytometry, confocal microscopy, fluorescence activated cell sorters, and fluorescence imaging systems such as Lumina II.

B. Methods of Treatment

The amount of conjugate used in the methods of treatment described herein will also depend on a variety of factors, including the identity of the targeting ligand, the identity of the therapeutic agent, the identity of the cancer or tumor to be detected, the location in the subject of the cancer or tumor, the means used to administer the conjugate to the subject, and the health, age and weight of the subject being treated. Generally, the conjugates will be administered to a subject in a method of treatment in an amount of between about 0.1 mg to about 50 mg. Particular examples include about 0.5 mg to about 10 mg, and from about 1 mg to about 5 mg. In non-limiting examples, about 1 mg, 2 mg, 3 mg, 4 mg, 5 mg, 6 mg, 7 mg, 8 mg, 9 mg or 10 mg of a conjugate of the invention may be a suitable amount for administered to a subject for use in the methods of treatment described herein.

The skilled artisan will understand that the methods of treatment can be practiced using one type of conjugate, or more than one type of conjugate, such as two, three, four or more. When two or more types of conjugates are used, the methods can be practiced by administering two or more types conjugate to the subject concurrently or sequentially, separated in time by 5, 10, 15, 20, 25, 30 or more minutes, depending on the method being practiced. Illustratively, for example, the subject can be administered conjugates with different targeting ligands, but the same active moiety in a co-dosing protocol. In other embodiments, the subject can be administered conjugates comprising the same targeting ligand linked to different active moieties, or different targeting ligand linked to different active moieties.

Any effective regimen for administering the conjugates can be employed. Administration frequencies for a pharmaceutical composition comprising one or more of the conjugates of the present invention include 4, 3, 2 or once daily, every other day, every third day, every fourth day, every fifth day, every sixth day, once weekly, every eight days, every nine days, every ten days, bi-weekly, monthly and bi-monthly. The duration of treatment will be based on the disease being treated and will be best determined by the attending physician. However, continuation of treatment is contemplated to last for a number of days, weeks, months or years. Depending on the means of administration, a dosage may be administered all at once, such as with an oral formulation in a capsule or liquid, or slowly over a period of time, such as with an intramuscular or intravenous administration.

Illustratively, the conjugates can be administered as single doses, or can be divided and administered as a multiple-dose daily regimen. In other embodiments, a staggered regimen, for example, one to three days per week can be used as an alternative to daily treatment, and for the purpose of defining this invention such intermittent or staggered daily regimen is considered to be equivalent to every day treatment and within the scope of this invention. According to at least one embodiment, the subject is treated with multiple injections of the conjugate to eliminate a population of pathogenic cells. In another embodiment, the subject is injected multiple times (preferably about 2 up to about 50 times) with the conjugate, for example, at 12-72 hour intervals or at 48-72 hour intervals. In other embodiments, additional injections of the conjugate can be administered to the subject at an interval of days or months after the initial injections(s) and the additional injections prevent recurrence of the disease state caused by the pathogenic cells.

When used in methods of treatment, the conjugates are preferably administered to a subject parenterally, e.g., intradermally, subcutaneously, intramuscularly, intraperitoneally, intravenously, or intrathecally. However, the skilled artisan will understand that in some instances, administration may be oral, sublingual, intranasal, intraocular, rectal, transdermal, mucosal, pulmonary, or topical.

In relevant embodiments of the invention, the tumors and cancers that can be detected, diagnosed, imaged, and/or treated are any having cells that express CCK2R or CCK2i4svR, or both. In some instances, the tumors and cancers will have cells that overexpress CCK2R or CCK2i4svR, or both. The tumors and cancers include, but are not limited to, medullary thyroid cancers, insulinomas, small cell lung cancers, non small cell lung cancers, astrocytoma, gastric cancer, bronchial and ileal carcinoids, GIST tumors, and colon cancers, prostate cancer, hepatocellular carcinomas, and pancreatic cancers.

In each of the embodiments and aspects of the invention, the subject is a human, a non-human primate, bird, horse, cow, goat, sheep, a companion animal, such as a dog, cat or rodent, or other mammal.

VII. Methods of Making the Conjugates

Generally, any manner of forming a conjugate between the linker and the targeting ligand, and between the linker and the active moiety, can be utilized in accordance with the present invention. Also, any art-recognized method of forming a conjugate between a spacer, a cleavable linker, and one or more heteroatoms to form the linker L can be used. The conjugate can be formed by direct conjugation of any of these molecules, for example, through hydrogen, ionic, or covalent bonds. Covalent bonding can occur, for example, through the formation of amide, ester, disulfide, or imino bonds between acid, aldehyde, hydroxy, amino, sulfhydryl, or hydrazo groups.

Methods of synthesis are chosen depending upon the selection of the optionally included heteroatoms or the heteroatoms that are already present on the spacers, cleavable linkers, targeting ligands, and active moieties. In general, useful bond forming reactions are described in Richard C. Larock, "Comprehensive Organic Transformations, a guide to functional group preparations," VCH Publishers, Inc. New York (1989), and in Theodora E. Greene & Peter G. M. Wuts, "Protective Groups ion Organic Synthesis," 2d edition, John Wiley & Sons, Inc. New York (1991), the disclosures of which are incorporated herein by reference in their entireties.

More specifically, disulfide groups can be generally formed by reacting an alkyl or aryl sulfonylthioalkyl derivative, or the corresponding heteroaryldithioalkyl derivative such as a pyridin-2-yldithioalkyl derivative, and the like, with an alkylenethiol derivative. For example, the required alkyl or aryl sulfonylthioalkyl derivative may be prepared according to the method of Ranasinghe and Fuchs, Synth. Commun. 18(3), 227-32 (1988), the disclosure of which is incorporated herein by reference in its entirety. Other methods of preparing unsymmetrical dialkyl disulfides are based on a transthiolation of unsymmetrical heteroaryl-alkyl disulfides, such as 2-thiopyridinyl, 3-nitro-2-thiopyridinyl, and like disulfides, with alkyl thiol, as described in WO 88/01622, European Patent Application No. 0116208A1, and U.S. Pat. No. 4,691,024, the disclosures of which are incorporated herein by reference in their entireties. Further, carbonates, thiocarbonates, and carbamates can generally be formed by reacting an hydroxy-substituted compound, a thio-substituted compound, or an amine-substituted compound, respectively, with an activated alkoxycarbonyl derivative having a suitable leaving group.

VIII. Examples

The conjugates described herein may be prepared by conventional organic synthesis methodology, or as otherwise indicated herein. Unless noted otherwise, all starting materials and reagents are generally available through commercial suppliers.

A. Synthesis and Purification of Targeting Ligand Z-360$^{32-35}$

Synthesis of targeting ligand Z-360 was accomplished according to the following steps.

Step 1—

Boc D Diaminopropionic acid (3 g) was dissolved in 100 ml of ethanol. Potassium carbonate (1.095 g) and 2-fluoronitrobenzene (1.71 ml) was added followed by refluxing for 4 hours. The reaction mixture was concentrated under pressure, water was added and the resulting mixture was washed with diethyl ether. 1 N HCl was the added to the aqueous layer to adjust its pH to 3 followed by extraction with ethyl acetate. The organic layer was then dried over sodium sulfate and then the solvent was evaporated under reduced pressure, where 4.5 g (95%) of the following compound was obtained as a bright orange solid.

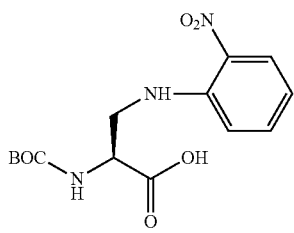 [SMILES: CC(C)(C)OC(=O)N[C@@H](CNc1ccccc1[N+](=O)[O-])C(=O)O]

Step 2—

The above product was used without further purification. It was dissolved in 50 ml methanol followed by addition of 10% palladium carbon (50 mg). The resulting solution was purged with nitrogen gas and then stirred at room temperature under hydrogen gas for 3 hrs. The reaction mixture was then filtered under celite, and the fitrate was concentrated under pressure whereby 2-tert-butoxycarbonyl amino 3(2-aminophenyl)-amino propionic acid was obtained as a dark brown compound. This compound was resuspended in toluene (120 ml) and the resulting suspension refluxed in toluene for 3 hrs overnight while removing water with a dean stark extractor. The solution was then concentrated under reduced pressure and purified by column chromatography (ethyl acetate hexane) to obtain 1.722 g of the following compound as a mustard yellow solid. (Yield approximately 44%).

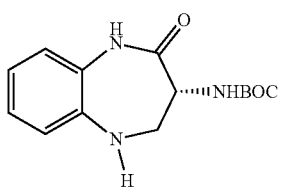

Step 3—

To a solution of 1.722 g of the cyclized product (R)-(+)-2-oxo-3-tert-butoxycarbonylamino-1,3,4,5-tetrahydro-2H-1,5-benzodiazepine, in 13.7 ml of acetic acid were added 2.315 ml of cyclohexanone and 49 mg of platinum oxide. The resulting mixture was stirred at room temperature for 6 hrs under hydrogen atmosphere. To the reaction mixture was added 7 ml of ethyl acetate and 25 mg of activated charcoal followed by stirring for an additional one hour at room temperature. The reaction mixture was the filtered, a 2 N aqueous solution of NaOH was added to the filtrate to neutralize the same under stirring after which it was separated into layers. The organic layer was successively washed with a saturated solution of sodium bicarbonate and brine dried over anhydrous sodium sulfate and then purified by column chromatography (ethyl acetate/hexane) to obtain 1.0109 g of the following product (R)-(−)-2-oxo-3-tert-butoxycarbonylamino-5-cyclohexyl-1,3,4,5-tetrahydro-2H-1,5-benzodiazepine as a pale yellow solid. (Yield approximately 45%).

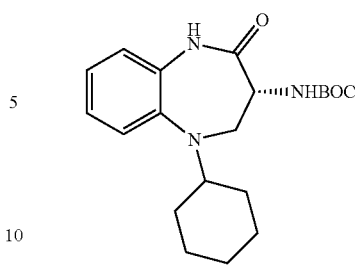

Step 4—

To a solution of (R)-(−)-2-oxo-3-tert-butoxycarbonylamino-5-cyclohexyl-1,3,4,5-tetrahydro-2H-1,5-benzodiazepine (1.7131 g) in 6.8 ml anhydrous DMSO was added to 1.066 ml 1-chloropinacolone and 0.9849 g of potassium carbonate, 0.039 potassium iodide and 0.0459 g of tetrabutyl ammonium bromide. The solution was stirred at 60° c. for 4 hrs. The reaction was quenched with water and then the organic layer was washed with a saturated solution of sodium bicarbonate and brine, dried over anhydrous sodium sulfate and then purified by column chromatography where 1.355 g of the following product (R)-1-tert-butylcarbonyl-methyl-2-oxo-3-tert-butoxycarbonylamino-5-cyclohexyl-1,3,4,5-tetrahydro-2H-1,5-benzodiazepine were obtained as a yellow-brown solid. (Yield approximately 62%).

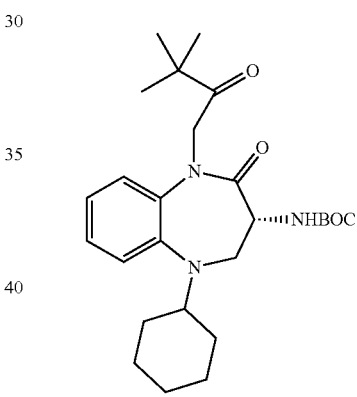

Step 5—

To 1.355 g of the Boc-protected (R)-1-tert-butylcarbonyl-methyl-2-oxo-3-tert-butoxycarbonylamino-5-cyclohexyl-1,3,4,5-tetrahydro-2H-1,5-benzodiazepine was added 2.2 ml 6 N concentrated hydrochloric acid and 2.2 ml ethanol. The mixture was stirred at 60 degrees for 2 hours. After the reaction mixture was cooled to room temperature, a mixed solvent of water and diethyl ether (1:1) was added. The aqueous layer was separately neutralized with 6 N aqueous NaOH and then extracted with ethyl acetate. The extract was washed with brine, dried over anhydrous sodium sulfate and then evaporated under reduced pressure to yield 0.559 g. This product was further dissolved in 6.64 ml ethyl acetate and then to the resulting solution was added 0.197 oxalic acid dihydrate and then 4.4 ml hexane and the mixture was stirred overnight and allowed to crystallize yielding 0.6790 g of (R)-(−)-1-tert-butylcarbonylmethyl-2-oxo-3-amino-5-cyclohexyl-1,3,4,5-tetrahydro-2H-1,5-benzodiazepine oxalate monohydrate and (R)-(−)-1-tert-butylcarbonylm-ethyl-2-oxo-3-amino-5-cyclohexyl-1,3,4,5-tetrahydro-2H-1,5-benzodiazepine oxalate. (Yield approximately 51%).

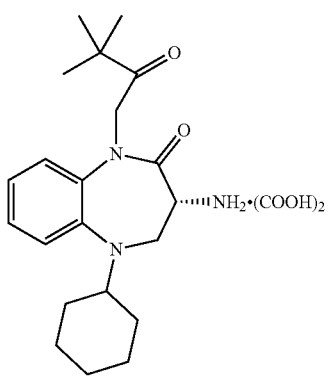

Step 6—

2.619 g of 3-amino benzoic acid was dissolved in 38.2 ml of 0.5 N NaOH followed by dropwise addition of a solution of 2.411 ml phenyl chloroformate in 6.712 ml of THF. The reaction mixture was stirred for one hour. The precipitate that formed was then filtered with suction, washed with water, dried and then recrystallized from ethanol to obtain a white powder of 3-phenyloxycarbonylaminobenzoic acid. (Yield approximately 85%).

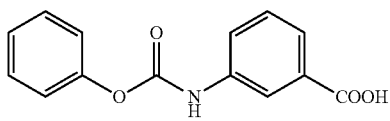 [SMILES: O=C(Nc1cccc(C(=O)O)c1)Oc1ccccc1]

Step 7—

Target Ligand Z-360((R)-(−)-3-[3-(1-tert-butyl carbonyl-methyl-2-oxo-5-cyclohexyl-1,3,4,5-tetrahydro-2H-1,5-benzodiazepin-3-yl)ureido]benzoic acid monohydrate). To a solution of 0.6790 g of the oxalate monohydrate derivative above 7.290 ml anhydrous DMSO, 0.3819 g phenoloxy-(N-phenoxy carbonyl amino benzoic acid, 0.5915 ml triethylamine and catalytic amount of DMAP (5%). The resulting mixture was stirred at 60 degrees for 2 hours and then 7.290 ml of ethanol were added to the reaction mixture and the mixture was stirred at room temperature for an additional two hours. Under ice cooling, 7.290 ml of 1 N HCl was then added dropwise to precipitate the following end product.

Z-360

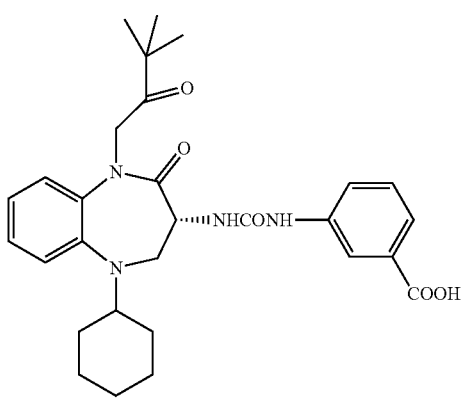

Stated another way, Z-360 ((R)-(−)-3-[3-(1-tert-butylcarbonylmethyl-2-oxo-5-cyclohexyl-1,3,4,5-tetrahydro-2H-1, 5-benzodiazepin-3-yl)ureido]benzoic acid monohydrate) was synthesized as noted below in Scheme 1, wherein a) is potassium carbonate/ethanol, reflux 3 hrs; b) is $H_2$, 10% Pd—C/methanol 3 hrs; c) is toluene, reflux; d) is cyclohexanone, platinum oxide/acetic acid 6 h; e) is chloropinacolone, tetrabutyl ammonium bromide, potassium carbonate, potassium iodide, DMSO 4 h at 60 degrees; f) is 6 N HCl, Ethanol, 60 degrees, 2 h; g) is oxalic acid monohydrate/ethyl acetate, hexane; h) is phenoloxy(N-phenoxycarbonyl amino benzoic acid, triethyl amine DMAP DMSO; and i) is ethanol 2 h, 1 N HCl.

Scheme 1: Synthesis of Z-360

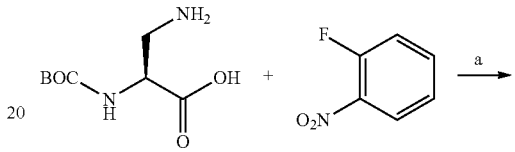

1

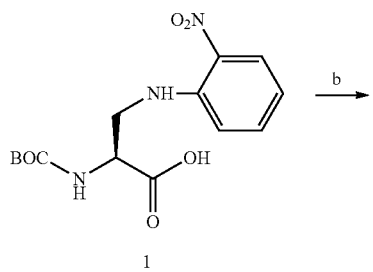

2

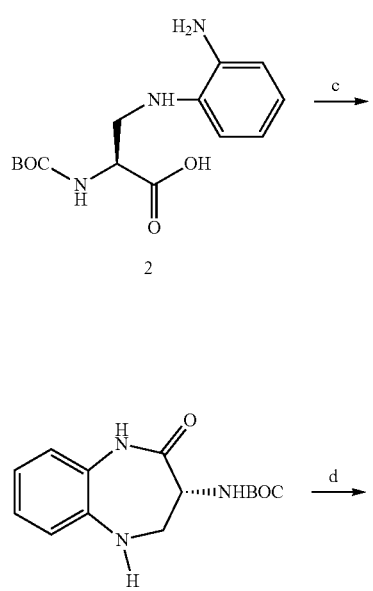

3

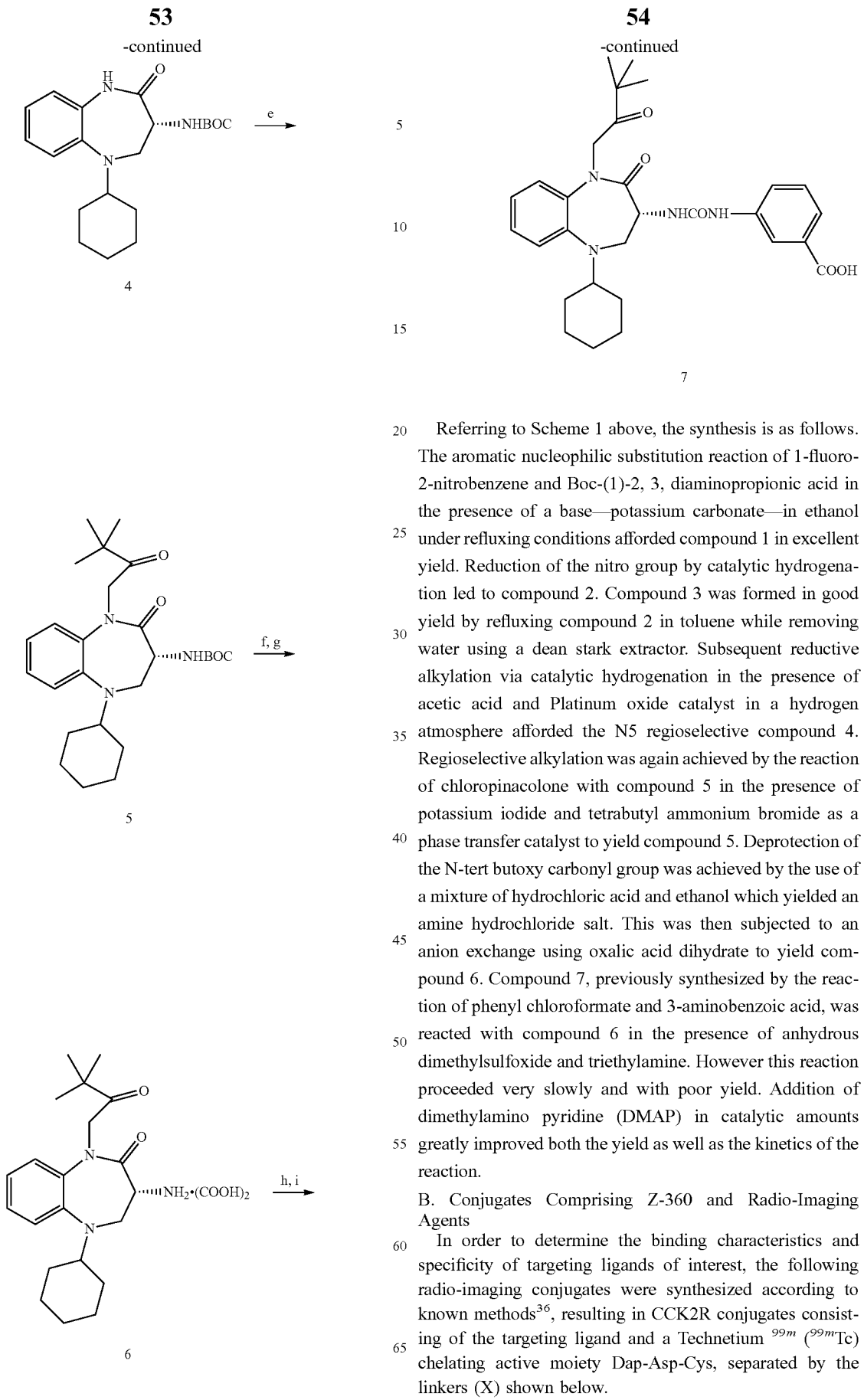

Referring to Scheme 1 above, the synthesis is as follows. The aromatic nucleophilic substitution reaction of 1-fluoro-2-nitrobenzene and Boc-(1)-2, 3, diaminopropionic acid in the presence of a base—potassium carbonate—in ethanol under refluxing conditions afforded compound 1 in excellent yield. Reduction of the nitro group by catalytic hydrogenation led to compound 2. Compound 3 was formed in good yield by refluxing compound 2 in toluene while removing water using a dean stark extractor. Subsequent reductive alkylation via catalytic hydrogenation in the presence of acetic acid and Platinum oxide catalyst in a hydrogen atmosphere afforded the N5 regioselective compound 4. Regioselective alkylation was again achieved by the reaction of chloropinacolone with compound 5 in the presence of potassium iodide and tetrabutyl ammonium bromide as a phase transfer catalyst to yield compound 5. Deprotection of the N-tert butoxy carbonyl group was achieved by the use of a mixture of hydrochloric acid and ethanol which yielded an amine hydrochloride salt. This was then subjected to an anion exchange using oxalic acid dihydrate to yield compound 6. Compound 7, previously synthesized by the reaction of phenyl chloroformate and 3-aminobenzoic acid, was reacted with compound 6 in the presence of anhydrous dimethylsulfoxide and triethylamine. However this reaction proceeded very slowly and with poor yield. Addition of dimethylamino pyridine (DMAP) in catalytic amounts greatly improved both the yield as well as the kinetics of the reaction.

B. Conjugates Comprising Z-360 and Radio-Imaging Agents

In order to determine the binding characteristics and specificity of targeting ligands of interest, the following radio-imaging conjugates were synthesized according to known methods[36], resulting in CCK2R conjugates consisting of the targeting ligand and a Technetium $^{99m}$ ($^{99m}Tc$) chelating active moiety Dap-Asp-Cys, separated by the linkers (X) shown below.

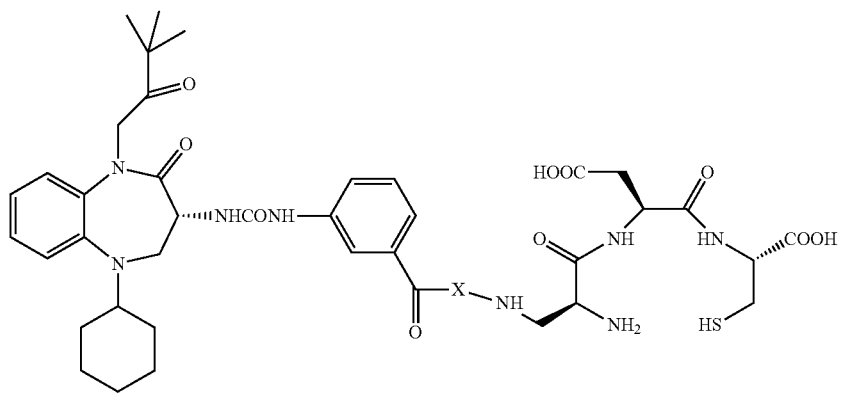

CRL-1, where X=HN-Glu-Arg-Asp-CO
CRL-2, where X=HN-Glu-PS-Glu-PS-CO
CRL-3, where X=HN-Octanoyl-Glu-PS-Glu-PS-CO
CRL-4, where X=absent As can be seen, CRL-1 contains a simple tripeptide spacer. Because scavenger receptors in the kidneys and liver can bind diverse peptidic conjugates, the peptidic spacer in CRL-1 was replaced with a less readily scavenged peptidosaccharide (PS) spacer in CRL-2[37]. Next, to assure sufficient separation between the targeting ligand and its tethered radiochelate, CRL-3 was designed with the same spacer as CRL-2, with an octanoyl moiety inserted before the peptidosaccharide spacer. Finally, to assist with evaluation of the impact of linker length, CRL-4 was prepared with no linker. The detailed structure of each conjugates is shown as follows.

CRL-1

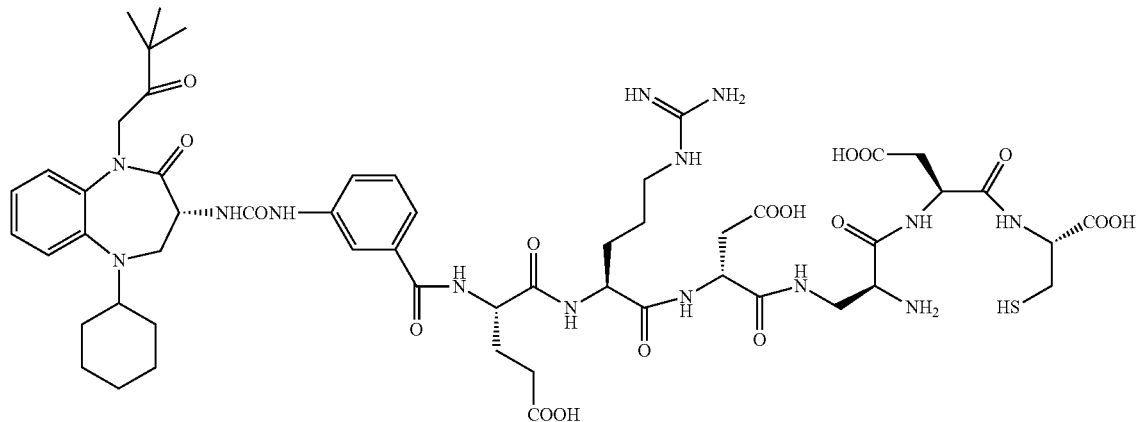

CRL-2

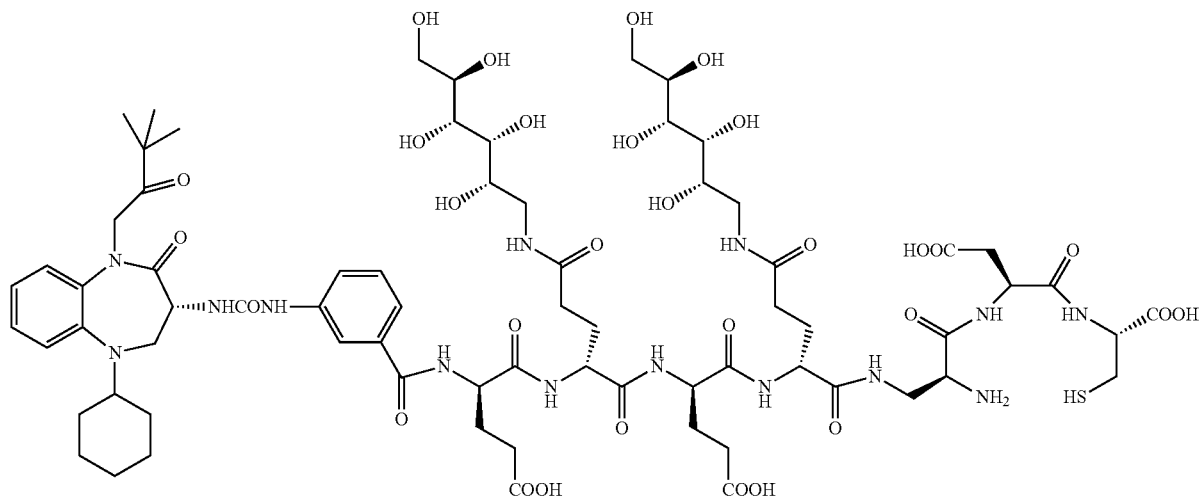

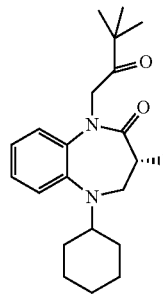
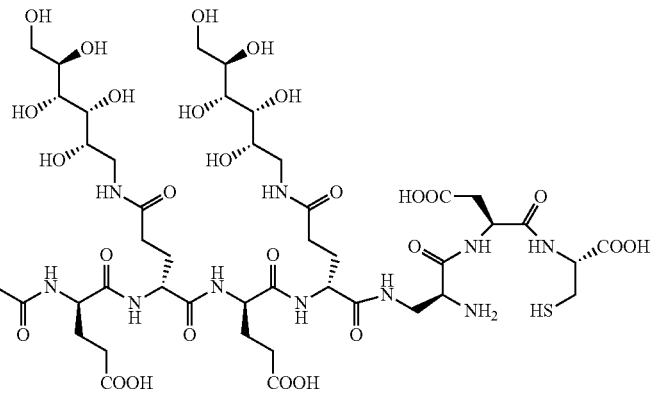

CRL-3

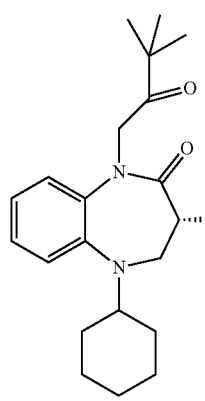
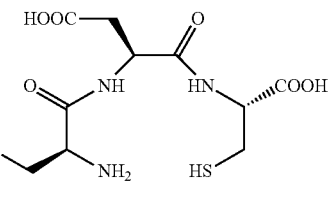

CRL-4

The synthesis of the FMOC protected version of PS is provided as follows. The sugar/peptidosaccharo monomer (PS) noted in the linkers of CRL-2 and CRL-3 was synthesized according to Scheme 2 (below) using previously described literature methods[37-38]. The monomer was used in the synthesis of the linkers described for CRL-2 and CRL-3 above. In short, the free OH groups in D-glucamine were first protected using dimethoxypropane in the presence of catalytic amounts of p-toluenesulfonic acid. The amine group was then reacted with Fmoc-glutamic-Oallyl to form an amide bond. The side chain carboxylic acid was deprotected using palladium tetrakis triphenylphosphine in the presence of N-methyl morpholine acetic acid and chloroform. This compound was used in solid phase synthesis in the same way amino acid monomers were used. As shown in Scheme 2, to arrive at compound 16 (PS), the following reagents were used: a) p-TsOH, dimethoxypropane; b) acetone, dimethoxypropane, p-TsOH; c) Fmoc-glutamic-Oallyl, PYBOP, DIPEA/DMF; and d) Pd(PPh$_3$)$_4$, NMM/AcOH/CHCl$_3$.

Scheme 2: Synthesis of Sugar/Peptidosaccharo monomer (PS)

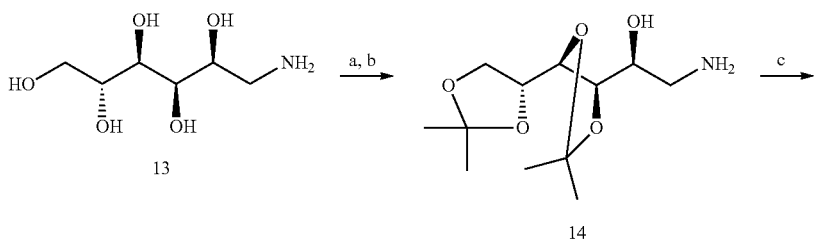

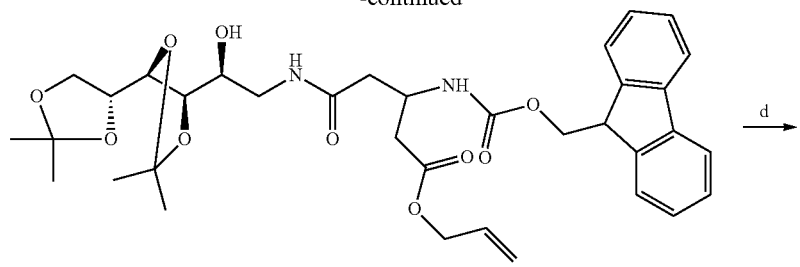
15
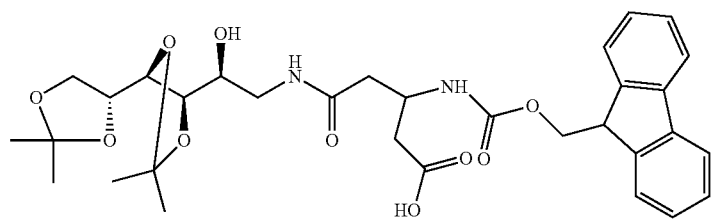
16 (PS)
Synthesis of CRL-3 $^{99m}$Tc
CRL-3 $^{99m}$Tc was produced by linking the targeting ligand Z-360 to a $^{99m}$Technetium chelating agent comprised of the peptide sequence: β-L-diaminopropionic acid (β-DAP), L-aspartic acid (L-Asp), L-cysteine (L-Cys) via linker shown in Scheme 3.
Scheme 3: Synthesis and Formulation of CRL-3 $^{99m}$Tc
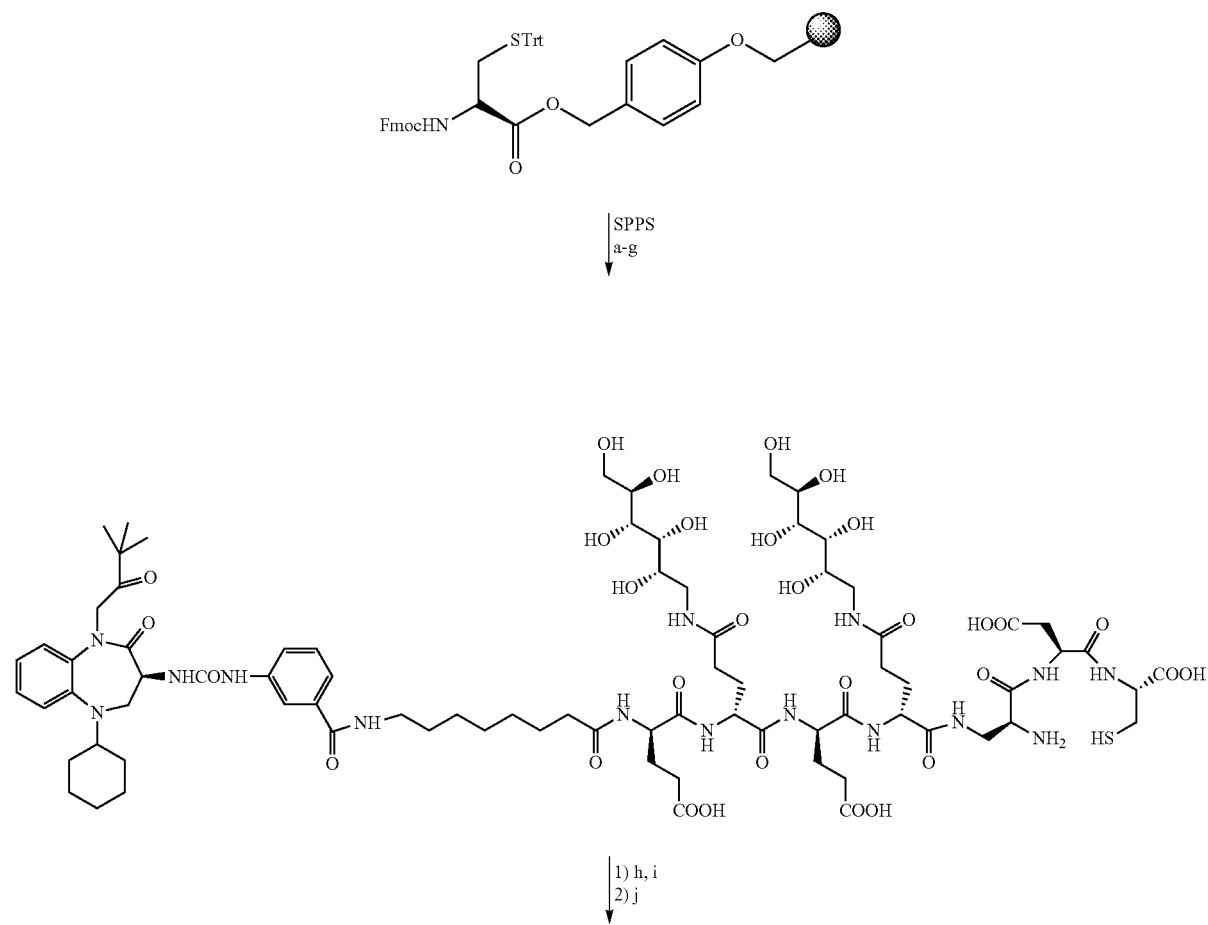

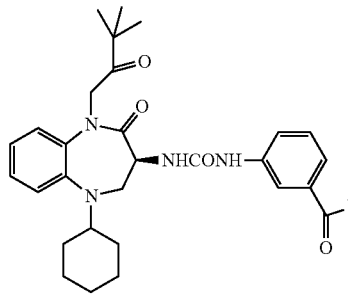
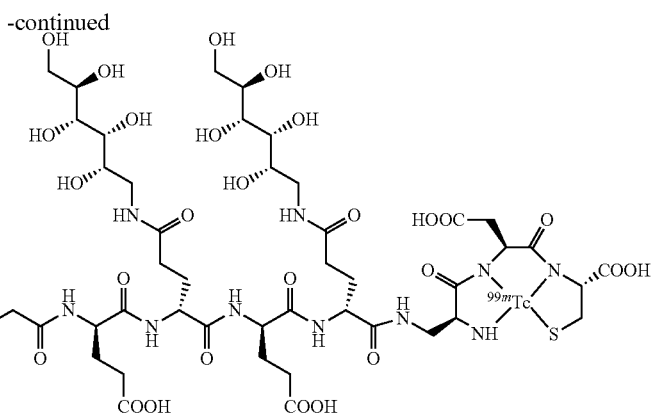

In particular, the [99m]TC chelating moiety (symbolized as EC20)(-DAP-Asp-Cys) was first prepared according to a reported procedure[36]. Briefly, acid-sensitive Wang resin loaded with 0.106 mmol of H-carbonyl-trityl-L-cysteine (H-L-Cys (Trt)-OH) was reacted first with Fmoc-Asp (Otbu)-OH (0.265 mmol), HATU (0.265 mmol) and diisopropylethylamine (1.06 mmol) followed by addition of β-L-diaminopropionic acid (0.265 mmol), HATU (0.265 mmol) and diisopropylethylamine (1.06 mmol) to yield the $^{99m}$Tc chelating moiety. The chelator was then conjugated to Z-360 via a variety of spacers that were selected for both their abilities to render the final conjugate water soluble and to reduce nonspecific binding to receptor negative cells. The monomeric components of these spacers were derived from protected amino acids and a peptidosaccharide (PS) construct described by others. All conjugation reactions were performed under argon atmosphere.acid-sensitive Wang resin loaded with 0.106 mmol of fluorenylmethoxy carbonyl-trityl-L-cysteine (Fmoc-L-Cys(Trt)-OH) was reacted first with HATU (0.265 mmol), followed by sequential addition of the desired protected monomer (0.265 mmol). Fmoc protecting groups were removed after each coupling step using standard conditions (20% piperidine in dimethyl formamide). Removal of the partially deprotected conjugate from the polymeric support was finally accomplished by treatment with a cocktail solution comprising of 92.5% trifluoroacetic acid (TFA), 2.5% 1,2-ethanedithiol, 2.5% triisopropylsilane, and 2.5% deionized water. This reaction also resulted in simultaneous removal of all t-butyl (t-Bu), t-butoxycarbonyl (t-Boc) and trityl protecting groups.

The crude product was purified by preparative reverse-phase high-performance liquid chromatography (RP-HPLC) using a Waters xTerra C18 10 μm; 19×250 mm column with a gradient mobile phase of A=20 mM ammonium acetate buffer and B=acetonitrile; solvent gradient 5% B to 80% B in 30 minutes. Elution of the conjugate was monitored at X.=280 nm and the identities of the eluted compounds were analyzed by LC-MS and MALDI. Formulation and radiolabeling of the conjugates with $^{99m}$Tc was performed according to previously described methods.

Formulation of the purified conjugate was accomplished in the following manner[36]. A solution of stannous chloride dihydrate (0.8 mg, 0.003 mmol) in 0.02 M HCl (0.8 mL) was added to a solution of sodium R-D-glucoheptonate dihydrate (800 mg, 2.815 mmol) in argon purged water (5.0 mL). Requisite peptide (0.001 mmol) was then added to the reaction mixture while purging with argon. After adjusting the pH of the solution to 6.8±0.2 using 0.1 N NaOH, argon purged water was added to achieve a total volume 10.0 mL. The solution mixture was dispensed into 5 mL vials (1.0 mL/vial) under argon atmosphere and lyophilized for 36 h. The vials were sealed under argon atmosphere to yield the nonradioactive formulation kits, which were stored at −20° C. until use. A solution of sodium pertechnetate [99m]Tc (1.0 mL, 15 mCi) was added to a vial, heated in a boiling water bath for 18 min, and then cooled to room temperature before use.

Chelation of $^{99m}$Tc by the conjugate was achieved by injecting 1 ml of $^{99m}$Tc-labeled sodium pertechnetate (15 mCi) into the vial and heating for ~18 min in a boiling water bath (Scheme 1). The solution was allowed to cool to room temperature and stored in the dark until use on the same day. Following chelation to $^{99m}$Tc, corresponding conjugates are prefixed with $^{99m}$Tc to indicate radiolabeling.

C. Receptor Binding Studies Using Radio-Imaging Conjugates

CRL-1, CRL-2, CRL-3 and CRL-4 were chelated to $^{99m}$Tc and tested for binding using two transfected cell lines of HEK-CCK2R (HEK-293 CCK2R) and HEK-CCK2R splice cell line (HEK CCK2i4svR), obtained from Dr. Mark Hellmich (University of Texas at Galveston). Cells were cultured in Dulbecco's modified Eagles (Gibco) supplemented with 10% Fetal Bovine Serum and G418 disulfate (SIGMA; 400 μg/ml), 1% penicillin/streptomycin at 37° C. in a humidified 95% air, 5% $CO_2$ atmosphere.

Competition studies were performed using 100 fold excess of free Z-360 containing corresponding peptide linker and no chelating moiety. HEK 293 CCK2R and HEK CCK2i4svR were seeded onto 24 well plates and allowed to become confluent over 48-72 hours. Spent medium in each well was replaced with 0.5 ml fresh media containing 0.5% BSA and increasing concentrations of the test article. After incubating for 1 h at 37° C. cells were rinsed with incubation solution (2×1.0 ml) to remove any unbound radioactivity. Cells were then resuspended on 0.5 ml 0.25 N NaOH and cell radioactivity was counted using a γ-counter. The dissociation constant ($K_D$) was calculated using a plot of cell bound radioactivity versus the concentration of the radiotracer using Graphpad Prism 4 and assuming a non-cooperative single site binding equilibrium.

Figure 2:
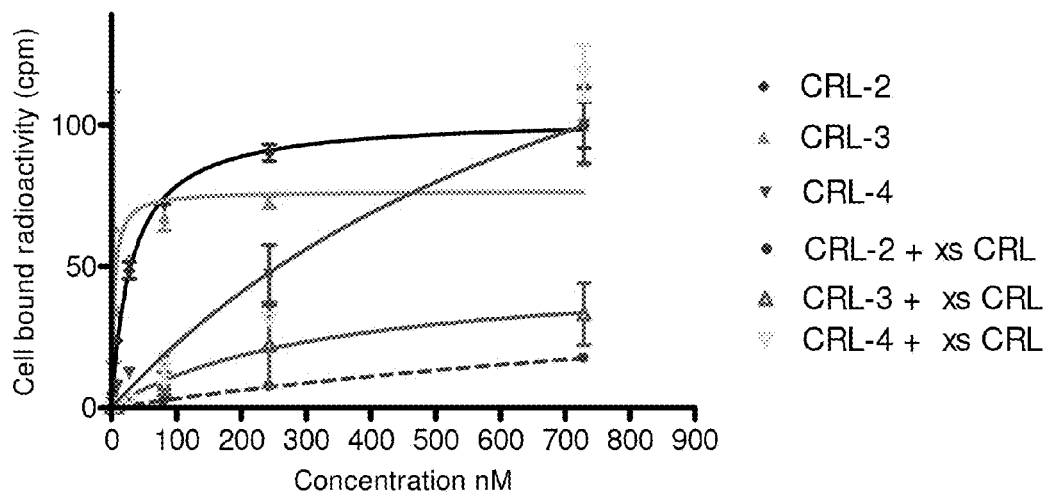
FIG. 2 graphically displays the binding of CRL-2, CRL-3 and CRL-4 to HEK CCKi4svR tumor cells.

As shown in FIG. 1 and FIG. 2, each of the conjugates bound to receptor-expressing cells with high affinities in the low nano molar range (as further supported by the data displayed in Table 2).

TABLE 2

Summary of binding affinity (Kd in nM) for radio-imaging $^{99m}$Tc conjugates of CRL-1, 2, 3, and 4

| Conjugate No. | Kd (nM) HEK-293-CCK2R Cells | Kd (nM) HEK-293-CCKRi4svR Cells |
|---|---|---|
| CRL-1 $^{99m}$Tc | 16 | * |
| CRL-2 $^{99m}$Tc | 46 | 31 |
| CRL-3 $^{99m}$Tc | 30 | 4 |
| CRL-4 $^{99m}$Tc | 270 | * |

*$K_d$ could not be determined due to high levels of non-specific binding.

As shown in FIG. 1 and FIG. 2, the solid line represents the cell bound radioactivity in the experimental group while the dashed line represents the binding in presence of free Z-360. As can be seen, the inclusion of the peptidosaccharo monomer 16 (PS) was found to increase the water solubility of the overall conjugate resulting in significantly higher specificity as seen in the comparison between competition for CRL-1 $^{99m}$Tc and CRL-2 $^{99m}$Tc. However this also resulted in a decrease in the binding affinity of conjugate CRL-2 $^{99m}$Tc which may be attributed to steric effects from the bulkiness of the PS interfering with ligand binding. Addition of an octanoic acid spacer between the PS monomers and the targeting ligand resulted in an improvement in binding affinity for CRL-3 $^{99m}$Tc. As a result of high affinity and specificity in receptor expressing cells, CRL-3 $^{99m}$Tc was used for subsequent radio-imaging experiments in vivo.

D. In Vivo Radio-Imaging and Analysis of Biodistribution

In Vivo Radio-Imaging

In order to test the in vivo specificity of CRL-3 chelated with $^{99m}$Tc, HEK CCK2R and CCK2i4svR subcutaneous tumors were produced in nude mice according to known methods. Athymic female nu/nu mice were purchased from Harlan Laboratories and maintained on normal rodent chow and housed in a sterile environment on a standard 12 hour light and dark cycle for the duration of the study. All animal procedures were approved by the Purdue Animal Care and Use Committee in accordance with NIH guidelines.

Figures 3A, 3B:
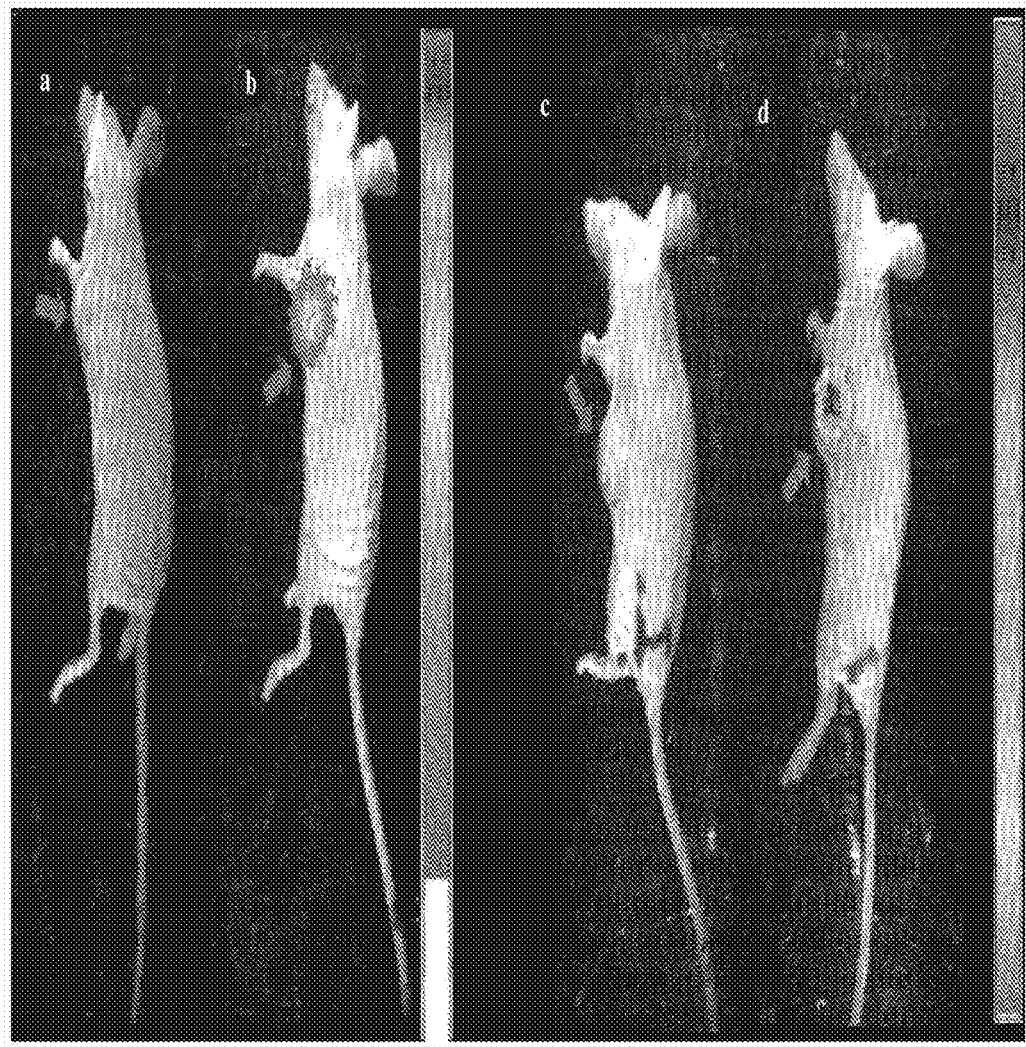
FIGS. 3A-B display the overlay of radio-images over white light images of mice, injected with CRL-3 $^{99m}$Tc displaying the preferential binding of CCK2R conjugates to tumor cells.

150 microcurie of CRL-3 $^{99m}$Tc was injected intravenously into each mouse. FIGS. 3A-B show an overlay of whole-body radio-images on white light photographs of mice bearing images of HEK CCK2R (a, b) and HEK CCKRi4sv (c, d) tumor xenografts in nu/nu mice two hours after the administration of CRL-3 $^{99m}$Tc. Kidneys were shielded with a lead plate. Mice a and c had the radioactive conjugate administered along with 100 fold of free unlabeled targeting ligand. In mice b and d, only the radio-conjugate CRL-3 $^{99m}$Tc was administered. Arrows indicate location of the tumor.

As shown in FIGS. 3A-B, and specifically in mice b and d shown therein, the radio-conjugate accumulated mainly in the receptor expressing tumor with little or no accumulation in other tissues except the kidney, signifying exceptional specificity to the tumor. Additionally, as shown in mice a and c, each of which were pre-injected with excess un-labeled targeting ligand to block the receptors, the in vivo specificity of the radiolabeled conjugate was significant.

Bio-Distribution

Figure 4A:
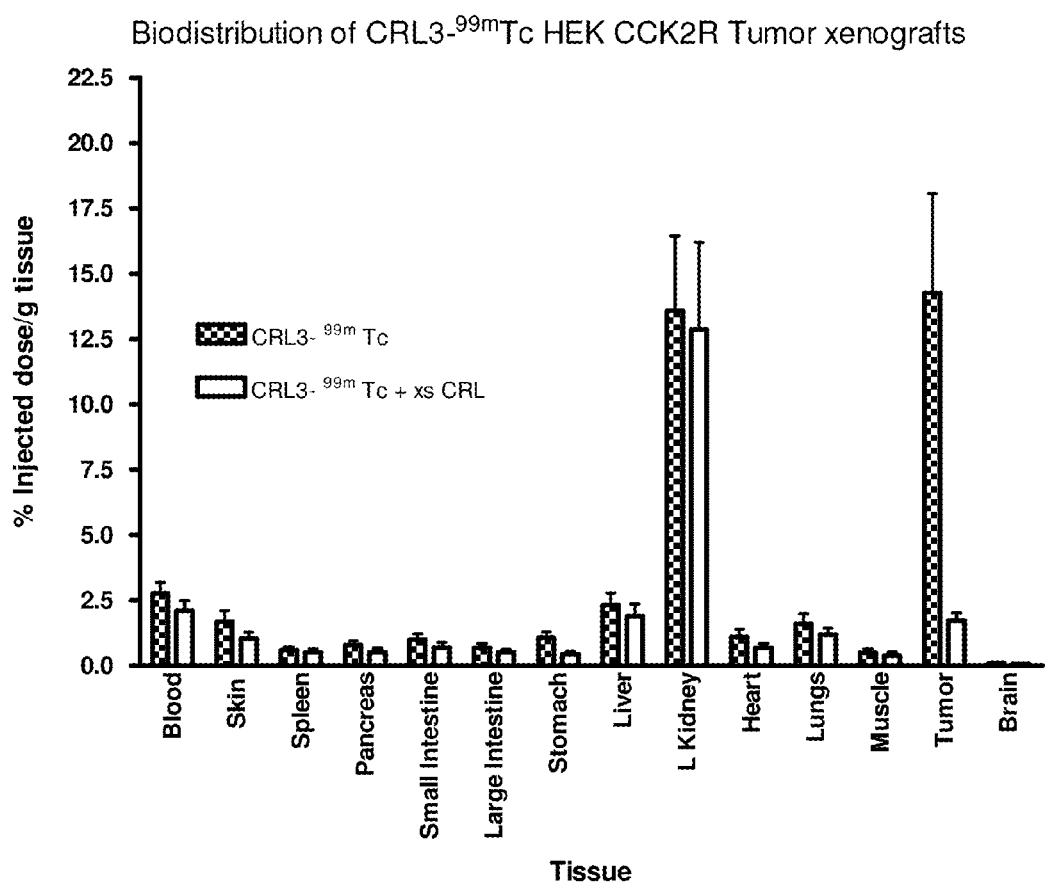
FIGS. 4A-B are bar diagrams displaying the bio-distribution of CRL-3 $^{99m}$Tc when injected to mice having HEK CCK2R tumors (FIG. 4A) and HEK CCKRi4sv tumors (FIG. 4B).
Figure 4B:
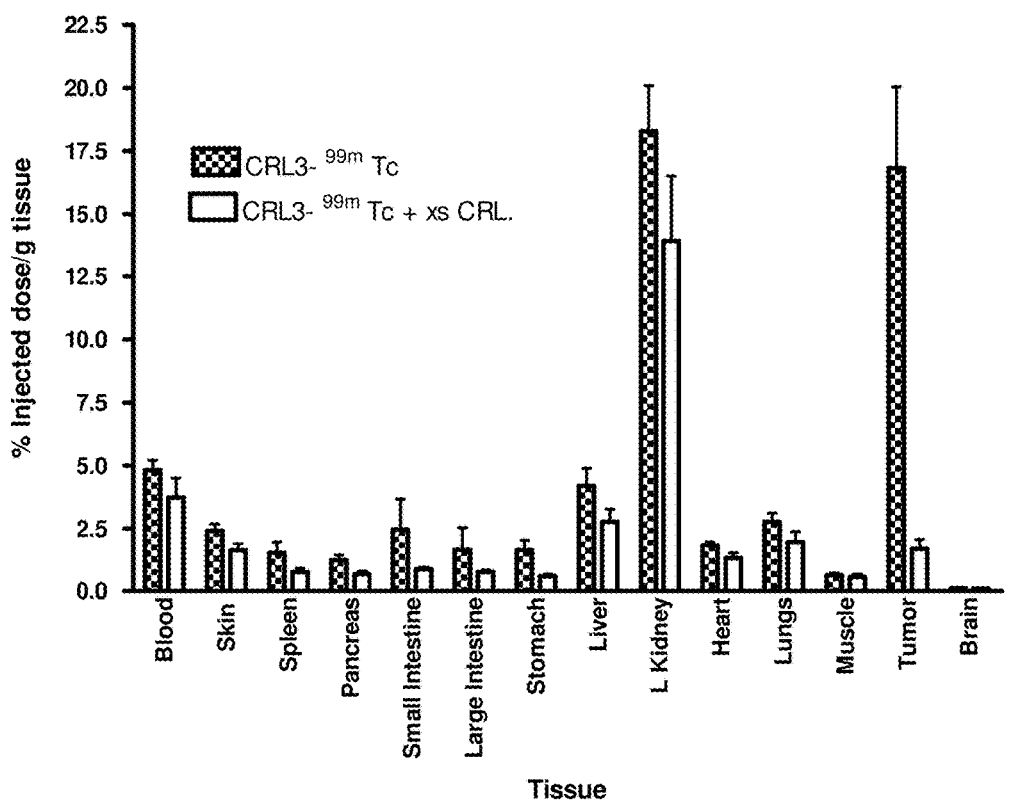

Following the above radio-imaging studies, animals were dissected and selected organs/tissues were collected into pre-weighed γ-counter tubes. Radioactivity of weighed tissues and test compounds were counted in a γ-counter. CPM values were decay corrected and results were calculated as % injected dose per gram of wet tissue (% ID/g). FIGS. 4A-B show the bio-distribution of the CRL-3 $^{99m}$Tc in mice having HEK CCK2i4svR and HEK CCK2R tumors. Error bars represent the standard deviation (n=5 mice/group). As will be appreciated, only the tumor and kidneys show excessive accumulation of radiotracer in mice with HEK CCK2R and HEK CCK2i4svR tumors.

Time Course Bio-Distribution

Figure 5:
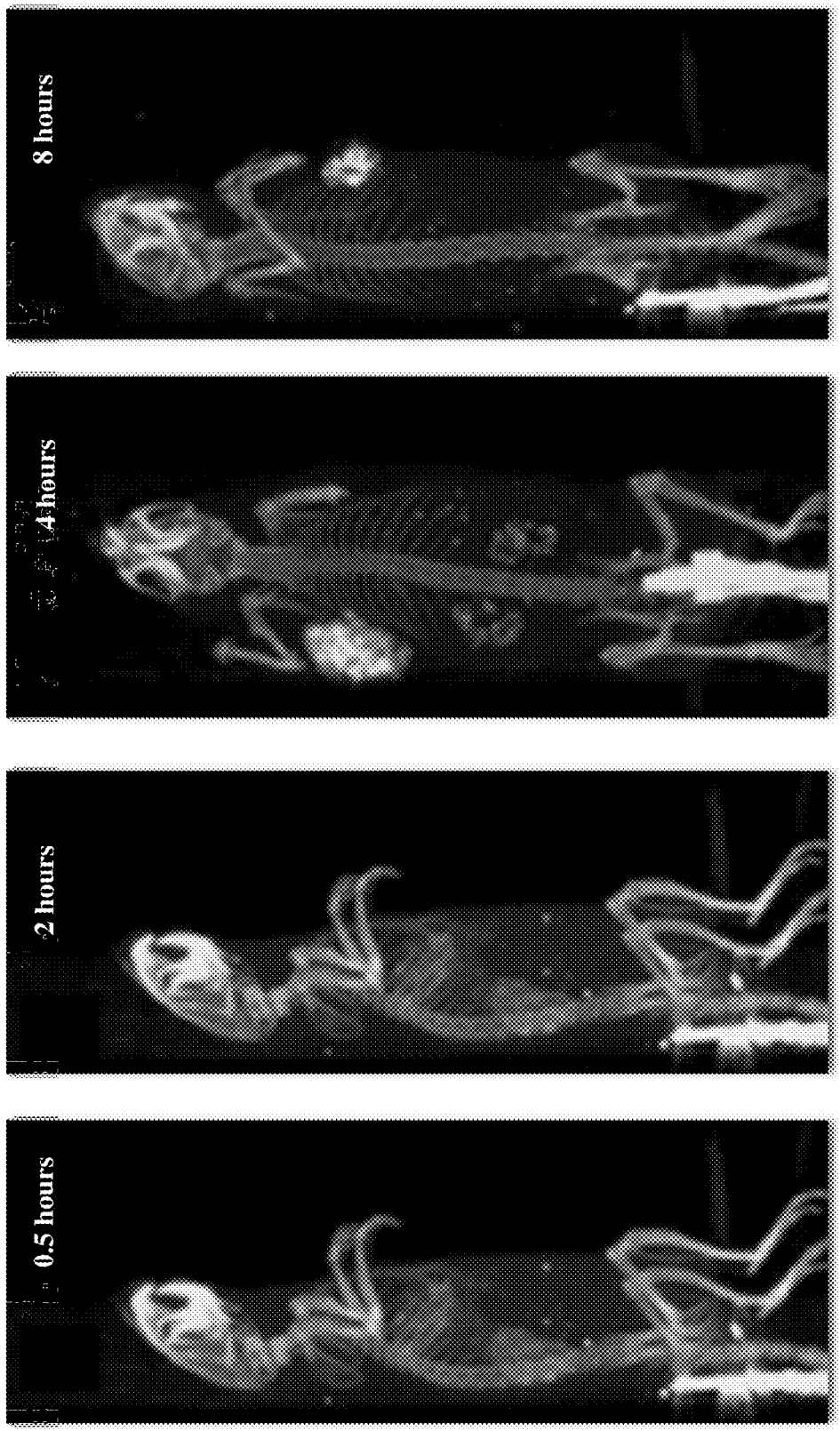
FIG. 5 contains SPECT-CT images showing the rate of clearance of the CRL-3 $^{99m}$Tc from tumor-bearing mice. Mice implanted with HEK CCK2R tumor xenograft were injected with 5.55 mBq (150 µCi) the CRL-3 $^{99m}$Tc and imaged 0.5, 2, 4, and 8 hours post tail vein injection.

Since small molecules are often excreted via the kidneys[43], we next elected to determine whether uptake of CRL-3 $^{99m}$Tc in the kidneys might be transient. As seen in the SPECT-CT images of FIG. 5, the CRL-3 $^{99m}$Tc content of the kidneys decreased significantly over time, whereas uptake in the tumor mass was relatively stable. By 24 h post tail vein injection, tumor to tissue ratios of CRL-3 $^{99m}$Tc in the muscle, heart, skin, blood, liver, and spleen were 90, 83, 30, 61, 4 and 14, respectively (see also Table 3). These data suggest that only CCK2R positive tissues retain the CRL-3 $^{99m}$Tc, and therefore, that radiation damage to normal tissues should be minimal.

TABLE 3

Tissue distribution of CRL-3 $^{99m}$Tc in mice with subcutaneous HEK 293-CCK2R cells at 0.5, 2, 4, 8 and 24 h post injection. Uptake of radioactivity is expressed as percent injected dose per gram of wet tissue. (n = 5 for hours 0.5, 4, 8, and 24; n = 10 for hour 2 time point).

| Organ | 0.5 h | 2 h | 4 h | 8 h | 24 h |
|---|---|---|---|---|---|
| Blood | 5.8 ± 2.7 | 1.9 ± 0.97 | 1.7 ± 0.39 | 0.24 ± 0.19 | 0.10 ± 0.062 |
| Skin | 2.3 ± 1.2 | 1.0 ± 0.41 | 1.1 ± 0.23 | 0.42 ± 0.22 | 0.21 ± 0.13 |
| Spleen | 2.1 ± 1.2 | 0.69 ± 0.70 | 1.4 ± 0.41 | 0.65 ± 0.42 | 0.45 ± 0.39 |
| Pancreas | 1.3 ± 0.62 | 0.69 ± 0.84 | 0.29 ± 0.19 | 0.10 ± 0.065 | 0.053 ± 0.031 |
| Small Intestine | 1.2 ± 0.63 | 0.52 ± 0.28 | 0.52 ± 0.085 | 0.19 ± 0.10 | 0.13 ± 0.081 |
| Large Intestine | 1.0 ± 0.52 | 0.46 ± 0.20 | 0.53 ± 0.11 | 0.24 ± 0.16 | 0.13 ± 0.086 |
| Stomach | 1.2 ± 0.61 | 0.58 ± 0.32 | 0.56 ± 0.16 | 0.24 ± 0.15 | 0.15 ± 0.088 |
| Liver | 6.7 ± 3.6 | 2.5 ± 2.4 | 4.1 ± 0.64 | 1.9 ± 1.2 | 1.4 ± 1.4 |
| Left Kidney | 11.2 ± 6.1 | 8.4 ± 4.6 | 13.4 ± 2.1 | 6.0 ± 3.1 | 2.6 ± 1.6 |
| Right Kidney | 11.4 ± 6.3 | 7.6 ± 4.4 | 12.8 ± 1.8 | 5.7 ± 3.0 | 2.6 ± 1.7 |
| Heart | 2.3 ± 1.5 | 0.68 ± 0.47 | 0.59 ± 0.18 | 0.14 ± 0.078 | 0.076 ± 0.052 |
| Lungs | 3.2 ± 1.7 | 1.2 ± 0.55 | 1.0 ± 0.23 | 0.29 ± 0.15 | 0.18 ± 0.12 |
| Muscle | 0.8 ± 0.37 | 0.29 ± 0.096 | 0.3 ± 0.04 | 0.093 ± 0.048 | 0.070 ± 0.080 |
| Brain | 0.13 ± 0.072 | 0.051 ± 0.019 | 0.053 ± 0.016 | 0.064 ± 0.12 | 0.0076 ± 0.0053 |
| Tumor | 7.4 ± 4.6 | 8.1 ± 5.1 | 12.0 ± 2.0 | 8.5 ± 4.9 | 6.3 ± 3.7 |

E. Conjugates Comprising Z-360 and Optical Imaging Agents

Given the specificity of Z-360 in targeting CCK2R expressing tumors, targeted optical imaging agents were developed and tested. Targeted, fluorescently-tagged imaging conjugates have the unique capability of being used as a diagnostic agent as well as a tool to guide surgeons during inter-operative surgery for the removal of malignant tissue. To this end, three exemplary optical dyes (fluoresceine, rhodamine NHS ester, and LS-288) were linked to Z-360. The structure of the resulting conjugates 17-19 are shown below:

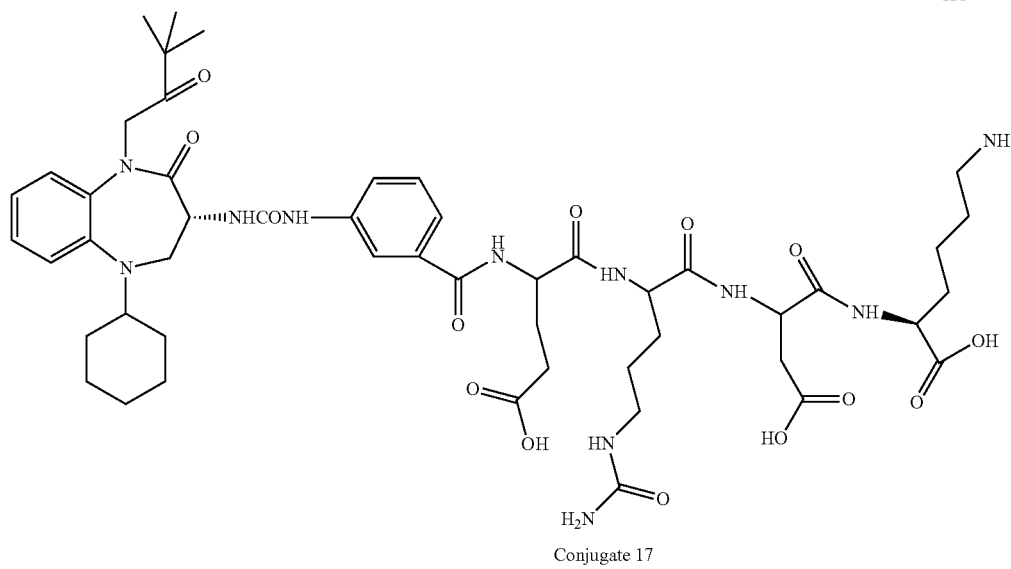

Conjugate 17

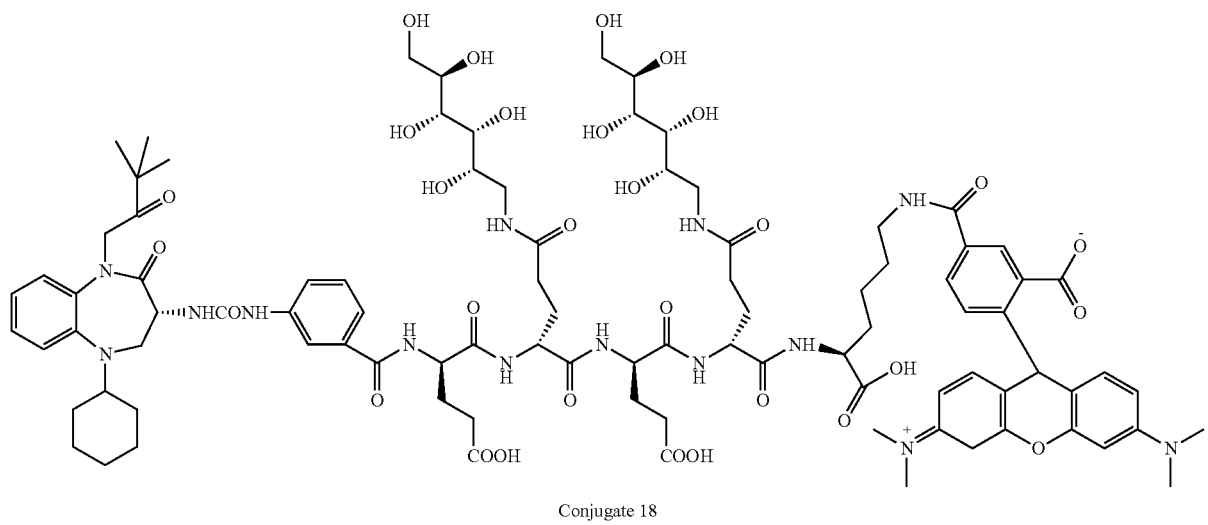

Conjugate 18

-continued

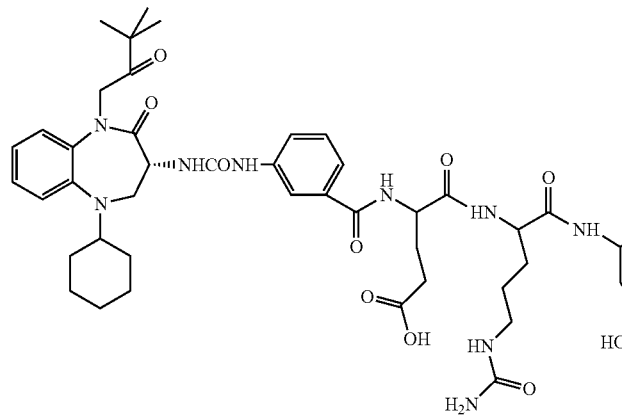

Conjugate 19

As shown above, conjugate 17 correlates to Z-360 linked to FITC (CRL-FITC), i.e., having fluoresceine isothiocyanate conjugated thereto; conjugate 18 correlates to Z-360 linked to rhodamine (CRL-Rhodamine), i.e., having rhodamine NHS ester conjugated thereto; conjugate 19 correlates to Z-360 linked to LS288 (CRL-LS288), i.e., having LS-288-COOH conjugated thereto.

Synthesis of CRL

To prepare the optical imaging conjugates, the targeting ligand Z-360 was attached to a tetrapeptide sequence: glutamic acid-arginine-aspartic acid-lysine to a Cholecystokinin Receptor Ligand (CRL). Z-360 was synthesized as described above (see, e.g., Scheme 1). The peptide spacer was synthesized as follows. H-Lys (Boc)-2-Cl-Trt resin (100 mg, 0.075 mmol) was swollen in dichloromethane (2×5 ml) while bubbling under argon. A solution of Fmoc-Asp (OtBu)-OH (2.5 eq), HATU (2.5 eq), and DIPEA (5 eq) in DMF was added. The resulting solution was bubbled under argon for 4 hours, drained, and the resin washed with DMF (3×5 ml) and i-PrOH (3×5 ml). Fmoc deprotection was carried out using 20% piperidine in DMF (3×10 ml). The deprotection solution was removed, and the resin washed again with DMF (3×5 ml) and i-PrOH (3×5 ml). Kaiser tests were conducted to assess coupling and deprotection. The next amino acid in the spacer, Fmoc-Arg(pbf)-OH, HATU, and DIPEA were then added in the amounts described above, and this procedure was repeated until all the amino acids and Z-360 (1.5 eq) were coupled to the growing spacer on the resin. The resin was washed with DMF (3×5 ml) and i-PrOH (3×5 ml), dichloromethane (2×5 ml), acetic acid (1×5 ml), and MeOH (1×5 ml), and allowed to dry under nitrogen. The peptide was then cleaved from the resin using a mixture of 95% TFA, 2.5% $H_2O$, and 2.5% triisopropylsilane. The solution was bubbled twice under nitrogen for 15 minutes, drained, concentrated, and then precipitated by addition of cold diethyl ether. Crude product was collected by centrifugation, washed three more times with diethyl ether, dried under vacuum and then purified by preparative reverse phase HPLC (Waters, xTerra $C_{18}$ 10 μm; 19×250 mm column mobile phase A=20 mM ammonium acetate buffer, pH 7, B-acetonitrile, gradient 0-50% B in 30 minutes 13 ml/min=280 nm). Pure fractions were analyzed by LC-MS and HR-MS pooled, and lyophilized to furnish CRL (compound 1 in Scheme 4 below).

Scheme 4

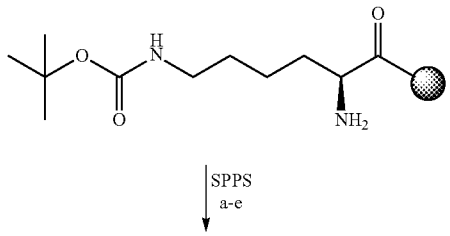

SPPS
a-e

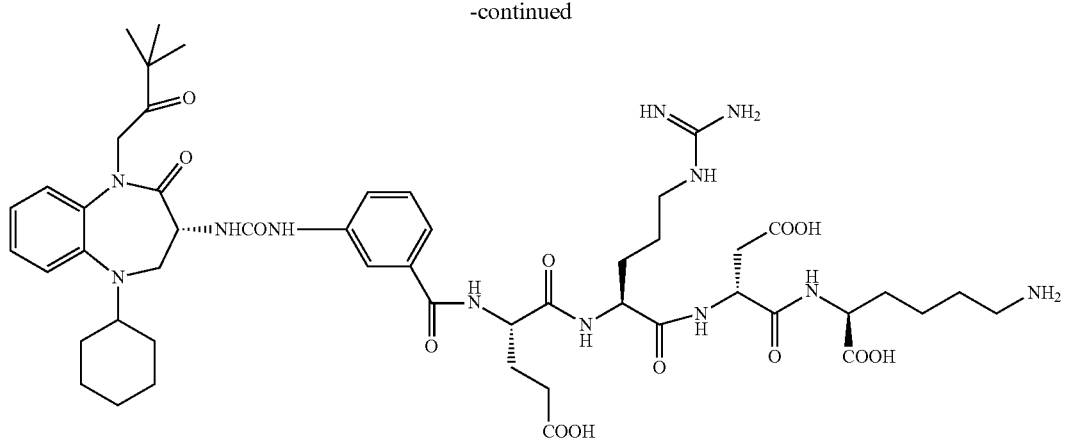

1

Scheme 4: Reagents and conditions for synthesis of CRL: (a) (i) DCM wash (ii) Fmoc-Asp(OtBu)-OH, HATU, DMF/DIPEA, 4 h. (b) (i) 20% piperidine/DMF, 30 min; (ii) Fmoc-Arg(pbf)-OH, HATU, DMF/DIPEA, 4 h. (c) (i) 20% piperidine/DMF, 30 min; (ii) Fmoc-Glu(OtBU)-OH, HATU, DMF/DIPEA, 4 h. (d) (i) 20% piperidine/DMF, 30 min; (ii) Z-360, HATU, DMF/DIPEA, 4 h. (e) TFA/H2O/TIPS (95:2.5:2.5), 30 mins.

Synthesis of Conjugate 19

One equivalent of LS-288 COOH was dissolved in anhydrous DMSO (100 µL) containing five equivalent of diisopropylethylamine, and one equivalent of HATU was allowed to stir for 25 minutes under argon atmosphere. A threefold molar excess of CRL was added and stirred at room temperature for overnight as outlined in Scheme 5. The product was then precipitated by addition of isopropanol followed by centrifugation. The precipitate was redissolved in DMSO and the crude products were purified by preparative RP-HPLC using a Waters, xTerra C18 10 µm; 19×250 mm column with a gradient mobile phase of A=20 Mm ammonium acetate buffer; B=Acetonitrile; λ=280 nm; solvent gradient 5% B to 80% B in 30 minutes. Pure fractions were analyzed by LC-MS and LR-MS pooled and lyophilized to furnish conjugate 19 (compound 3 (CRL-LS288) in Scheme 5 below).

Scheme 5

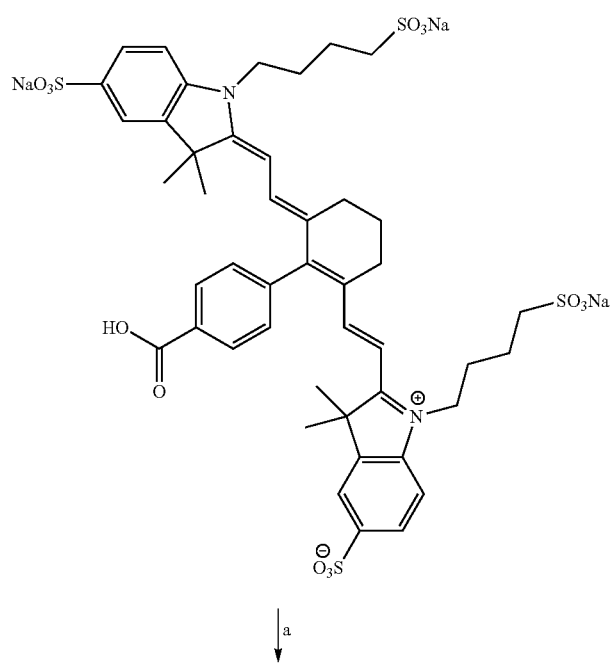

↓ a

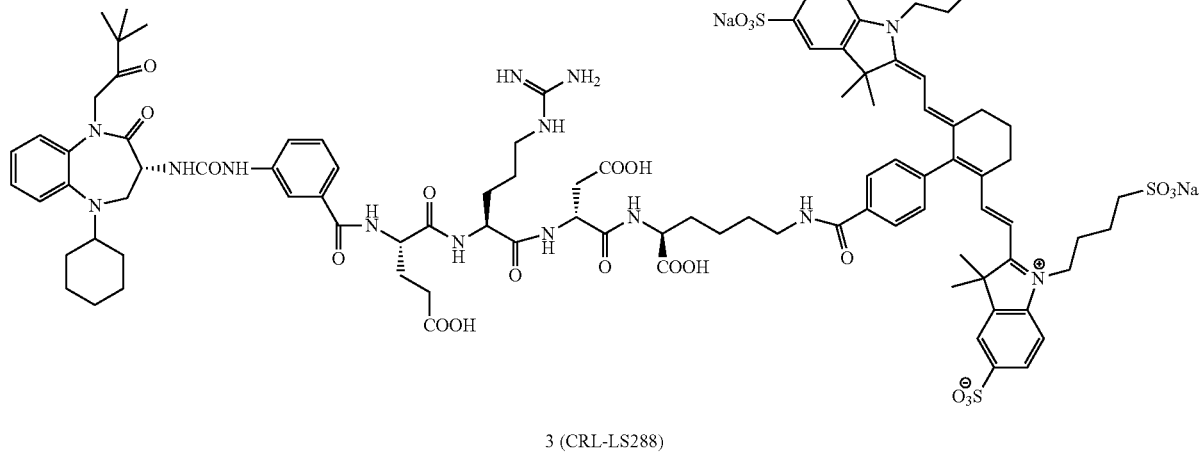

3 (CRL-LS288)

Scheme 5: Reagents and conditions for synthesis of conjugate 19 (CRL-LS288): (a) (i) HATU, DIPEA, DMSO, r.t. 25 mins, (ii) CRL spacer (3 eq) stir overnight (iii) isopropanol, centrifugation.

Starting materials of 4 mg of Dye (LS288-COOH), 1.46 mg HATU, and 4.5 mg of peptide yielded 1.2 mg of final conjugate (yield approximately 15%). The remaining dye conjugates (conjugates 17 and 18) were synthesized in a method analogous to the one described above.

F. Receptor Binding Studies Using Optical Imaging Conjugates

Figure 6A:
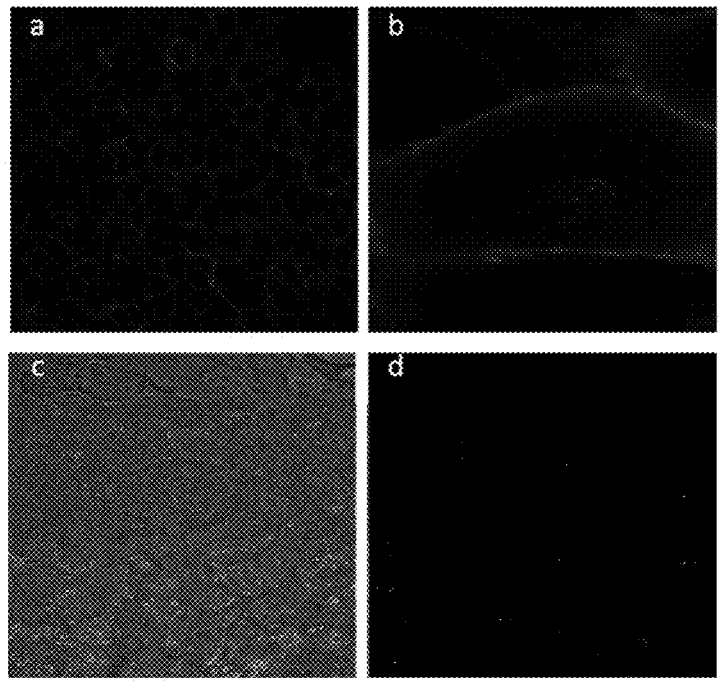
FIGS. 6A-B show the binding of conjugate 18 to HEK CCK2R cells (FIG. 6A) and HEK CCKi4svR cells (FIG. 6B). Plates a and e show the binding of 10 nM conjugate 18; plates b and f show zoom in of the binding of 10 nM conjugate 19; plates c and g show the binding of 10 nM conjugate 18+excess competitor trans illumination; and plates d and h show the binding of 10 nM conjugate 18+excess competitor.
Figure 6B:
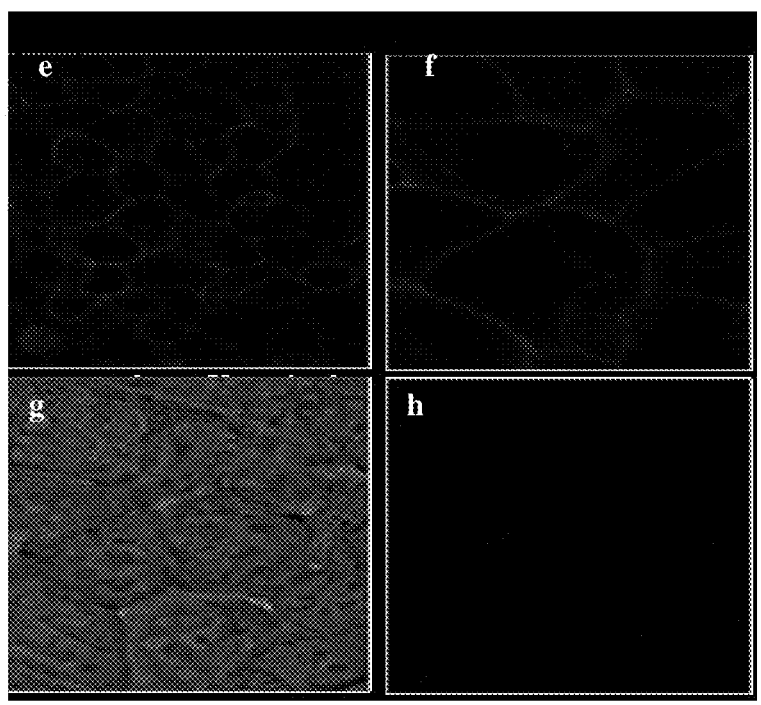

FIGS. 6A-B display the results of binding by conjugate 18 (CRL-Rhodamine) to HEK CCK2R cells as displayed in plates a-d in FIG. 6A, and HEK CCKi4svR cells as displayed in plates e-h in FIG. 6B. Specifically, plates a and e show the binding of 10 nM conjugate 18; plates b and f show zoom in of the binding of 10 nM conjugate 18; plates c and g show the binding of 10 nM CRL-Rhodamine+excess competitor trans illumination; and plates d and h show the binding of 10 nM conjugate 18+excess competitor. Plates d and h show that all fluorescence is abolished when the CCK2R receptors are pre-blocked with CRL indicating that the fluorescent conjugates bind specifically via the CCK2 receptor.

Figure 7A:
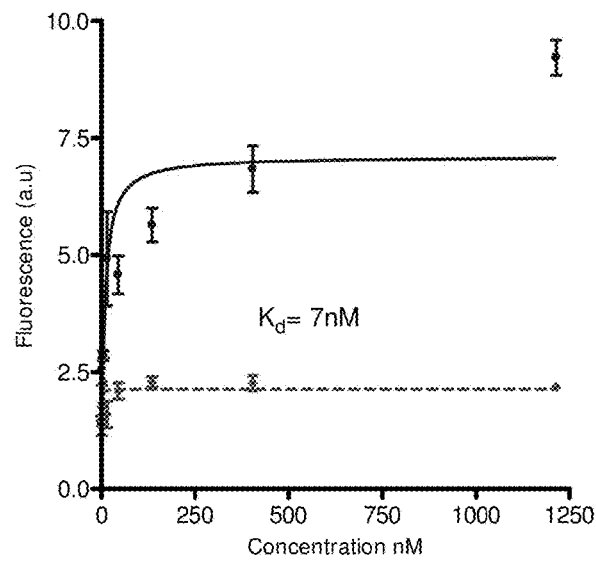
FIGS. 7A-B are line graphs displaying binding of conjugate 19 (CRL-LS288) to HEK CCKRi4sv tumor cells and HEK CCK2R tumor cells, respectively. The solid line represents the cell-bound fluorescence in the experimental group while the dashed line represents the binding in presence of free CRL.
Figure 7B:
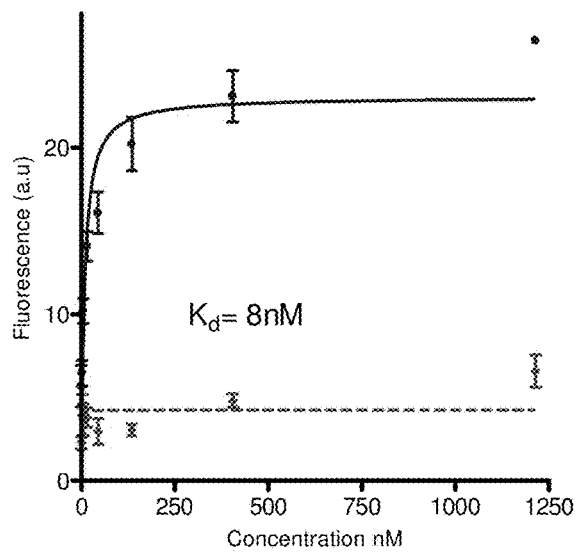

FIGS. 7A-B display the binding of conjugate 19 (CRL-LS288) using two transfected cell lines of HEK-CCK2R (HEK-293 CCK2R) and HEK-CCK2R splice cell line (HEK CCKi4svR), obtained from Dr. Mark Hellmich (University of Texas at Galveston). Competition studies were performed using 100 fold excess of free Z-360 containing corresponding peptide linker and no fluorescent dye. The resulting binding affinities are shown in FIGS. 7A and 7B. As shown in each of FIGS. 7A-B, the solid line represents the cell-bound fluorescence in the experimental group while the dashed line represents the binding in presence of free Z-360.

Figure 8A:
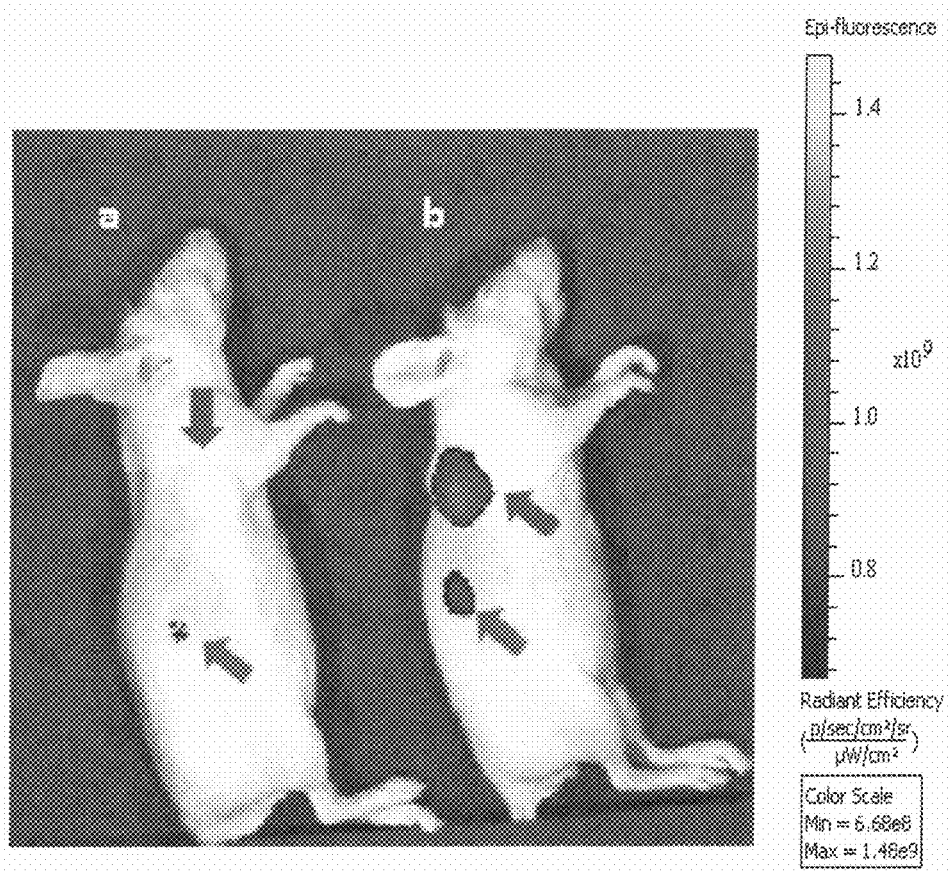
Figure 8C:
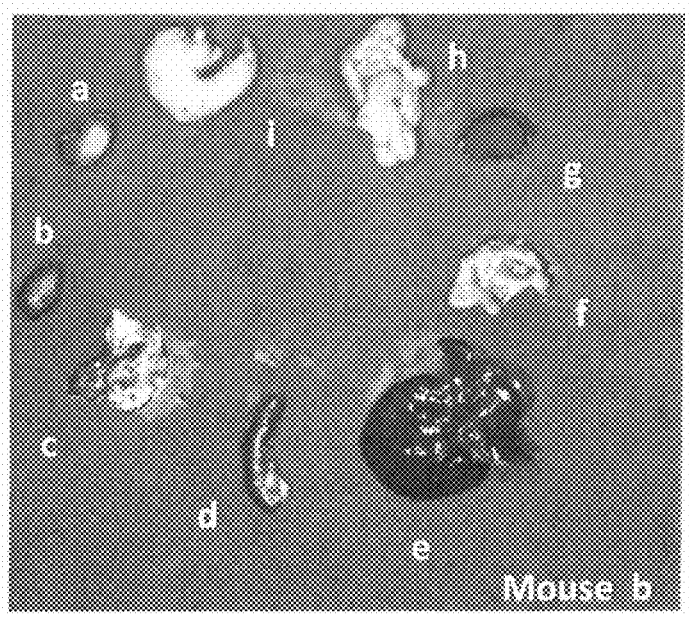
Figure 9B:
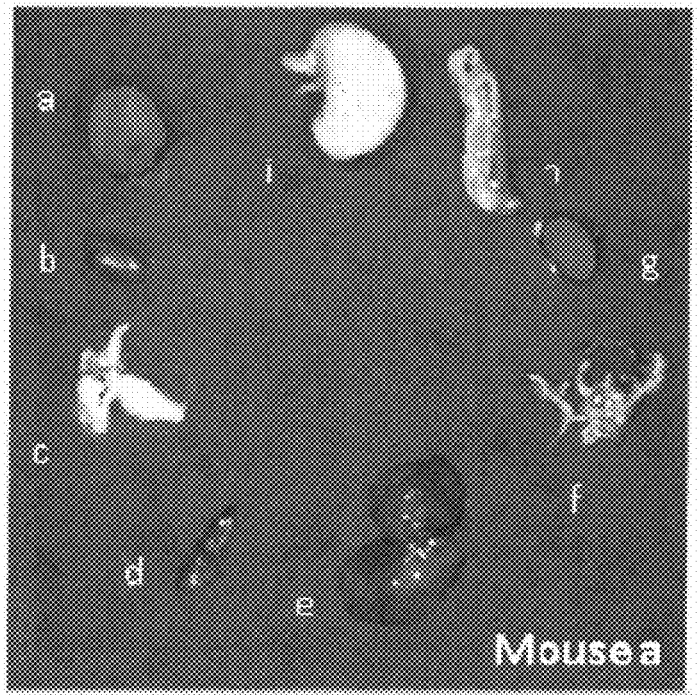
Figure 9C:
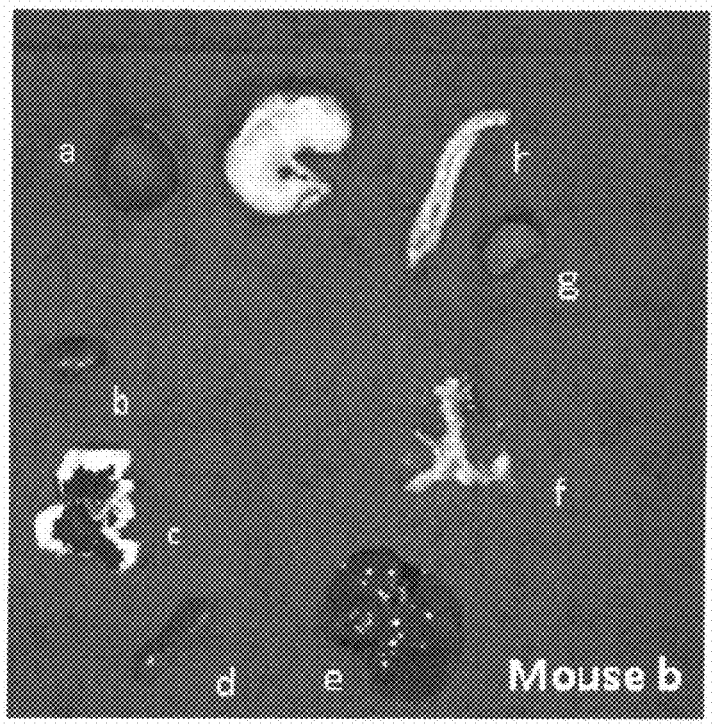

FIGS. 8A-C display the binding of conjugate 19 in CCK2R tumors from mice having HEK-CCK2R (HEK-293 CCK2R) tumors. Mouse a was pre-injected with excess unlabeled Z-360-peptidoglycan conjugate prior to treating with conjugate 19, while mouse b was injected with 10 nmol of conjugate 19. Tumors and kidneys are shown with arrows. Dissected organs are labeled as follows: a-tumor, b-heart, c-lungs, d-spleen, e-liver, f-pancreas g-kidneys, h-small intestines, i-stomach.

FIGS. 9A-D display the binding of conjugate 19 in CCK2i4svR tumors from mice having HEK-CCK2R splice cell line (HEK CCK2i4svR) tumors. Mouse a was injected with 10 nmol of conjugate 19, while mouse b was pre-injected with excess unlabeled Z-360-peptidoglycan conjugate prior to injection with 10 nmol of conjugate 19, and mouse c containing a receptor negative KB tumor was also injected with 10 nmol conjugate 19. Tumors and kidneys are shown with. Dissected organs are labeled as follows a-tumor, b-heart, c-lungs, d-spleen, e-liver, f-pancreas g-kidneys, h-small intestines, i-stomach.

Imaging CCK2R-Positive Metastasis Using Conjugate 19

Figure 10:
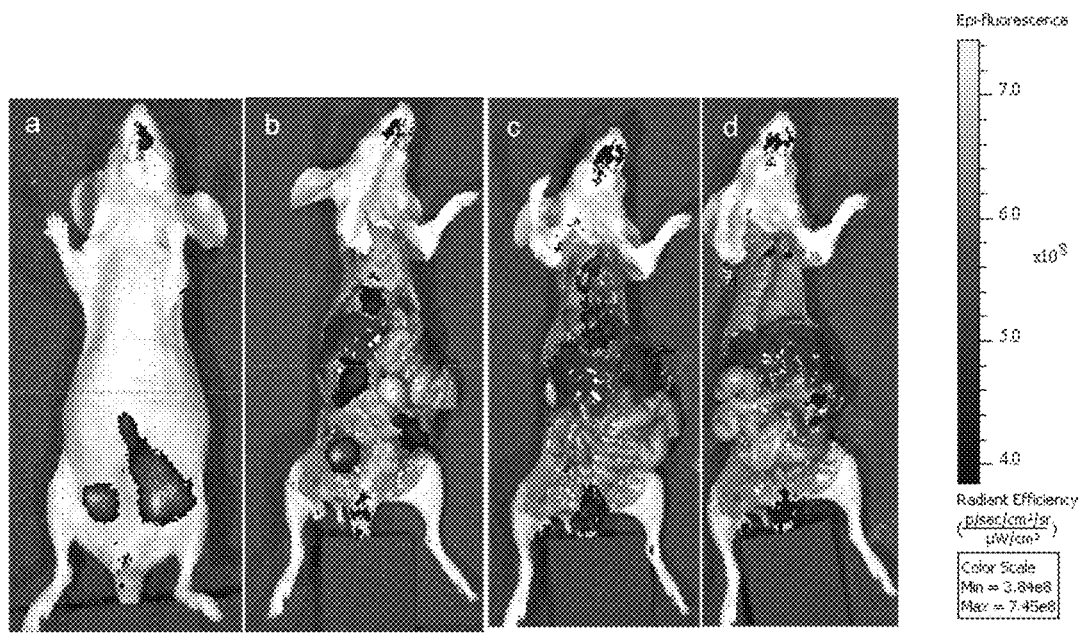
FIG. 10 shows images of mice with metastatic HEK CCK2i4svR tumors following intravenous injection of conjugate 19. Images were taken of the mouse before (a) and after (b, c, d) various sequential stages of tumor resection guided by the fluorescence of the tumor-targeted NIR dye.

In order to determine if conjugate 19 would be useful in identifying metastatic disease, it was used for imaging a murine metastasis model. Metastases were induced by injecting HEK-CCK2i4svR cells into the peritoneum of nu/nu mice and allowing the tumors to attach and proliferate for 3 weeks. Then, following tail vein injection of 10 nmol conjugate 19, mice were imaged both before and after various stages of tumor resection. As seen in FIG. 10a, large tumor nodules could be readily detected in the intact mice; i.e. prior to removal of skin and underlying tissue. In fact, validation that the fluorescent spots seen in the intact mice accurately revealed the locations tumor nodules within the peritoneum was confirmed by removing the occluding skin and peritoneal lining and then re-imaging the animals (FIG. 10b). Sequential fluorescence-guided surgical removal of the remaining fluorescent masses then yielded the images shown in FIGS. 10c and 10d.

Figure 11:
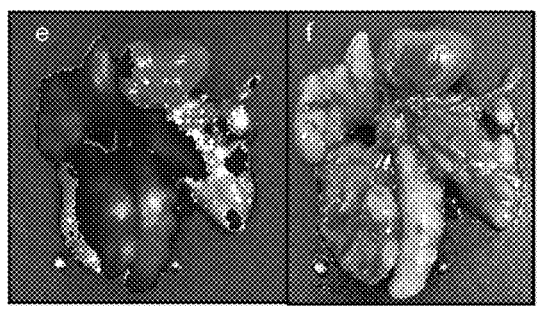
FIG. 11 shows fluorescent (left panel) and color (right panel) images of lungs and heart of tumor-bearing mice shown in FIG. 10.
Figure 12:
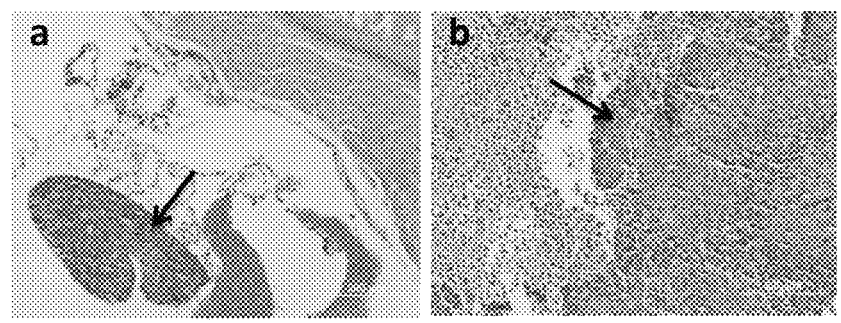
FIG. 12 shows hematoxylin & eosin staining of fluorescent nodules resected from a) the lungs, and b) the peritoneal cavity of the tumor bearing mouse shown in FIG. 10. Arrows point to regions containing malignant disease.

Because of the density of the skin and bones covering the thoracic cavity, lung metastases could not be seen in the intact animals. However, following removal of the rib cage, numerous fluorescent loci were revealed that appeared potentially malignant (FIG. 10c & FIG. 11). To confirm that these fluorescent masses were indeed malignant, fluorescent tissues from both the thoracic and peritoneal cavities were submitted to pathology for hematoxylin and eosin staining. As shown in representative samples in FIG. 12, all lesions that appeared fluorescent proved to be malignant (see arrows), indicating that CRL-LS288 accurately identifies cancer metastases in murine models of malignant disease.

G. Conjugates Comprising Z-360 and Therapeutic Agents

Given the specificity of Z-360 in targeting CCK2R-expressing tumors, even when bound to optical and radio-imaging reagents, conjugates comprising therapeutic agents (tubulysine B hydrazide (TubH; compound 20) and desacetyl vinblastine hydrazide (DAVBH; compound 21)) and were developed and tested for efficacy.

-continued

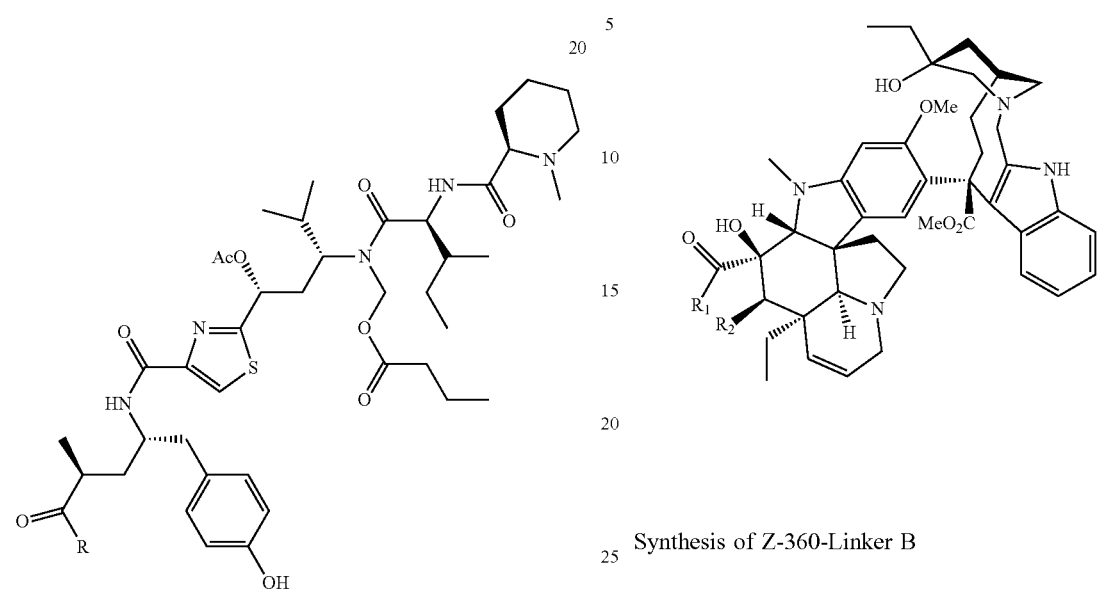

Tubulysin B: R = OH
Tubulysin B hydrazide: R = NHNH₂

Synthesis of Z-360-Linker B

Z-360 was first attached to a linker using the previously described procedure for the radio-imaging agent above to produce Z-360-linker B (Scheme 6 below).

Scheme 6

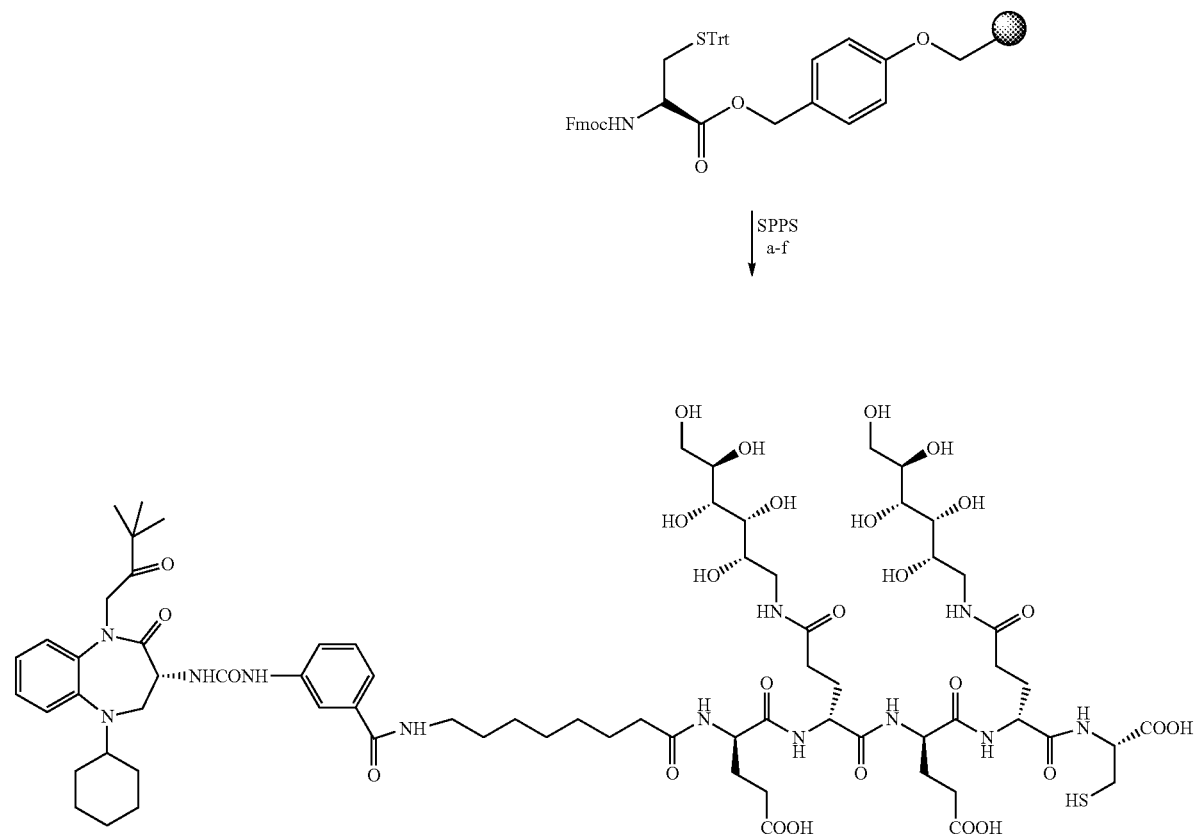

Scheme 6: Synthesis of Z-360-linker B. Reagents and conditions: (a) (i) 20% piperidine/DMF, rt, min; (ii) 3,4,5,6-Di-isopropylidene-1-amino-deoxy(Fmoc-Glu-OH)-D-glucitol, HATU, DIPEA, 4 h; (b) (i) 20% piperidine/DMF, rt, 10 min; (ii) Fmoc-Glu(OtBu)-OH, HATU, DIPEA, 4 h; (c) (i) 20% piperidine/DMF, rt, 10 min; (ii)3,4,5,6-Di-isopropylidene-1-amino-deoxy(Fmoc-Glu-OH)-D-glucitol, HATU, DIPEA, 4 h; (d) (i) 20% piperidine/DMF, rt, 10 min; (ii) Fmoc-Glu(OtBu)-OH, HATU, DIPEA, 4 h; (e)(i) 20% piperidine/DMF, rt, 10 min; (ii) Fmoc-8-amino-octanoic, HATU, DIPEA, 4 h; (f) (i) 20% piperidine/DMF, rt, 10 min; Z-360, HATU, DIPEA, Overnight; i) TFA/H$_2$O/TIPS/EDT (92.5:2.5:2.5:2.5).

Synthesis of Conjugates Comprising Z-360 Linked to Tubulysin B Hydrazide (Compound 22; CRL-TubH)

Disulfide activated prodrugs (tubulysin B hydrazide[39] and desacetyl vinblastine hydrazide[40]) were synthesized according to literature reported procedures.

Into a solution of saturated sodium bicarbonate (2 mL) and HPLC grade water, argon was bubbled for 10 min. With continuous bubbling of argon, Z-360-linker B (36 mg, 0.0226 mmol) was dissolved in argon purged HPLC grade water (2.0 mL) and pH of the reaction mixture was increased to ~7 using argon purged bicarbonate. A solution of disulfide activate-tubulysin hydrazide (12.0 mg, 0.0113 mmol) in THF (2.0 mL) was then added to the reaction mixture. After stirring for 20 min, the progress of the reaction was monitored using analytical RP-HPLC. At this point HPLC indicated that reaction was completed. After removing THF under reduced pressure, Z-360-linker B-TubH (conjugate 22) was purified on a preparative RP-HPLC [A=2 mM ammonium acetate buffer (pH=7.0), B=CH3CN, solvent gradient: 5% B to 80% B in 25 min] to yield requisite product LRMS-LC/MS (m/z): (M+H)+ calcd. for, C117H177N19O38S3, 2553.96; found, 2554.

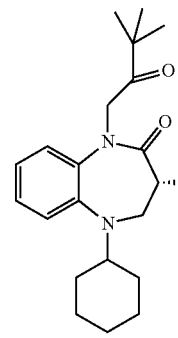
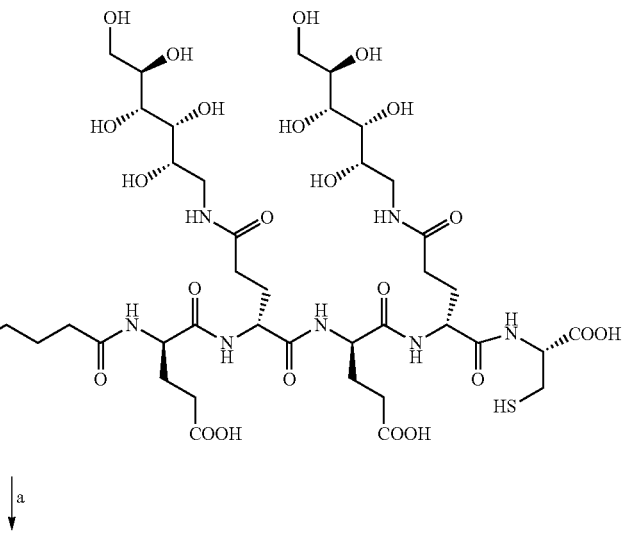
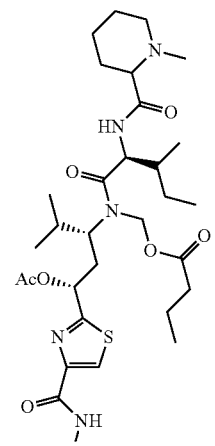

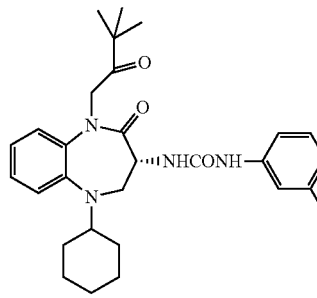
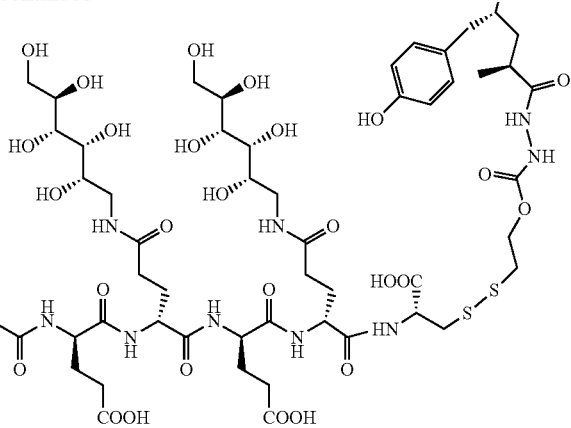

Conjugate 22

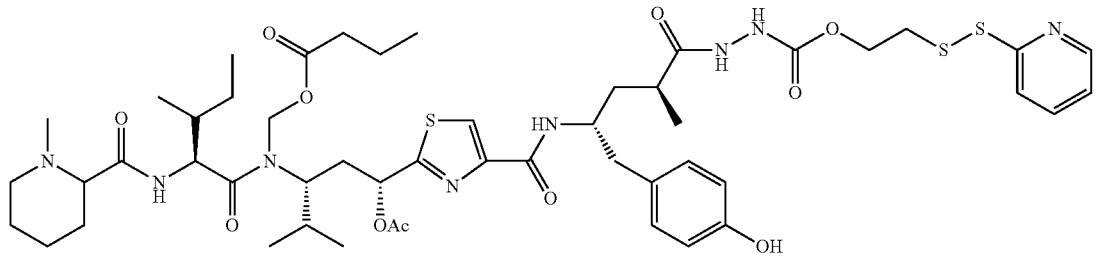

Disulfide activated tubulysin B

Scheme 7: Synthesis of conjugate 22. Reagents and conditions (a) i) H₂O/NaHCO₃ (pH=7.0-7.2), Argon, r.t.; ii) disulfide activated tubulysin B/THF, argon, r.t., 15 mins.

Synthesis of Conjugates Comprising Z-360 Linked to Desacetyl Vinblastine Hydrazide (Conjugate 23; CRL-DAVBH)

Following a similar procedure as described for preparation of conjugate 22, desacetyl vinblastine hydrazide was synthesized from activated vinblastine hydrazide. Z-360-linker B-desacetyl vinblastine hydrazide (conjugate 23) was purified by preparative RP-HPLC [A=20 mM ammonium acetate (pH=7.2), B=CH3CN, solvent gradient: 5% B to 80% B in 30 min], yielding the desired product LRMS (LC/MS) (m/z): calculated for C118H168N18O36S2 2478 (M+H)+; Found 2478.

Conjugate 23

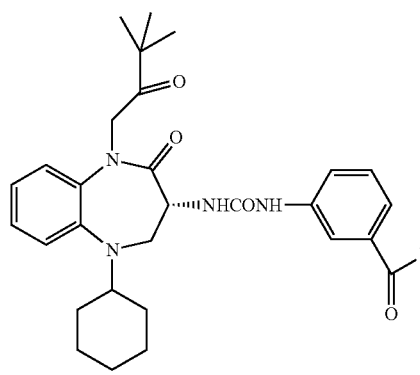
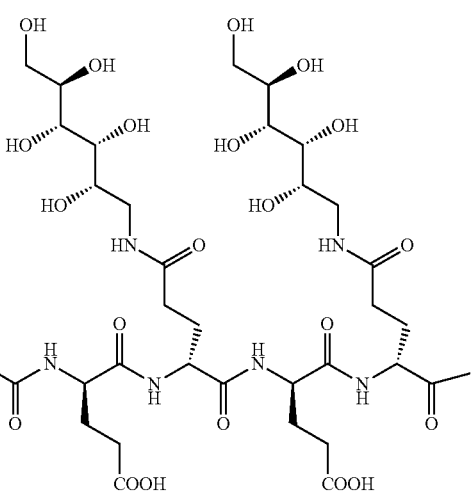

-continued

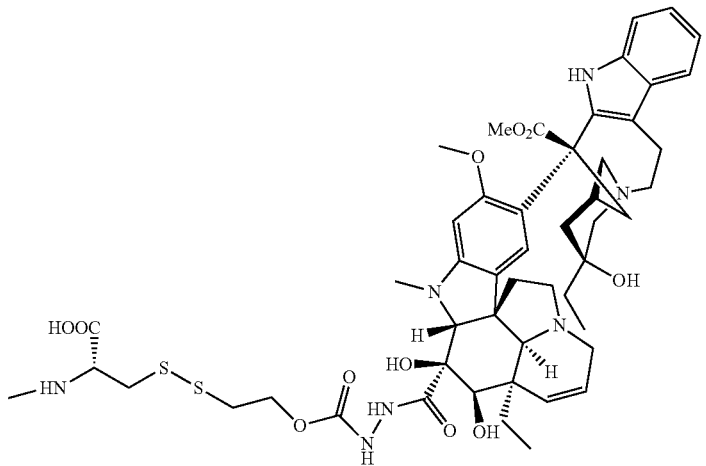

Synthesis of Untargeted Tubulysin Hydrazide and Untargeted Desacetyl Vinblastine Hydrazide Following a similar procedure for preparation of conjugate 22, compounds comprising therapeutic agents that lacked the targeting ligand were produced. Untargeted tubulysin hydrazide (Conjugate 24; Unt-TubH) and untargeted desacetyl vinblastine hydrazide (Conjugate 25; Unt-DAVBH) were synthesized from activated TubH and DAVBH, respectively. Each of these compounds were purified by reverse phase HPLC [A=2 mM ammonium acetate buffer (pH=7.0), B=$CH_3CN$, solvent gradient: 5% B to 80% B in 25 min] to yield requisite product LRMS-LC/MS (m/z): (M+H)$^+$ calcd. For Unt-DAVBH, $C_{89}H_{134}N_{14}O_{32}S_2$, 1976.22; found, 1976 (m/z): (M+H)$^+$ calcd. For Unt-TubH $C_{88}H_{143}N_{15}O_{34}S_3$, 2051.35; Found 2051.

Conjugate 24

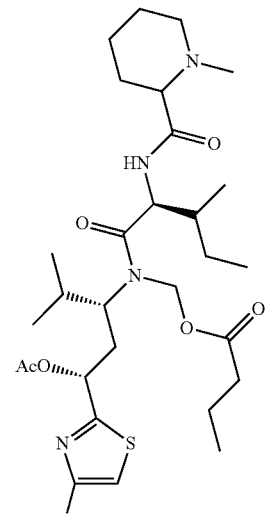

-continued

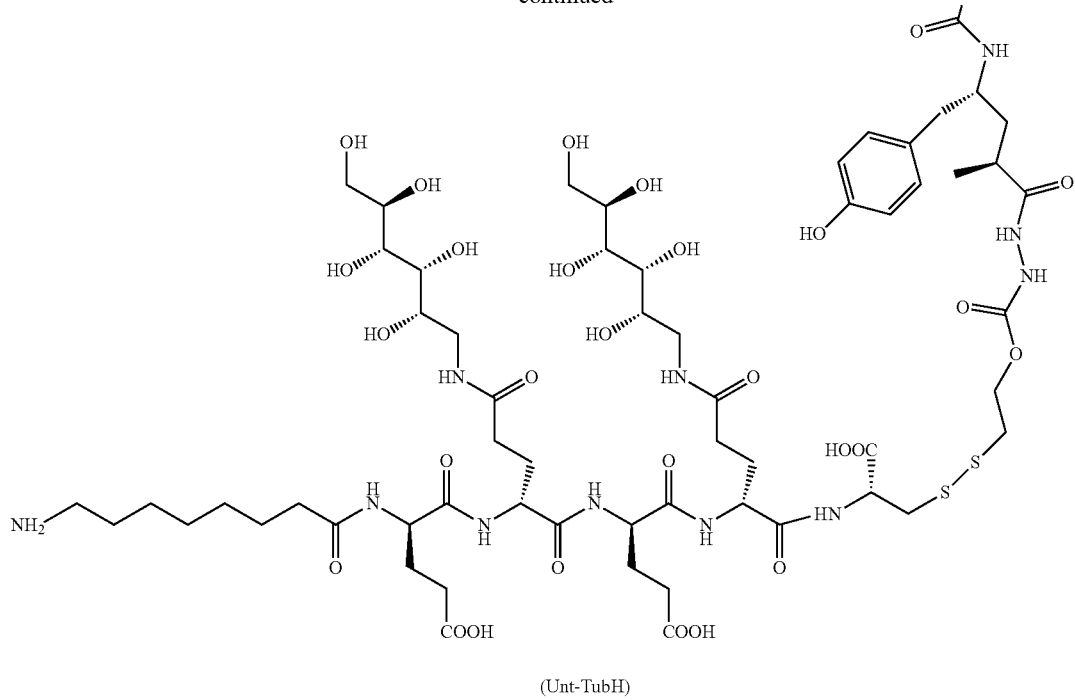

(Unt-TubH)

Conjugate 25

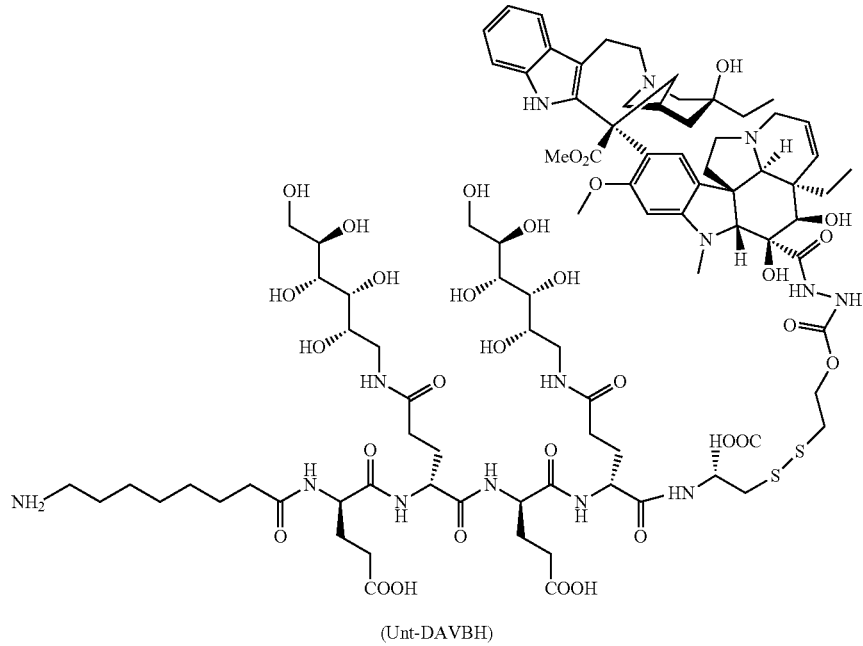

(Unt-DAVBH)

Determination of In Vitro Potency of Targeted Therapeutic Agents

Figure 13A:
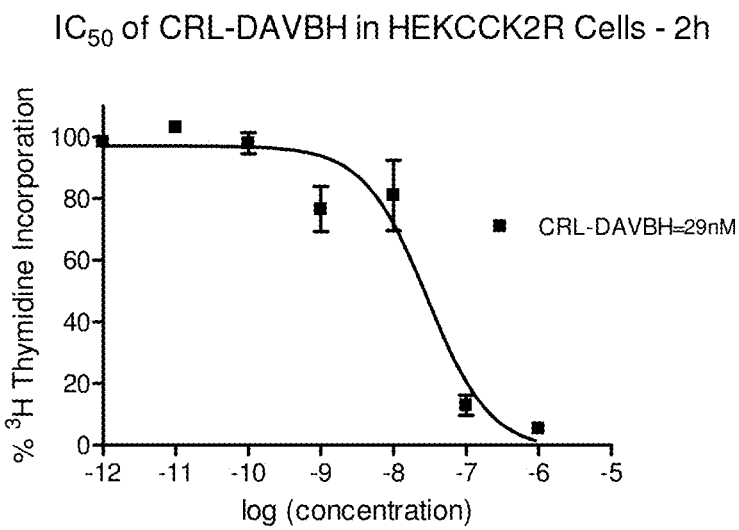
FIGS. 13A-C are line graphs displaying the dose-dependent in vitro cytotoxicity study of compound 23 in HEK CCK2R cells at 2 hours (FIG. 13A), 4 hours (FIG. 13B) and 9 hours (FIG. 13C).
Figure 13B:
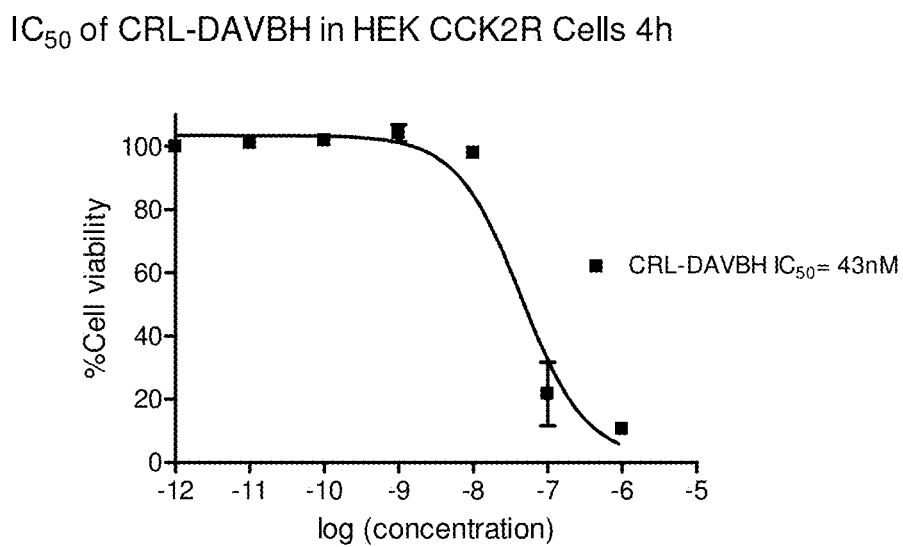
Figure 13C:
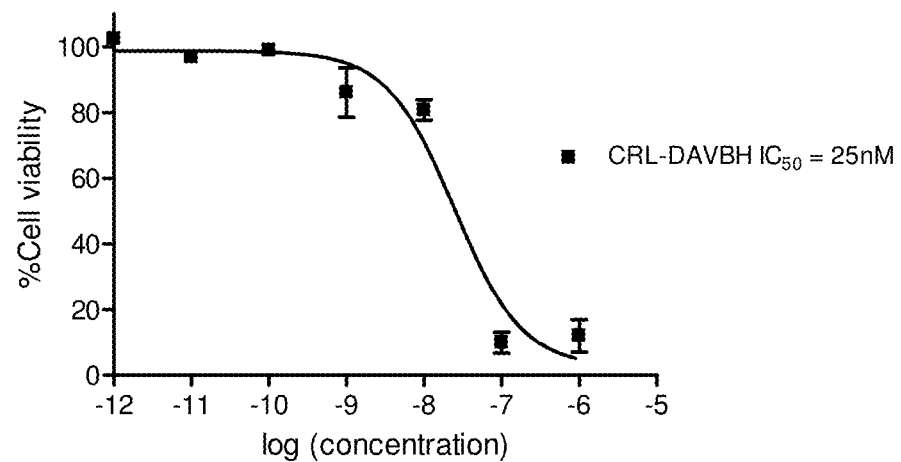

FIGS. 13A-C show the results of a study on the cytotoxicity of conjugate 23 in HEK CCK2R cells, shown at varying hours from introduction. CW-2478 denotes conjugate 23, with FIG. 13A showing values at 2 hours, FIG. 13B showing the values at 4 hours, and FIG. 13C showing the values at 9 hours.

Figure 14:
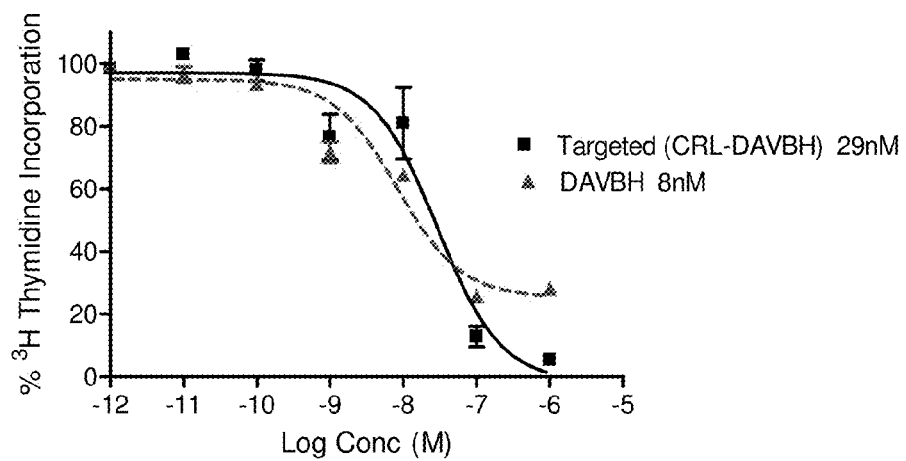
FIG. 14 shows in vitro potency of free desacetyl vinblastine hydrazide and conjugate 23 (CRL-desacetyl vinblastine monohydrazide).
Figure 15:
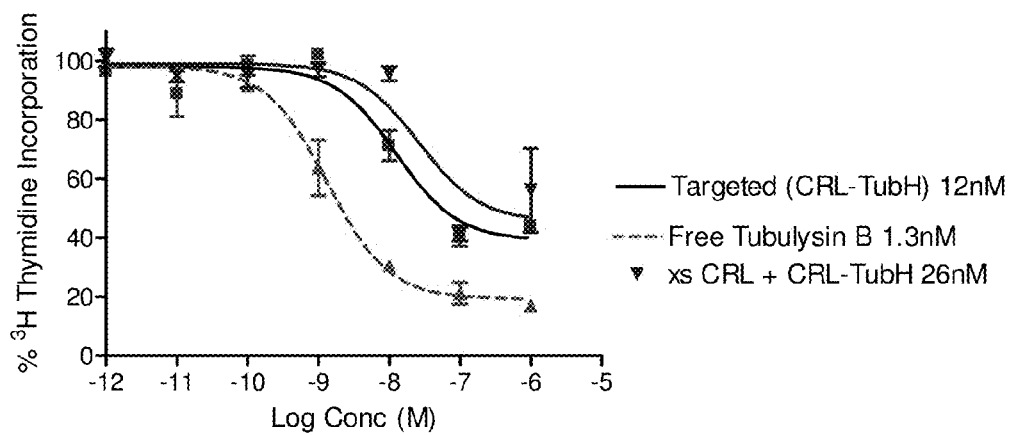
FIG. 15 shows in vitro potency of free tubulysin B and conjugate 22 (CRL-tubulysin B hydrazide) in the presence and absence of 100 fold Z-360.
Figure 16:
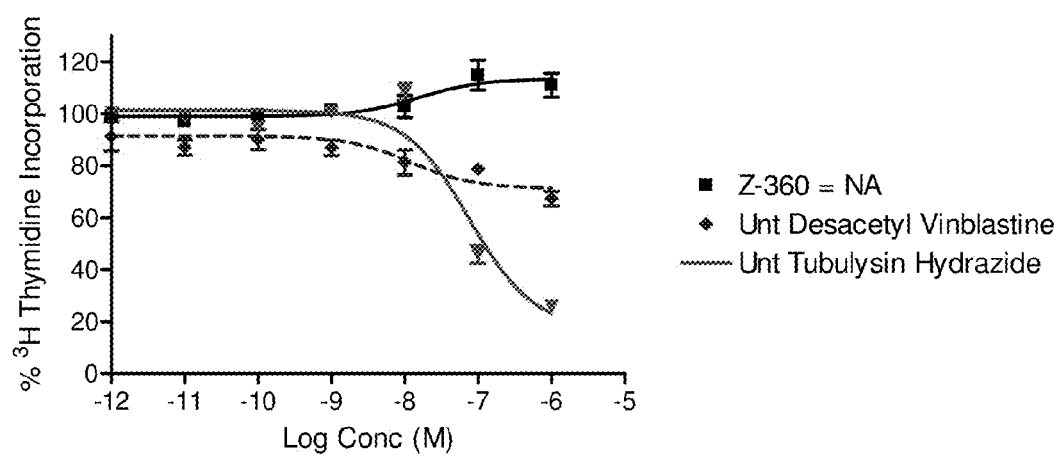
FIG. 16 shows in vitro potency of Z-360, untargeted desacetyl vinblastine hydrazide (conjugate 25) and untargeted tubulysin B hydrazide (conjugate 24).

In further studies shown in FIGS. 14 and 15, vinblastine and tubulysin b again exhibit dose dependent toxicity in HEK 293 cells expressing the CCK2R resulting in $IC_{50}$ of 8 and 1.3 nM respectively. Conjugates 22 and 23 were included in these studies and both were found to be potent in HEK 293 cells expressing the CCK2R receptor with $IC_{50}$ of 12 and 28 nM respectively (FIG. 14, 15). This indicates that conjugation with the linker does not alter the intrinsic activity of the drugs. On the other hand, Z-360 (FIG. 16) shows no concentration dependent cell toxicity for the concentration range used. This may partly explain the modest in vivo antitumor observed activity despite its impressive antagonistic effects. The un-targeted drugs (Unt-TubH and Unt-DAVBH; FIG. 16), show a little to no potency.

Determination of In Vivo Potency of Targeted Therapeutic Agents

Following the promising results obtained in vitro with the Z-360 targeted chemotherapeutics, antitumor effects of the compounds were investigated in vivo. HEK 293 cells expressing CCK2R ($5.0 \times 10^6$ in 50% HC matrigel) were injected in the shoulder of 5-6 week old female nu/nu mice. Tumors were measured in two perpendicular directions every two to three days with vernier calipers, and their volumes calculated as $0.5 \times L \times W^2$ where L is the longest axis (in millimeters) and W is the axis perpendicular to L (in millimeters). Dosing solutions were prepared in saline and administered through either the lateral vein of the mice for Tubulysin B conjugates or intraperitoneally for desacetyl-vinblastine hydrazide conjugates. Dosing was initiated when the subcutaneous tumors reached ~100 mm$^3$ in volume. Each mouse received 2 μmol/kg of the test conjugate in 100 microliters of saline per injection, three times a week for three weeks. Mouse weights were also recorded at each dosing as a measure of gross toxicity. Mice in the control groups received no treatment.

Figure 17A:
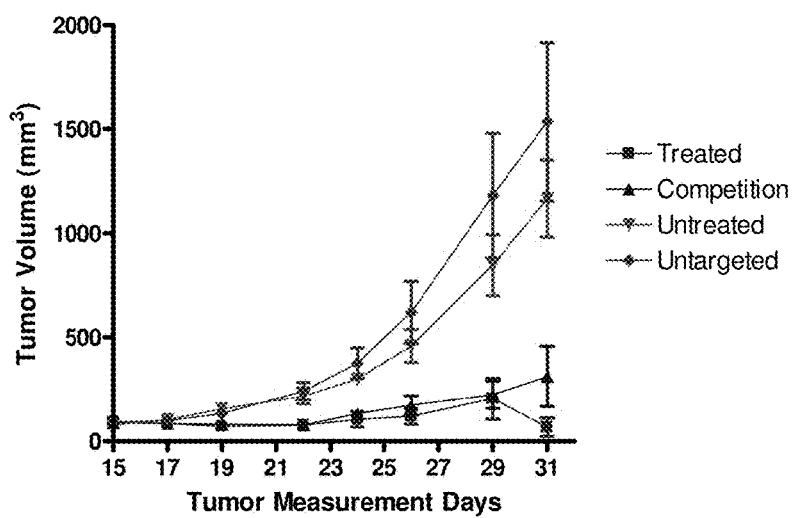
FIGS. 17A-B show the effect of conjugate 23 (CRL-desacetyl vinblastine monohydrazide) on the a) growth of subcutaneous HEK 293 tumors transfected with CCK2R and on the b) weights of the treated mice.
Figure 17B:
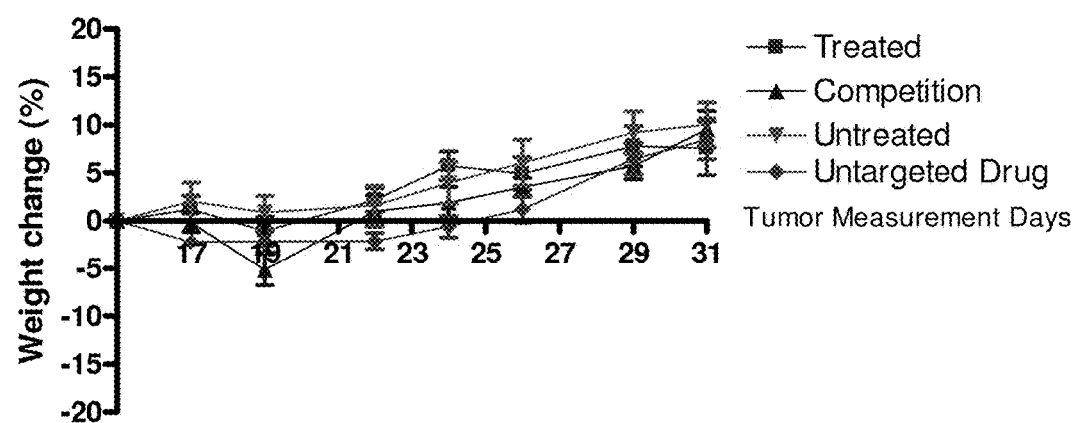
Figure 18:
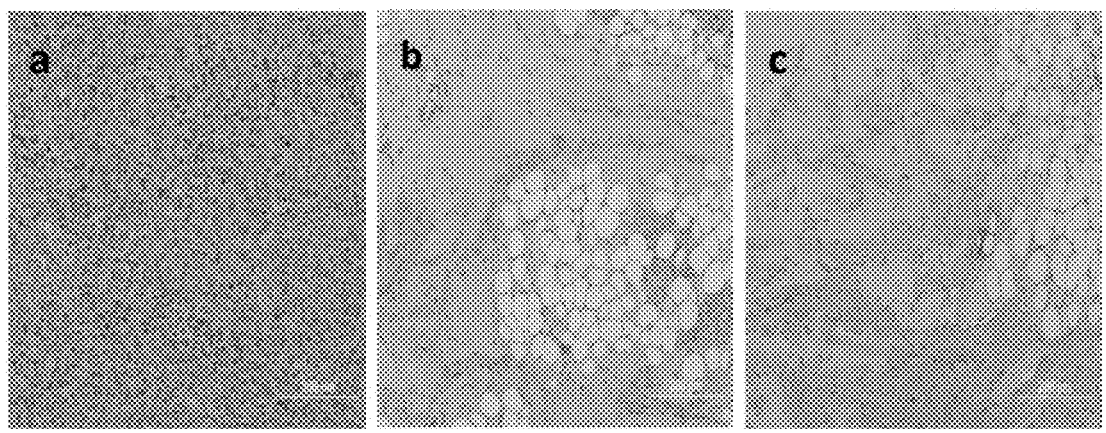
FIG. 18 shows H&E staining of mice treated with desacetyl vinblastine hydrazide conjugates: a) untreated group; b) treated with conjugate 23 (CRL-desacetyl vinblastine monohydrazide); c) treated with conjugate 23 and excess Z-360.
Figure 19A:
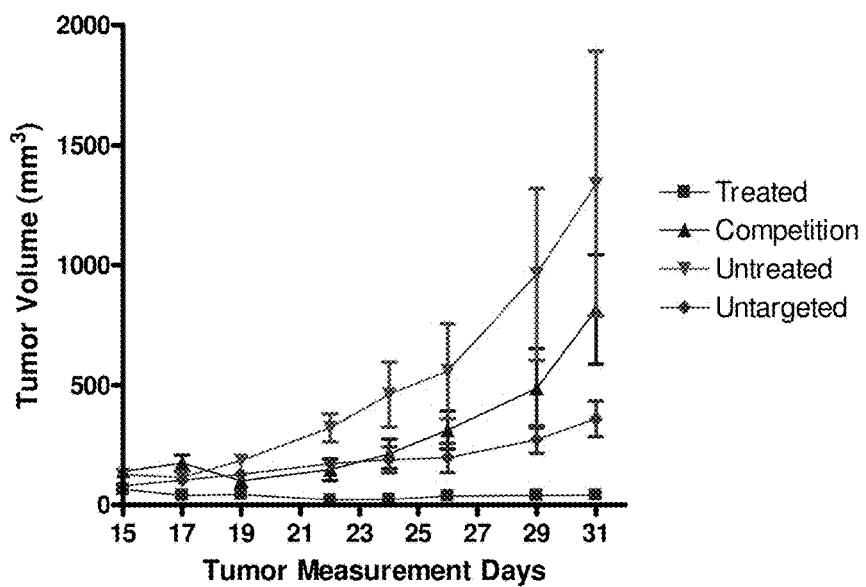
FIG. 19 shows the effect of conjugate 22 (comprising CRL-tubulysin B hydrazide) on the growth of subcutaneous HEK 293 tumors transfected with CCK2R and on the weights of the treated mice.
Figure 19B:
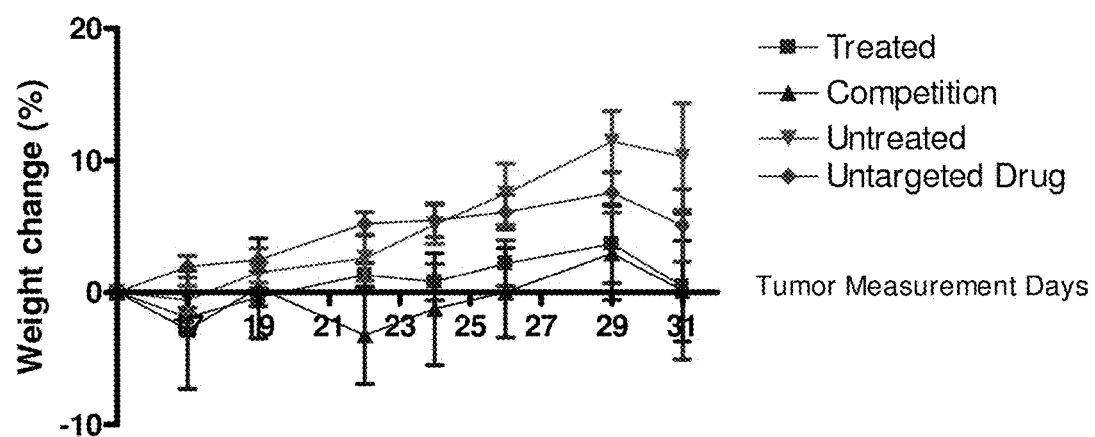

As shown in FIGS. 17a and 19a, in comparison to untreated controls conjugates 22 and 23 showed remarkable antitumor activity in CCK2R expressing tumor bearing mice. However whereas conjugate 23-treated tumors were observed to remain the same size during the period of the study, treatment with conjugate 22 resulted in reduction of tumor sizes and disappearance of 3/5 tumors. The remaining tumor masses from the conjugate 23 group were analyzed by H&E staining and as can be seen in FIG. 18 with the remaining mass in the conjugate 23 and conjugate 23+competition groups contain very few malignant cells. As shown in FIG. 17a, tumors treated with the untargeted compounds (Unt-DAVBH) grew at almost the same rate as untreated controls. On the other hand, the untargeted tubulysin compound (Unt-TubH; FIG. 19a) demonstrated modest tumor inhibition consistent with the partial potency observed in the in vitro studies using the same compound. Importantly, body weights in each of the groups (FIGS. 17b and 19b) studied remained essentially unchanged over the course of the study suggesting that targeted the therapy is not grossly toxic to the animal.

Surprisingly, mice that were pretreated with 100-fold excess of Z-360 with the aim of blocking the receptors, still exhibited antitumor activity when treated with the targeted drugs. We hypothesize that this may be due to the fact that once the conjugate localizes in the tumor cell surface the disulfide bond gets cleaved releasing free drug that diffuses through the membrane.

While the invention has been described with reference to certain particular embodiments thereof, those skilled in the art will appreciate that various modifications may be made without departing from the spirit and scope of the invention. The scope of the appended claims is not to be limited to the specific embodiments described.

REFERENCES

All patents and publications mentioned in this specification are indicative of the level of skill of those skilled in the art to which the invention pertains. Each cited patent and publication is incorporated herein by reference in its entirety. All of the following references have been cited in this application:

1. Dufresne M., Seva C., Fourmy D. Cholecystokinin and gastrin receptors. Physiol Rev. 86:805-847, 2006
2. Young-Mee Lee, Martin Bernborn, Edward W. McBride, Ming Lu, Lee Kolakowski and Alan S. Korpin. The Human Cholecystokinin-B/Gastrin Receptor. Journal of Biological Chemistry 268 (11) 8164-8169, 1993
3. Miller L. J. Does the Human Pancreas have a type A or B personality? Gastroenterology 111, 1767-1770, 1996
4. Monstein H J, Nylander A G, Salehi A, Chen D. Lundquist I, Hakanson R. Cholecystokinin A and Cholecystokinin-B/Gastrin receptor mRNA expression in the gastrointestinal tract and pancreas of the rat and human. A polymerase chain reaction study. Scand J Gastroenterol 31 383-390, 1996
5. Tang C, Biemond I. Lamers C B. Cholecystokinin receptors in human pancreas and gall bladder muscle: a comparative study. Gastroenterology 111, 1621-1626, 1996
6. Saillan-Barreau Dufresne M. Clerc P. Sanchez D. Corominola H. Moriscot C. Guy Crotte O. Escrieut C. Vaysse N. Gomis R. Tarasova N. Fourmy D. Evidence for a functional role of the Cholecystokinin-B/gastrin receptor in the human fetal and adult pancreas. Diabetes 48 2015-2021, 1999
7. Brand S J, Fuller P J. Journal Biol. Chem. 263 5341-5347 1988
8. Jean Claude Reubi, Beatrice Waser, Ursula Laderach, Christian Stettlet, Helmut Friess, Fred Hatter and Adrian Schmassmann. Localization of Cholecystokinin A and Cholecystokinin-B/Gastrin receptors in the human stomach
9. Berna M. J, Jensen R. T. Role of CCK/gastrin receptors in gastrointestinal/metabolic diseases and results of human studies using gastrin/CCK receptor agonists/antagonists in these diseases. Curr. Top Med Chem. 7:1211-1231, 2007
10. Weinberg D S. Ruggeri B. Barber M T, Biswas S. Miknyocki S. Waldman S A. Cholecystokinin A and B receptors are differentially expressed in normal and pancreatic adenocarcinoma. J. Clinical Investigation 100, 597-603, 1997
11. Caplin M, Savage K, Khan K, Brett B, Rode J, Varro A, and Dhillon A. Expression and processing of gastrin in pancreatic adenocarcinoma. Br J Surg. 87: 1035-1040, 2000.
12. Reubi, J. C., and Waser, B. Unexpected high incidence of cholecystokinin B/gastrin receptors in human medullary thyroid carcinomas. Int. J. Cancer, Vol. 67, pp. 644-647, 1996
13. Sethi, T., Herget, T., Wu, S. V., Walsh, J. H., and Rozengurt, E. CCK-A and CCK-B receptors are expressed in small cell lung cancer lines and mediate Ca2+ mobilization and clonal growth. Cancer Res., Vol. 53, pp. 5208-5213, 1993.
14. Reubi J C, Schaer J C, Waser B. Cholecystokinin (CCK)-A and CCK-B/gastrin receptors in human tumors. 7, April 1, Cancer Res., Vol. 57, pp. 1377-86, 1997
15. Hur K, Kwak M K, Lee H J, Park D J, Lee H K, Lee H S, Kim W H, Michaeli D, Yang H K. Expression of gastrin and its receptor in human gastric cancer tissues. 2, February J Cancer Res Clin Oncol., Vol. 132, pp. 85-91, 2006
16. Smith, Palmer J. Quantitative analysis of gastrin mRNA and peptide in normal and cancerous human pancreas. International Journal of Molecular Medicine 2(3) 309-315 1998.
17. Ferrand A., Timothy C. Wang. Gastrin and Cancer. Cancer Letters 238(1): 15-29, 2006
18. Grabowska A. M, Morris T. M., Mackenzie A. J, Kumari R., Hamano H., Emori Y., Yoshinaga K., Watson S. A. Preclinical Evaluation of a new orally active CCK-2R antagonist Z-360 in gastrointestinal cancer models. Regulatory Peptides 146 46-57 2008.
19. Todisco A., Ramamoorthy S., Witham T., Pausawasdi N., Srinivasan S., Dickinson C. J., Askari F. K, Krametter D. Molecular Mechanisms for the antiapoptotic actions of gastrin. Am J Physiol Gastrointest Liver Physiol 280: G298-G307, 2001
20. Jian Jiang, Man Ling Chen, Quin Zhou Zhang, Yan Zao, Yuan Xi. Blocking gastrin and CCK-B autocrine loop affects cell proliferation and apoptosis in vitro. Molecular and Cellular Biochemistry 343 (1-2) 133-141
21. Blockade of cholecystokin-2 receptor and cyclooxygenase 2 synergistically induces cell apoptosis and inhibits the proliferation of human gastric cancer cells in vitro. Cancer Letters 263 (2) 302-311 2008
22. Körner M, Waser B, Reubi J C, Miller L J. *CCK(2) receptor splice variant with intron 4 retention in human gastrointestinal and lung tumours*4, April 2010, J Cell Mol Med., Vol. 14, pp. 933-43.
23. Smith, J. P., Verderame, M. F., McLaughlin, P., Martenis, M., Ballard, E., and Zagon, I. S. *Characterization of the CCK-C(cancer) receptor in human pancreatic cancer.* 2002, Int. J. Mol. Med., Vol. 10, pp. 689-694.
24. Olszewska-Pazdrak B, Townsend C M Jr, Hellmich M R. *Agonist-independent activation of Src tyrosine kinase by a cholecystokinin-2 (CCK2) receptor splice variant* 39, Sep. 24, 2004, J Biol Chem., Vol. 279, pp. 40400-4.
25. Hellmich M R, Rui X L, Fleming R Y, Evers B M, Townsend Jr C M Human colorectal cancers express a constitutively active Cholecystokinin-B/gastrin receptor that stimulates cell growth. J. Biol. Chem 275, 32122-32128, 2000
26. Chao C, E. Goluszko, Y-T Lee, AA Kolokoltsov, RA Davey, T Uchida, CM Townsend Jr and MR Hellmich. Constitutively active CCK2 Receptor splice variant increases src-dependent HIF-1alpha expression and tumor growth. Oncogene 26, 1013-1019, 2007
27. Chao C, Kirk L. Ives, Elizabeth Goluszko, Andrey A Kolokoltsov, Robert A. Davey, Courtney M. Townsend Jr and Mark R. Hellmich. Src Regulates constitutive internalization and rapid resensitization of a Cholecystokinin 2 receptor splice variant. Journal of Biological Chemistry 280 (39)33368-33373, 2005
28. Rosario Herranz. Cholecystokinin antagonists: Pharmacological and therapeutic potential. Medicinal Research reviews 23 (5) 559-605, 2003
29. Kawasaki D., Emori Y., Eta R., Iino Y., Hamano H., Yoshinaga K., Tanaka T., Takei M., and Watson S. A. Effect of Z-360, a novel orally active CCK-2/gastrin receptor antagonist on tumor growth in human pancreatic adenocarcinoma cell lines in vivo and mode of action determinations in vitro. Cancer Chemother. Pharmacol. 61(5): April, 2008
30. Nobuyoshi Kobayashi, Koichi Seto, Yuki Orikawa, Hiroki Hamano, Koji Yoshinaga and Mineo Takei. Z-360, a novel Cholecystokinin-2/gastrin receptor antagonist, inhibits Gemcitabine induced expression of the vascular endothelial growth factor gene in human pancreatic cancer cells. Biol. Pharm. Bull. 33 (2) 216-222, 2010
31. Grabowska A. M, Morris T M., McKenzie A. J., Kumari R., Hamano H., Emori Y., Yoshinaga K., Watson S. A., Regulatory Peptides 146 46-57, 2008
32. Currutto G. A chemical method for the preparation of novel 1,5 benzodiazepines acting as CCK-B Antagonists in high enantiomeric purity. Tetrahedron 53 (21) 7347-7364 1997
33. Lauffer D. J., Mullican M. D., A practical synthesis of (S) 3-tert-Butoxycarbonylamino-2-oxo-2,3,4,5-tetrahydro-1, 5-benzodiazepine-1-acetic acid methyl ester as a conformationally restricted dipeptido-Mimetic for caspase-1 (ICE) inhibitors. Biorganic and Medicinal Chem. Lett. 12(8) 1225-1227, 2002
34. Shinozaki K., Yoneta T., Murata M., Miura N., Maeda K., 1,5 Benzodiazepine derivatives U.S. Pat. No. 6,344, 452 BI. Feb. 5, 2002
35. Shinozaki K., Yoneta T., Murata M., Miura N., Maeda K., Taguchi K., Kawase H., NaoyoshiCalcium salts of 1,5 Benzodiazepine derivatives, process or producing salts and drugs containing the same. U.S. Pat. No. 6,747,022 B2. Jun. 8, 2004
36. Reddy J A, Xu L C, Parker N, Vetzel M, Leamon C P. Preclinical evaluation of (99m)Tc-EC20 for imaging folate receptor-positive tumors. J Nucl Med. 2004 May; 45(5):857-66
37. Iontcho R. Vlahov, Hari Krishna R. Santhapuram, Fei You, Yu Wang, Paul J. Kleindl, Spencer J. Hahn, Jeremy F. Vaughn, Daniel S. Reno and Christopher P. Leamon. Journal of Organic Chemistry 75, 3685-3691 2010Kilonda A., Compernolle F., Toppet S., Hoornaert G. J., The Synthesis of 7-carbonyl homolgues of 1-deoxynojirimycin 9. Tetrahedron Letters 1994, 35(48) 9047-9050
38. Reddy, J. A.; Dorton, R.; Dawson, A.; Vetzel, M.; Parker, N.; Nicoson, J. S.; Westrick, E.; Klein, P. J.; Wang, Y.; Vlahov, I. R.; Leamon, C. P.: In vivo structural activity and optimization studies of folate-tubulysin conjugates. Molecular pharmaceutics 2009, 6, 1518-25
39. Vlahov, I. R.; Santhapuram, H. K.; Kleindl, P. J.; Howard, S. J.; Stanford, K. M.; Leamon, C. P.: Design and regioselective synthesis of a new generation of targeted chemotherapeutics. Part 1: EC145, a folic acid conjugate of desacetylvinblastine monohydrazide. *Bioorganic & medicinal chemistry letters* 2006, 16, 5093-6

What is claimed is:
1. A conjugate of formula

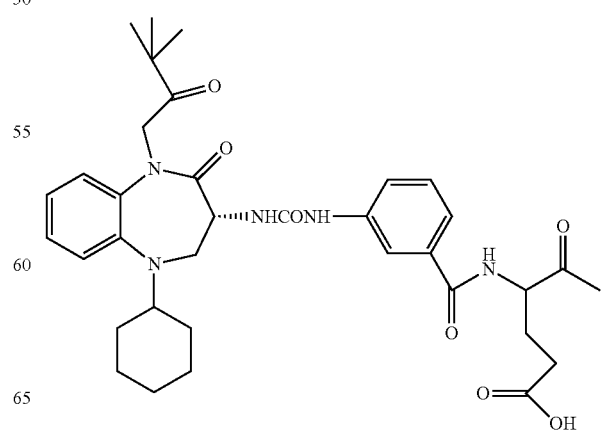

-continued
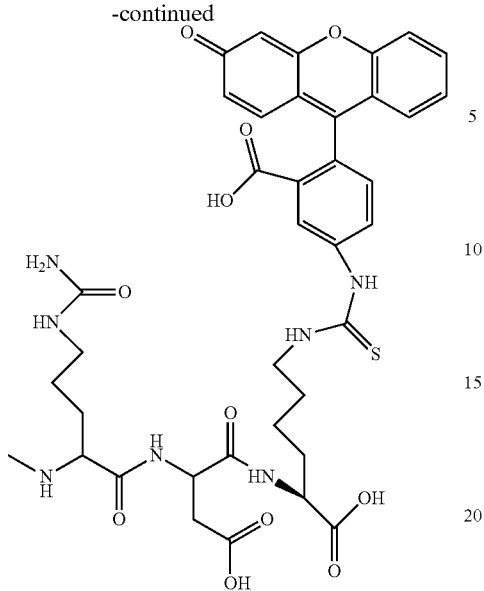
or a pharmaceutically acceptable salt thereof.
* * * * *